US009403855B2

(12) United States Patent
Wong et al.

(10) Patent No.: US 9,403,855 B2
(45) Date of Patent: Aug. 2, 2016

(54) ZANAMIVIR PHOSPHONATE CONGENERS WITH ANTI-INFLUENZA ACTIVITY AND DETERMINING OSELTAMIVIR SUSCEPTIBILITY OF INFLUENZA VIRUSES

(75) Inventors: Chi-Huey Wong, La Jolla, CA (US); Jim-Min Fang, Taipei (TW); Yih-Shyun Edmund Cheng, Taipei (TW); Jiun-Jie Shie, Taipei (TW)

(73) Assignee: ACADEMIA SINICA (TW)

( * ) Notice: Subject to any disclaimer, the term of this patent is extended or adjusted under 35 U.S.C. 154(b) by 336 days.

(21) Appl. No.: 13/697,794

(22) PCT Filed: May 10, 2011

(86) PCT No.: PCT/US2011/035982
§ 371 (c)(1),
(2), (4) Date: May 6, 2013

(87) PCT Pub. No.: WO2011/143262
PCT Pub. Date: Nov. 17, 2011

(65) Prior Publication Data
US 2013/0225532 A1 Aug. 29, 2013

Related U.S. Application Data

(60) Provisional application No. 61/333,137, filed on May 10, 2010.

(51) Int. Cl.
C07D 309/28 (2006.01)
C07F 9/655 (2006.01)
G01N 33/569 (2006.01)
A61K 31/665 (2006.01)
A61K 31/683 (2006.01)

(52) U.S. Cl.
CPC ............. *C07F 9/6552* (2013.01); *A61K 31/665* (2013.01); *A61K 31/683* (2013.01); *G01N 33/56983* (2013.01); *G01N 2333/11* (2013.01)

(58) Field of Classification Search
CPC .............................. C07D 309/28; A01N 43/16
See application file for complete search history.

(56) References Cited

U.S. PATENT DOCUMENTS

| 3,773,919 | A | 11/1973 | Boswell et al. |
| RE30,985 | E | 6/1982 | Cartaya |
| 4,419,446 | A | 12/1983 | Howley et al. |
| 4,560,655 | A | 12/1985 | Baker |
| 4,601,978 | A | 7/1986 | Karin |
| 4,657,866 | A | 4/1987 | Kumar |
| 4,676,980 | A | 6/1987 | Segal et al. |
| 4,767,704 | A | 8/1988 | Cleveland et al. |
| 4,816,567 | A | 3/1989 | Cabilly et al. |
| 4,927,762 | A | 5/1990 | Darfler |
| 4,975,278 | A | 12/1990 | Senter et al. |
| 5,004,697 | A | 4/1991 | Pardridge |
| 5,112,596 | A | 5/1992 | Malfroy-Camine |
| 5,122,469 | A | 6/1992 | Mather et al. |
| 5,229,275 | A | 7/1993 | Goroff |
| 5,264,365 | A | 11/1993 | Georgiou et al. |
| 5,268,164 | A | 12/1993 | Kozarich et al. |
| 5,395,541 | A | 3/1995 | Carpenter et al. |
| 5,500,362 | A | 3/1996 | Robinson et al. |
| 5,506,206 | A | 4/1996 | Kozarich et al. |
| 5,508,192 | A | 4/1996 | Georgiou et al. |
| 5,545,806 | A | 8/1996 | Lonberg et al. |
| 5,545,807 | A | 8/1996 | Surani et al. |
| 5,565,332 | A | 10/1996 | Hoogenboom et al. |
| 5,567,610 | A | 10/1996 | Borrebaeck et al. |
| 5,569,825 | A | 10/1996 | Lonberg et al. |
| 5,571,894 | A | 11/1996 | Wels et al. |
| 5,580,717 | A | 12/1996 | Dower et al. |
| 5,587,458 | A | 12/1996 | King et al. |
| 5,591,669 | A | 1/1997 | Krimpenfort et al. |
| 5,625,126 | A | 4/1997 | Lonberg et al. |

(Continued)

FOREIGN PATENT DOCUMENTS

| EP | 404097 A2 | 12/1990 |
| EP | 1391213 A1 | 2/2004 |
| EP | 2123271 A1 | 11/2009 |
| JP | 05-507068 A | 10/1993 |
| JP | 2000-506008 A | 5/2000 |
| WO | WO 87/00195 A1 | 1/1987 |
| WO | WO 90/03430 A1 | 4/1990 |
| WO | WO 91/00360 A1 | 1/1991 |
| WO | WO 91/10741 A1 | 7/1991 |
| WO | WO 92/00373 A1 | 1/1992 |

(Continued)

OTHER PUBLICATIONS

Udommaneethanakit, 2009, J. Chem. Inf. Model, vol. 49, p. 2323-2332.*
CAPLUS Record of Udommaneethanakit et al; DN 151:462187, 2009.*
Andrews et al., "Synthesis and influenza virus inhibitory activity of analogues of 4-Guanidino-Neu5Ac2en (Zanamivir) modified in the glycerol side-chain," *Eur. J. Med. Chem.*, Jul.-Aug. 1999, 34(7-8):563-574.

(Continued)

*Primary Examiner* — Michael Barker
*Assistant Examiner* — Karen Cheng
(74) *Attorney, Agent, or Firm* — Duane Morris LLP

(57) ABSTRACT

Methods and compositions for detection of drug resistant pathogens and treatment against infections thereof are provided. Methods for detection of oseltamivir-resistant influenza viruses by competitive binding assays utilizing non-oseltamivir influenza virus neuraminidase inhibitors and oseltamivir carboxylate are provided. Influenza virus neuraminidase inhibitors coupled to sensors and useful for employment in the methods of the invention are disclosed. Novel phosphonate compounds active as neuraminidase inhibitors against wild-type and oseltamivir-resistant influenza strains of H1N1, H5N1 and H3N2 viruses are disclosed. An enantioselective synthetic route to preparation of these phosphonate compounds via sialic acid is provided.

14 Claims, 14 Drawing Sheets

(56) References Cited

U.S. PATENT DOCUMENTS

| | | | |
|---|---|---|---|
| 5,633,425 | A | 5/1997 | Lonberg et al. |
| 5,641,870 | A | 6/1997 | Rinderknecht et al. |
| 5,648,237 | A | 7/1997 | Carter |
| 5,661,016 | A | 8/1997 | Lonberg et al. |
| 5,677,180 | A | 10/1997 | Robinson et al. |
| 5,686,416 | A | 11/1997 | Kozarich et al. |
| 5,733,743 | A | 3/1998 | Johnson et al. |
| 5,736,137 | A | 4/1998 | Anderson et al. |
| 5,821,337 | A | 10/1998 | Carter et al. |
| 5,837,234 | A | 11/1998 | Gentile et al. |
| 5,840,523 | A | 11/1998 | Simmons et al. |
| 5,869,046 | A | 2/1999 | Presta et al. |
| 6,004,940 | A | 12/1999 | Marasco et al. |
| 6,027,888 | A | 2/2000 | Georgiou et al. |
| 6,083,715 | A | 7/2000 | Georgiou et al. |
| 6,265,150 | B1 | 7/2001 | Terstappen et al. |
| 6,329,173 | B1 | 12/2001 | Marasco et al. |
| 6,528,286 | B1 | 3/2003 | Ryll |
| 6,703,019 | B1 | 3/2004 | Malfroy-Camine |
| 6,824,780 | B1 | 11/2004 | Devaux et al. |
| 6,984,630 | B1 | 1/2006 | Descamps et al. |
| 7,090,973 | B1 | 8/2006 | Breton |
| 7,151,164 | B2 | 12/2006 | Hansen et al. |
| 7,888,337 | B2 | 2/2011 | Wong et al. |
| 8,101,179 | B2 | 1/2012 | Numazaki et al. |
| 2002/0025313 | A1 | 2/2002 | Micklus et al. |
| 2002/0038086 | A1 | 3/2002 | Hynynen et al. |
| 2002/0065259 | A1 | 5/2002 | Schatzberg et al. |
| 2003/0073713 | A1 | 4/2003 | Schoenhard |
| 2003/0083299 | A1 | 5/2003 | Ferguson |
| 2003/0104402 | A1 | 6/2003 | Zauderer et al. |
| 2003/0118592 | A1 | 6/2003 | Ledbetter et al. |
| 2003/0129186 | A1 | 7/2003 | Beliveau et al. |
| 2003/0162695 | A1 | 8/2003 | Schatzberg et al. |
| 2003/0175884 | A1 | 9/2003 | Umana et al. |
| 2004/0072290 | A1 | 4/2004 | Umana et al. |
| 2004/0131692 | A1 | 7/2004 | Kreuter et al. |
| 2004/0204354 | A1 | 10/2004 | Nelson et al. |
| 2005/0089473 | A1 | 4/2005 | Black et al. |
| 2005/0106108 | A1 | 5/2005 | Hansen et al. |
| 2005/0123546 | A1 | 6/2005 | Umana et al. |
| 2005/0124533 | A1 | 6/2005 | Schatzberg et al. |
| 2006/0073122 | A1 | 4/2006 | Koezuka et al. |
| 2006/0073161 | A1 | 4/2006 | Breton |
| 2007/0224189 | A1 | 9/2007 | Lazar et al. |
| 2007/0238871 | A1 | 10/2007 | Tsuji et al. |
| 2009/0285837 | A1 | 11/2009 | Kao et al. |
| 2010/0009339 | A1 | 1/2010 | Bovin et al. |
| 2010/0173323 | A1 | 7/2010 | Strome |
| 2011/0263828 | A1 | 10/2011 | Wong et al. |
| 2012/0171201 | A1 | 7/2012 | Sapra |
| 2012/0178705 | A1 | 7/2012 | Liang et al. |
| 2012/0226024 | A1 | 9/2012 | Wang et al. |
| 2013/0230886 | A1 | 9/2013 | Votsmeier et al. |
| 2013/0337018 | A1 | 12/2013 | Fox |
| 2014/0086916 | A1 | 3/2014 | Zha |
| 2014/0127241 | A1 | 5/2014 | Leuschner et al. |

FOREIGN PATENT DOCUMENTS

| | | |
|---|---|---|
| WO | WO-92/06691 A1 | 4/1992 |
| WO | WO 93/01161 A1 | 1/1993 |
| WO | WO 93/06213 A1 | 4/1993 |
| WO | WO 93/08829 A1 | 5/1993 |
| WO | WO 93/16185 A2 | 8/1993 |
| WO | WO 94/04690 A1 | 3/1994 |
| WO | WO 96/07754 A1 | 3/1996 |
| WO | WO 96/16673 A1 | 6/1996 |
| WO | WO 96/33735 A1 | 10/1996 |
| WO | WO 96/34096 A1 | 10/1996 |
| WO | WO 97/17852 A1 | 5/1997 |
| WO | WO 98/02463 A1 | 1/1998 |
| WO | WO 98/24893 A2 | 6/1998 |
| WO | WO 99/57134 A1 | 11/1999 |
| WO | WO 03/068821 A2 | 8/2003 |
| WO | WO 03/077945 A1 | 9/2003 |
| WO | WO 2004/035607 A2 | 4/2004 |
| WO | WO 2004/056312 A2 | 7/2004 |
| WO | WO 2004/103404 A1 | 12/2004 |
| WO | WO 2005/044859 | 5/2005 |
| WO | WO 2005/103081 A2 | 11/2005 |
| WO | WO 2006/126069 A2 | 11/2006 |
| WO | WO 2006/130458 A2 | 12/2006 |
| WO | WO 2007/146847 A2 | 12/2007 |
| WO | WO-2009/029888 A2 | 3/2009 |
| WO | WO 2011/005756 A1 | 1/2011 |
| WO | WO 2013/011347 A1 | 1/2013 |
| WO | WO 2013/120066 A1 | 8/2013 |
| WO | WO 2013/181585 A2 | 12/2013 |
| WO | WO 2015/026484 A1 | 2/2015 |

OTHER PUBLICATIONS

Basak et al., "In vitro elucidation of substrate specificity and bioassay of proprotein convertase 4 using intramolecularly quenched fluorogenic peptides," *Biochem. J.*, Jun. 1, 2004, 380(Pt 2):505-514.

Chandler et al., "Synthesis of potent influenza neuraminidase inhibitor 4-guanidino Neu5Ac2en. X-Ray molecular structure of 5-acetamido-4-amino-2,6-anhydro-3,4,5-trideoxy-$_D$-erythro-$_L$-gluco-nononic acid," *J. Chem. Soc. Perkin. Trans. 1*, 1995, 1173-1180.

Cheng et al., "Oseltamivir- and amandtadine-resistant influenza viruses A (H1N1)," *Emerg. Infect. Dis.*, Jun. 2009, 15(6):966-968.

Chong et al., "Influenza virus sialidase: effect of calcium on steady-state kinetic parameters," *Biochim. Biophys. Acta*, Mar. 8, 1991, 1077(1):65-71.

Cohen-Daniel et al., "Emergence of oseltamivir-resistant influenza A/H3N2 virus with altered hemagglutination pattern in a hematopoietic stem cell transplant recipient," *J. Clin. Virol.*, Feb. 2009, 44(2):138-140.

Collins et al., "Crystal structures of oseltamivir-resistant influenza virus neuraminidase mutants," *Nature*, Jun. 26, 2008, 453(7199):1258-1261.

Cox et al., "New options for the prevention of influenza," *N. Engl. J. Med.*, Oct. 28, 1999, 341(18):1387-1388.

Cyranoski, "Threat of pandemic brings flu drug back to life," *Nat. Med.*, Sep. 2005, 11(9):909.

Dunn et al., "Zanamivir: a review of its use in influenza," *Drugs*, Oct. 1999, 58(4):761-784.

Gulland, "First cases of spread of oseltamivir resistant swine flu between pateints are reported in Wales," *BMJ.*, Nov. 23, 2009, 339:b4975.

Honda et al., "Synthesis and anti-influenza virus activity of 7-*O*-alkylated derivatives related to zanamivir," *Bioorg. Med. Chem. Lett.*, Aug. 5, 2002, 12(15):1925-1928.

Horn et al., "Investigation into an efficient synthesis of 2,3-dehydro-N-acetyl neuraminic acid leads to three decarboxylated sialic acid dimers," *Carbohydr. Res.*, Apr. 7, 2008, 343(5):936-940.

Jonges et al., "Dynamics of antiviral-resistant influenza viruses in the Netherlands, 2005-2008," *Antiviral Res.*, Sep. 2009, 83(3):290-297.

Kale et al., "Detection of intact influenza viruses using biotinylated biantennary S-sialosides," *J. Am. Chem. Soc.*, Jul. 2, 2008, 130(26):8169-8171.

Kimura et al., "Design and synthesis of immobilized Tamiflu analog on resin for affinity chromatography," *Tetrahedron Lett.*, Jul. 1, 2009, 50(26):3205-3208.

Le et al., "Avian flu: isolation of drug-resistant H5N1 virus," *Nature*, Oct. 20, 2005, 437(7062):1108.

Lee et al., "A new solvent system for efficient synthesis of 1,2,3-triazoles," *Tetrahedron Lett.*, Jul. 17, 2006, 47(29):5105-5109.

Lee et al., "An efficient and practical method for the synthesis of mono-N-protected α,ω-diaminoalkanes," *Tetrahedron Lett.*, Apr. 2, 2001, 42(14):2709-2711.

Lew et al., "Discovery and development of GS 4104 (oseltamivir): an orally active influenza neuraminidase inhibitor," *Curr. Med. Chem.*, Jun. 2000, 7(6):663-672.

(56) References Cited

OTHER PUBLICATIONS

Lu et al., "Design of a mechanism-based probe for neuraminidase to capture influenza viruses," *Angew. Chem. Int. Ed. Engl.,* Oct. 28, 2005, 44(42):6888-6892.
McKimm-Breschkin, "Resistance of influenza viruses to neuraminidase inhibitors—a review," *Antiviral Res.,* Jul. 2000, 47(1):1-17.
McKimm-Breschkin et al., "Tethered neuraminidase inhibitors that bind an influenza virus: a first step towards a diagnostic method for influenza," *Angew. Chem. Int. Ed. Engl.,* Jul. 14, 2003, 42(27):3118-3121.
Moscona, "Global transmission of oseltamivir-resistant influenza," *N. Engl. J. Med.,* Mar. 5, 2009, 360(10):953-956.
Moscona, "Oseltamivir resistance—disabling our influenza defenses," *N. Engl. J. Med.,* Dec. 22, 2005, 353(25):2633-2636.
Mossong et al., "Emergence of oseltamivir-resistant influenza A H1N1 virus during the 2007-2008 winter season in Luxembourg: clinical characteristics and epidemiology," *Antiviral Res.,* Oct. 2009, 84(1):91-94.
Potier et al., "Fluorometric assay of neuraminidase with a sodium (4-methylumbelliferyl-alpha-D-N-acetylneuraminate) substrate," *Anal. Biochem.,* Apr. 15, 1979, 94(2):287-296.
Rostovtsev et al., "A stepwise huisgen cycloaddition process: copper(I)-catalyzed regioselective 'ligation' of azides and terminal alkynes," *Angew. Chem. Int. Ed.,* Jul. 15, 2002, 41(14):2596-2599.
Russell et al., "The structure of H5N1 avian influenza neuraminidase suggests new opportunities for drug design," *Nature,* Sep. 7, 2006, 443(7107):45-49.
Schug et al., "Noncovalent binding between guanidinium and anionic groups: focus on biological- and synthetic-based arginine/guanidinium interactions with phosph[on]ate and sulf[on]ate residues," *Chem. Rev.,* Jan. 2005, 105(1):67-113.
Shie et al., "A concise and flexible synthesis of the potent anti-influenza agents tamiflu and tamiphosphor," *Angew. Chem. Int. Ed. Engl.,* 2008, 47(31):5788-5791.
Stephenson et al., "Neuraminidase inhibitor resistance after oseltamivir treatment of acute influenza A and B in children," *Clin. Infect. Dis.,* Feb. 15, 2009, 48(4):389-396.
Streicher et al., "Building a successful structural motif into sialylmimetics-cyclohexenephosphonate monoesters as pseudo-sialosides with promising inhibitory properties," *Bioorg. Med. Chem.,* Feb. 15, 2006, 14(4):1047-1057.
Udommaneethanakit et al., "Dynamic behavior of avain influenza A virus neuraminidase subtype H5N1 in complex with oseltamivir, zanamivir, peramivir, and their phosphonate analogues," *J. Chem. Inf. Model,* Oct. 2009, 49(10):2323-2332.
Vasella et al., "Synthesis of a phosphonic acid analogue of N-Acetyl-2,3- didehydro-2-deoxyneuraminic acid, an inhibitor of *Vibrio cholerae* sialidase," *Helv. Chim. Acta,* Mar. 13, 1991, 74(2):451-463.
Von Itzstein et al., "Rational design of potent sialidase-based inhibitors of influenza virus replication," *Nature,* Jun. 3, 1993, 363(6428):418-423.
Wagner et al., "Functional balance between haemagglutinin and neuraminidase in influenza virus infections," *Rev. Med. Virol.,* May-Jun. 2002, 12(3):159-166.
Wang et al., "A continuous colorimetric assay for rhinovirus-14 3C protease using peptide *p*-nitroanilides as substrates," *Anal. Biochem.,* Oct. 15, 1997, 252(2):238-245.
Wang et al., "Mechanism by which mutations at his274 alter sensitivity of influenza A virus N1 neuraminidase to oseltamivir carboxylate and zanamivir," *Antimicrob. Agents Chemother.,* Dec. 2002, 46(12):3809-3816.
Wen et al., "Synergistic effect of zanamivir-porphyrin conjugates on inhibition of neuraminidase and inactivation of influenza virus," *J. Med. Chem.,* Aug. 13, 2009, 52(15):4903-4910.
White et al., "A sialic acid-derived phosphonate analog inhibits different strains of influenza virus neuraminidase with different efficiencies," *J. Mol. Biol.,* Feb. 3, 1995, 245(5):623-634.
Ying et al., "One-bead-one-inhibitor-one-substrate screening of neuraminidase activity," *ChemBioChem.,* Oct. 2005, 6(10):1857-1865.
International Search Report and Written Opinion dated Jan. 13, 2012, from corresponding International Patent Application No. PCT/US2011/035982, 17 total pages.
Office Action mailed on Dec. 3, 2013, from corresponding Chinese Patent Application No. 201180034218.3, 15 total pages.
Office Action mailed on Oct. 22, 2014, from corresponding Chinese Patent Application No. 201180034218.3, 16 total pages.
Office Action dated Apr. 21, 2015, from related Japanese Patent Application No. 2013-510261, 6 pages.
Abrahmsén et al, "Analysis of signals for secretion in the staphylococcal protein A gene," *EMBO J.,* Dec. 30, 1985, 4(13B):3901-3906.
Altschul SF et al., "Basic local alignment search tool", *J Mol Biol.* Oct. 5, 1990;215(3):403-10.
Altschul SF, et al., "Gapped BLAST and PSI-BLAST: a new generation of protein database search programs", *Nucleic Acids Res.* Sep. 1, 1997;25(17):3389-402.
Anderson et al., "Stimulation of Natural Killer T Cells by Glycolipids", *Molecules,* May 2013, 18(12), 15662-15688.
Arié et al., "Chaperone function of FkpA, a heat shock prolyl isomerase, in the periplasm of *Escherichia coli,*" *Mol. Microbiol.,* Jan. 2001, 39(1):199-210.
Bachmann, *Cellular and Molecular Biology,* vol. 2, Chapter 72: *Derivations and Genotypes of Some Mutant Derivatives of Escherichia coli K-12,* Neidhardt et al., eds., 1987, pp. 1190-1219, American Society for Microbiology, Washington, D.C.
Baldwin et al., "Monoclonal antibodies in cancer treatment," *Lancet,* Mar. 15, 1986, 327(8481):603-605.
Barbas et al., "Assembly of combinatorial antibody libraries on phage surfaces: the gene III site," *Proc. Natl. Acad. Sci. U.S.A.,* Sep. 15, 1991, 88(18):7978-7982.
Barbas et al., "In vitro evolution of a neutralizing human antibody to human immunodeficiency virus type 1 to enhance affinity and broaden strain cross-reactivity," *Proc. Nat. Acad. Sci. U.S.A.,* Apr. 26, 1994, 91(9):3809-3813.
Barbas et al., "Semisynthetic combinatorial antibody libraries: a chemical solution to the diversity problem," *Proc. Natl. Acad. Sci. U.S.A.,* May 15, 1992, 89(10):4457-4461.
Barnes et al., "Methods for growth of cultured cells in serum-free medium," *Anal. Biochem.,* Mar. 1, 1980, 102(2):255-270.
Baselga J, et al., "Phase II study of weekly intravenous recombinant humanized anti-p185HER2 monoclonal antibody in patients with HER2/neu-overexpressing metastatic breast cancer", *J Clin Oncol.* Mar. 1996; 14(3):737-44.
Bass et al., "Hormone phage: an enrichment method for variant proteins with altered binding properties," *Proteins,* 1990, 8(4):309-314.
Beck A., "Biosimilar, biobetter and next generation therapeutic antibodies" *MAbs.* Mar.-Apr. 2011;3(2):107-10. Epub Mar. 1, 2011.
Berra et al., "Correlation between ganglioside distribution and histological grading of human astrocytomas," *Int. J. Cancer,* Sep. 15, 1985, 36(3):363-366.
Birklé et al., "Role of tumor-associated gangliosides in cancer progression," *Biochimie,* Mar.-Apr. 2003, 85(3-4):455-463.
Bobo et al., "Convection-enhanced delivery of macromolecules in the brain," *Proc. Natl. Acad. Sci. U.S.A.,* Mar. 15, 1994, 91(6) 2076-2080.
Boerner et al., "Production of antigen-specific human monoclonal antibodies from in vitro-primed human splenocytes," *J. Immunol.,* Jul. 1, 1991, 147(1):86-95.
Bothmann et al., "The periplasmic *Escherichia coli* peptidylprolyl *cis,trans*-isomerase FkpA. I. Increased functional expression of antibody fragments with and without *cis*-prolines," *J. Biol. Chem.,* Jun. 2, 2000, 275(22):17100-17105.
Brennan et al., "Preparation of bispecific antibodies by chemical recombination of monoclonal immunoglobulin $G_1$ fragments," *Science,* Jul. 5, 1985, 229(4708):81-83.
Brimble et al., "The cell surface glycosphingolipids SSEA-3 and SSEA-4 are not essential for human ESC pluripotency," *Stem Cells,* Jan. 2007, 25(1):54-62.

(56) References Cited

OTHER PUBLICATIONS

Brodeur et al., *Monoclonal Antibody Production Techniques and Applications, Chapter 4: Mouse-Human Myeloma Partners for the Production of Heterohybridomas*, Schook, ed., 1987, pp. 51-63, Marcel Dekker, Inc., New York.
Brüggemann et al., "Designer mice: the production of human antibody repertoires in transgenic animals," *Year in Immunol.*, 1993, 7:33-40.
Capel PJ et al., "Heterogeneity of human IgG Fc receptors" *Immunomethods.* Feb. 1994;4(1):25-34.
Carter et al., "High level *Escherichia coli* expression and production of a bivalent humanized antibody fragment," *Nature Biotechnology*, Feb. 1992, 10(2):163-167.
Carter et al., "Humanization of an anti-p185$^{HER2}$ antibody for human cancer therapy," *Proc. Natl. Acad. Sci. U.S.A.*, May 15, 1992, 89(10):4285-4289.
Carter PJ. "Potent antibody therapeutics by design" *Nat Rev Immunol.* May 2006;6(5):343-357.
Chang et al., "Expression of Globo H and SSEA3 in breast cancer stem cells and the involvement of fucosyl transferases 1 and 2 in Globo H synthesis," *Proc. Natl. Acad. Sci. U.S.A.*, Aug. 19, 2008, 105(33):11667-11672.
Chen et al., "Chaperone activity of DsbC," *J. Bio. Chem.*, Jul. 9, 1999, 274(28):19601-19605.
Chen et al., "Selection and analysis of an optimized anti-VEGF antibody: crystal structure of an affinity-matured Fab in complex with antigen," *J. Mol. Biol.*, Nov. 5, 1999, 293(4):865-881.
Chen et al., "Selective killing of transformed cells by cyclin/cyclin-dependent kinase 2 antagonists," *Proc. Natl. Acad. Sci. USA.*, Apr. 13, 1999, 96(8):4325-4329.
Chothia et al., "Canonical structures for the hypervariable regions of immunoglobulins," *J. Mol. Biol.*, Aug. 20, 1987, 196(4):901-917.
Clackson et al., "Making antibody fragments using phage display libraries," *Nature*, Aug. 15, 1991, 352(6336):624-628.
Clark EA et al., "Structure, function, and genetics of human B cell-associated surface molecules" *Adv Cancer Res.* 1989;52:81-149.
Clynes R, et al., "Fc receptors are required in passive and active immunity to melanoma" *Proc Natl Acad Sci U S A.* Jan. 20, 1998;95(2):652-6.
Cunningham et al., "High-resolution epitope mapping of hGH-receptor interactions by alanine-scanning mutagenesis," *Science*, Jun. 2, 1989, 244(4908):1081-1085.
Daëron, "Fc receptor biology," *Annu. Rev. Immunol.*, 1997, 15:203-234.
De Haas et al., "Fcγ receptors of phagocytes," *J. Lab. Clin. Med.*, Oct. 1995, 126(4):330-341.
Durrant et al., "Immunology in the clinic review series; focus on cancer: glycolipids as targets for tumour immunotherapy," *Clin. Exp. Immunol.*, Feb. 2012, 167(2):206-215.
Embleton et al., "In-cell PCR from mRNA: amplifying and linking the rearranged immunoglobulin heavy and light chain V-genes within single cells," *Nucl. Acids Res.*, Aug. 11, 1992, 20(15):3831-3837.
Engels et al., "Gene synthesis [new synthetic methods (77)]," *Angew. Chem. Int. Ed. Engl.*, Jun. 1989, 28(6):716-734.
Fellouse et al., "Synthetic antibodies from a four-amino-acid code: a dominant role for tyrosine in antigen recognition," *Proc. Natl. Acad. Sci. U.S.A.*, Aug. 24, 2004, 101(34):12467-12472.
Fishwild et al., "High-avidity human IgGκ monoclonal antibodies from a novel strain of minilocus transgenic mice," *Nature Biotechnol.*, Jul. 1996, 14(7):845-851.
Fredman et al., "Expression of gangliosides GD3 and 3'-isoLM1 in autopsy brains from patients with malignant tumors," *J. Neurochem.*, Jan. 1993, 60(1):99-105.
Fredman et al., "Potential ganglioside antigens associated with human gliomas," *Neurol. Res.*, Jun. 1986, 8(2):123-126.
Fredman et al., "Sialyllactotetraosylceramide, a ganglioside marker for human malignant gliomas," *J. Neurochem.*, Mar. 1988, 50(3):912-919.

Fujita M et al., "A novel disaccharide substrate having 1,2-oxazoline moiety for detection of transglycosylating activity of endoglycosidases" *Biochim Biophys Acta.* Sep. 3, 2001;1528(1):9-14.
Galfrè et al., "Preparation of monoclonal antibodies: strategies and procedures," *Methods Enzymol.*, 1981, 73(Pt B):3-46.
Gazzano-Santoro et al., "A non-radioactive complement-dependent cytotoxicity assay for anti-CD20 nonclonal antibody," *J. Immunol. Methods*, Mar. 28, 1997, 202(2):163-171.
GenBank accession No. AAA24922.1, "endoglycosidase F [Elizabethkingia meningoseptica]," May 27, 2008.
GenBank accession No. AAA24923.1, "endoglycosidase, partial [Elizabethkingia meningoseptica]," Jun. 8, 1993.
GenBank accession No. AAA24924.1.1, "endoglycosidase, partial [Elizabethkingia meningoseptica]," Jun. 7, 1993.
GenBank accession No. AAA26738.1, "endo-beta-N-acetylglucosaminidase H [Streptomyces plicatus]," Apr. 26, 1993.
GenBank accession No. J05449.1, "F.meningosepticum peptide-N-4-(N-acetyl-beta-D-glucosaminyl) asparagine amidase (PNGase F) mRNA, complete cds," Jan. 16, 1996.
GenBank accession No. YP_212855.1, "Putative exported alpha-L-fucosidase protein [Bacteroides fragilis NCTC 9343]," Mar. 2, 2014.
Gill et al., "Direct brain infusion of glial cell line-derived neurotrophic factor in Parkinson disease," *Nature Med.*, May 2003, 9(5):589-595 and Addendum from Apr. 2006, 12(4):479.
Goding, *Monoclonal Antibodies: Principles and Practice 2$^{nd}$ ed., Chapter 3: Production of Monoclonal Antibodies*, 1986, pp. 59-103, Academic Press, London.
Goochee CF et al., "The oligosaccharides of glycoproteins: bioprocess factors affecting oligosaccharide structure and their effect on glycoprotein properties", *Biotechnology* (N Y). Dec. 1991;9(12):1347-55.
Gottschling et al., "Stage-specific embryonic antigen-4 is expressed in basaloid lung cancer and associated with poor prognosis," *Eur. Respir. J.*, Mar. 2013, 41(3):656-663.
Graham et al., "Characteristics of a human cell line transformed by DNA from human adenovirus type 5," *J. Gen. Virol.*, Jul. 1977, 36(1):59-72.
Gram et al., "In vitro selection and affinity maturation of antibodies from a naive combinatorial immunoglobulin library," *Proc. Natl. Acad. Sci. U.S.A.*, Apr. 15, 1992, 89(8):3576-3580.
Green, "Targeting targeted therapy," *N. Engl. J. Med.*, May 20, 2004, 350(21):2191-2193.
Griffiths et al., "Human anti-self antibodies with high specificity from phage display libraries," *EMBO J.*, Feb. 1993, 12(2):725-734.
Gruber et al., "Efficient tumor cell lysis mediated by a bispecific single chain antibody expressed in *Escherichia coli*," *J. Immunol.*, Jun. 1, 1994, 152(11):5368-5374.
Guss et al., "Structure of the IgG-binding regions of streptococcal protein G," *EMBO J.*, Jul. 1986, 5(7):1567-1575.
Guyer et al., "Immunoglobulin binding by mouse intestinal epithelial cell receptors," *J. Immunol.*, Aug. 1976, 117(2):587-593.
Hakomori et al., "Glycosphingolipid antigens and cancer therapy," *Chem. Biol.*, Feb. 1997, 4(2):97-104.
Hakomori, "Glycosylation defining cancer malignancy: new wine in an old bottle," *Proc. Natl. Acad. Sci. U.S.A.*, Aug. 6, 2002, 99(16):10231-10233.
Hara et al., "Overproduction of penicillin-binding protein 7 suppresses thermosensitive growth defect at low osmolarity due to an spr mutation of *Escherichia coli*," *Microbial Drug Resistance*, Spring 1996, 2(1):63-72.
Harris, "Production of humanized monoclonal antibodies for in vivo imaging and therapy," *Biochem. Soc. Transactions*, Nov. 1995, 23(4):1035-1038.
Hata, K. et al., "Limited Inhibitory Effects of Oseltamivir and Zanamivir on Human Sialidases," Antimicrobial Agents and Chemotherapy, vol. 52, No. 10, Oct. 2008, in 8 pages.
Hawkins et al., "Selection of phage antibodies by binding affinity. Mimicking affinity maturation," *J. Mol. Biol.*, 1992, 226(3):889-896.
Heyman, "Complement and Fc-receptors in regulation of the antibody response," *Immunol. Lett.*, Dec. 1996, 54(2-3):195-199.

(56) References Cited

OTHER PUBLICATIONS

Hinman et al., "Preparation and characterization of monoclonal antibody conjugates of the calicheamicins: a novel and potent family of antitumor antibiotics," *Cancer Res.*, Jul. 15, 1993, 53(14):3336-3342.
Hogrefe et al., "A bacteriophage lambda vector for the cloning and expression of immunoglobulin Fab fragments on the surface of filamentous phage," *Gene*, Jun. 15, 1993, 128(1):119-126.
Holliger et al., "'Diabodies': small bivalent and bispecific antibody fragments," *Proc. Natl. Acad. Sci. U.S.A.*, Jul. 15, 1993, 90(14):6444-6448.
Honegger et al., "Yet another numbering scheme for immunoglobulin variable domains: an automatic modeling and analysis tool," *J. Mol. Biol.*, Jun. 8, 2001, 309:657-670.
Hoogenboom et al., "By-passing immunisation: Human antibodies from synthetic repertoires of germline $V_H$ gene segments rearranged in vitro," *J. Mol. Biol.*, Sep. 20, 1992, 227(2):381-388.
Hoogenboom et al., "Multi-subunit proteins on the surface of filamentous phage: methodologies for displaying antibody (Fab) heavy and light chains," *Nucl. Acids Res.*, Aug. 11, 1991 19(15):4133-4137.
Huang et al., "Carbohydrate-based vaccines with a glycolipid adjuvant for breast cancer," *Proc. Natl. Acad. Sci. U.S.A.*, Feb. 12, 2013, 110(7):2517-2522.
Hung et al., "Investigation of SSEA-4 binding protein in breast cancer cells," *J. Am. Chem. Soc.*, Apr. 24, 2013, 135(16):5934-5937.
Hurle et al., "Protein engineering techniques for antibody humanization," *Curr. Opin. Biotechnol.*, Aug. 1994, 5(4):428-433.
Inouye et al., "Single-step purification of $F(ab')_{2\mu}$ fragments of mouse monoclonal antibodies (immunoglobulins M) by hydrophobic interaction high-performance liquid chromatography using TSKgel Ether-5PW," *J. Biochem. Biophys. Methods*, Feb. 1993, 26(1):27-39.
Jackson et al., "In vitro antibody maturation: Improvement of a high affinity, neutralizing antibody against IL-1β," *J. Immunol.*, Apr. 1, 1995, 154(7):3310-3319.
Jakobovits et al., "Analysis of homozygous mutant chimeric mice: deletion of the immunoglobulin heavy-chain joining region blocks B-cell development and antibody production," *Proc. Natl. Acad. Sci. U.S.A.*, Mar. 15, 1993, 90(6):2551-2555.
Jakobovits et al., "Germ-line transmission and expression of a human-derived yeast artificial chromosome," *Nature*, Mar. 18, 1993, 362(6417):255-258.
Jenkins N, Curling EM., "Glycosylation of recombinant proteins: problems and prospects", *Enzyme Microb Technol.* May 1994;16(5):354-64.
Jones et al., "Rapid PCR-cloning of full-length mouse immunoglobulin variable regions," *Nature Biotechnol.*, Jan. 1991, 9(1):88-89.
Jones et al., "Replacing the complementarity-determining regions in a human antibody with those from a mouse," *Nature*, May 29-Jun. 4, 1986, 321(6069):522-525.
Jones, "Analysis of polypeptides and proteins," *Adv. Drug Delivery Rev.*, Jan.-Apr. 1993, 10(1):29-90.
Kam et al., "Carbon nanotubes as multifunctional biological transporters and near-infrared agents for selective cancer cell destruction," *Proc. Natl. Acad. Sci. U.S.A.*, Aug. 16, 2005, 102(33):11600-11605.
Kaneko et al., "Anti-inflammatory activity of immunoglobulin G resulting from Fc sialylation," *Science*, Aug. 4, 2006, 313(5787):670-673.
Kannagi et al., "New globoseries glycosphingolipids in human teratocarcinoma reactive with the monoclonal antibody directed to a developmentally regulated antigen, stage-specific embryonic antigen 3," *J. Biol. Chem.*, Jul. 25, 1983, 258(14):8934-8942.
Kannagi et al., "Stage-specific embryonic antigens (SSEA-3 and -4) are epitopes of a unique globo-series ganglioside isolated from human teratocarcinoma cells," *EMBO J.*, 1983, 2(12):2355-2361.
Karlin S. et al., "Methods for assessing the statistical significance of molecular sequence features by using general scoring schemes", *Proc Natl Acad Sci U S A.* Mar. 1990;87(6):2264-8.

Kato et al., "GMab-1, a high-affinity anti-3'-isoLM1/3'6'-isoLD1 IgG monoclonal antibody, raised in lacto-series ganglioside-defective knockout mice," *Biochem. Biophys. Res. Commun.*, Jan. 1, 2010, 391(1):750-755.
Kim et al., "Localization of the site of the murine IgG1 molecule that is involved in binding to the murine intestinal Fc receptor," *Eur. J. Immunol.*, 1994, 24:2429-2434.
Köhler et al., "Continuous cultures of fused cells secreting antibody of predefined specificity," *Nature*, Aug. 7, 1975, 256(5517):495-497.
Kontermann, "Intrabodies as therapeutic agents," *Methods*, Oct. 2004, 34(2):163-170.
Kostelny et al., "Formation of a bispecific antibody by the use of leucine zippers," *J. Immunol.*, Mar. 1, 1992, 148(5):1547-1553.
Kozbor, "A human hybrid myeloma for production of human monoclonal antibodies," *J. Immunol.*, Dec. 1984, 133(6):3001-3005.
Kriegler M et al., "A novel form of NF/cachectin is a cell surface cytotoxic transmembrane protein: ramifications for the complex physiology of TNF" *Cell.* Apr. 8, 1988;53(1):45-53.
Kudo et al., "Up-regulation of a set of glycosyltransferase genes in human colorectal cancer," *Lab. Invest.*, Jul. 1998, 78(7):797-811.
Lau et al., "N-Glycans in cancer progression," *Glycobiology*, Oct. 2008, 18(10):750-760.
Lee et al., "Bivalent antibody phage display mimics natural immunoglobulin," *J. Immunol. Methods*, Jan. 2004, 284(1-2):119-132.
Lee et al., "High-affinity human antibodies from phage-displayed synthetic Fab libraries with a single framework scaffold," *J. Mol. Biol.*, Jul. 23, 2004, 340(5):1073-1093.
Lefranc et al., "IMGT, the international ImMunoGeneTics database," *Nucleic Acids Res.*, Jan. 1, 1999, 27(1):209-212.
Lehninger, *Biochemistry: The Molecular Basis of Cell Structure and Function*, $2^{nd}$ ed., 1975, pp. 73-75, Worth Publishers, New York.
Leung et al., "A method for random mutagenesis of a defined DNA segment using a modified polymerase chain reaction," *Technique—A Journal of Methods in Cell and Molecular Biology*, Aug. 1989, 1(1):11-15.
Lindmark et al., "Binding of immunoglobulins to protein A and immunoglobulin levels in mammalian sera," *J. Immunol. Meth.*, Aug. 12, 1983, 62(1):1-13.
Liu C, et al., "Expansion of spleen myeloid suppressor cells represses NK cell cytotoxicity in tumor-bearing host" *Blood.* May 15, 2007;109(10):4336-42. Epub Jan. 23, 2007.
Liu et al., "Eradication of large colon tumor xenografts by targeted delivery of maytansinoids," *Proc. Natl., Acad. Sci. U.S.A.*, Aug. 6, 1996, 93(16):8618-8623.
LoBuglio et al., "Mouse/human chimeric monoclonal antibody in man: kinetics and immune response," *Proc. Natl. Acad. Sci. U.S.A.*, Jun. 1989, 86(11):4220-4224.
Lode et al., "Targeted therapy with a novel enediyne antibiotic calicheamicin $\theta^I_1$ effectively suppresses growth and dissemination of liver metastases in a syngeneic model of murine neuroblastoma," *Cancer Res.*, Jul. 15, 1998, 58(14):2925-2928.
Lonberg et al., "Antigen-specific human antibodies from mice comprising four distinct genetic modifications," *Nature*, Apr. 28, 1994, 368(6474):856-859.
Lonberg et al., "Human antibodies from transgenic mice," *Int. Rev. Immunol.*, 1995, 13(1):65-93.
Louis et al., "The 2007 WHO classification of tumours of the central nervous system," *Acta. Neuropathol.*, Aug. 2007, 114(2):97-109.
Lu et al., "Single chain anti-c-Met antibody conjugated nanoparticles for in vivo tumor-targeted imaging and drug delivery," *Biomaterials*, Apr. 2011, 32(12):3265-3274.
MacFarlane GT, et al., "Formation of glycoprotein degrading enzymes by Bacteroides fragilis" *FEMS Microbiol Lett.* Jan. 15, 1991;61(2-3):289-93.
Mandler et al., "Immunoconjugates of geldanamycin and anti-HER2 monoclonal antibodies: antiproliferative activity on human breast carcinoma cell lines," *J. Nat. Cancer Inst.*, Oct. 4, 2000, 92(19):1573-1581.
Mandler et al., "Modifications in synthesis strategy improve the yield and efficacy of geldanamycin-herceptin immunoconjugates," *Bioconjugate Chem.*, Jul.-Aug. 2002, 13(4):786-791.

(56) References Cited

OTHER PUBLICATIONS

Mandler et al., "Synthesis and evaluation of antiproliferative activity of a geldanamycin-Herceptin™ immunoconjugate," *Bioorganic & Med. Chem. Letters*, May 15, 2000, 10(10):1025-1028.

Månsson et al., "Characterization of new gangliosides of the lactotetraose series in murine xenografts of a human glioma cell line," *FEBS Lett.*, May 26, 1986, 201(1):109-113.

Marasco et al., "Design, intracellular expression, and activity of a human anti-human immunodeficiency virus type 1 gp120 single-chain antibody," *Proc. Natl. Acad. Sci. U.S.A.*, Aug. 15, 1993, 90(16):7889-7893.

Marasco, "Intrabodies: turning the humoral immune system outside in for intracellular immunization," *Gene Therapy*, Jan. 1997, 4(1):11-15.

Marks et al., "By-passing immunization. Human antibodies from V-gene libraries displayed on phage," *J. Mol. Biol.*, Dec. 5, 1991, 222(3):581-597.

Marks et al., "By-passing immunization: Building high affinity human antibodies by chain shuffling," *Nature Biotechnology*, Jul. 1992, 10(7):779-783.

Mather et al., "Culture of testicular cells in hormone-supplemented serum-free medium," *Annals N.Y. Acad. Sci.*, 1982, 383:44-68.

Mather, "Establishment and characterization of two distinct mouse testicular epithelial cell lines," *Biol. Reprod.*, Aug. 1980, 23(1):243-252.

Matsuda et al., "Structure and physical map of 64 variable segments in the 3' 0.8-megabase region of the human immunoglobulin heavy-chain locus," *Nature Genet.*, Jan. 1993, 3(1):88-94.

McCafferty et al., "Phage antibodies: Filamentous phage displaying antibody variable domains," *Nature*, Dec. 6, 1990, 348:552-554.

McKimm-Breschkin, J. et al., "Neuraminidase Sequence Analysis and Susceptibilities of Influenza Virus Clinical Isolates to Zanamivir and Oseltamivir," Antimicrobial Agents and Chemotherapy, vol. 47, No. 7, Jul. 2003, in 10 pages.

Meezan et al., "Comparative studies on the carbohydrate-containing membrane components of normal and virus-transformed mouse fibroblasts: II: Separation of glycoproteins and glycopeptides by Sephadex chromatography," *Biochemistry*, Jun. 1969, 8(6):2518-2524.

Meyer, "Malignant gliomas in adults," *N. Engl. J. Med.*, Oct. 23, 2008, 359(17): 1850.

Mimura et al., "Role of oligosaccharide residues of IgG1-Fc in FcγRIIb binding," *J. Biol. Chem.*, Dec. 7, 2001, 276(49):45539-45547.

Mishima et al., "Growth suppression of intracranial xenografted glioblastomas overexpressing mutant epidermal growth factor receptors by systemic administration of monoclonal antibody (mAb) 806, a novel monoclonal antibody directed to the receptor," *Cancer Res.*, Jul. 15, 2001, 61(14):5349-5354.

Morelle, W. et al., "The Mass Spectrometric Analysis of Glycoproteins and their Glycan Stuructures", *Review in Current Analytical Chemistry*, vol. 1, No. 1 (2005), pp. 29-57.

Mori K, et al., "Non-fucosylated therapeutic antibodies: the next generation of therapeutic antibodies" *Cytotechnology.* Dec. 2007;55(2-3):109-14. Epub Oct. 31, 2007.

Morimoto et al., "Single-step purification of F(ab')₂ fragments of mouse monoclonal antibodies (immunoglobulins G1) by hydrophobic interaction high performance liquid chromatography using TSKgel Phenyl-5PW," *J. Biochem. Biophys. Meth.*, Mar. 1992, 24(1-2):107-117.

Morrison et al., "Chimeric human antibody molecules: mouse antigen-binding domains with human constant region domains," *Proc. Natl. Acad. Sci. U.S.A.*, Nov. 1984, 81(21):6851-6855.

Morrison, "Immunology. Success in specification," *Nature*, Apr. 28, 1994, 368(6474):812-813.

Munson et al., "Ligand: a versatile computerized approach for characterization of ligand-binding systems," *Anal. Biochem.*, Sep. 1, 1980, 107(1):220-239.

Neuberger et al., "Recombinant antibodies possessing novel effector functions," *Nature*, Dec. 13-19, 1984, 312(5995):604-608.

Neuberger, "Generating high-avidity human Mabs in mice," *Nature Biotechnol.*, Jul. 1996, 14(7):826.

Nicolaou et al., "Calicheamicin $\Theta^I_1$: A rationally designed molecule with extremely potent and selective DNA cleaving properties and apoptosis inducing activity," *Angew. Chem. Intl. Ed. Engl.*, Feb. 1, 1994, 33(2):183-186.

Niculescu-Duvaz et al., "Antibody-directed enzyme prodrug therapy (ADEPT): A review," *Adv. Drg. Del. Rev.*, Jul. 7, 1997, 26(2-3):151-172.

Noto et al., "CD44 and SSEA-4 positive cells in an oral cancer cell line HSC-4 possess cancer stem-like cell characteristics," *Oral Oncol.*, Aug. 2013, 49(8):787-795.

Orlandi et al., "Cloning immunoglobulin variable domains for expression by the polymerase chain reaction," *Proc. Natl. Acad. Sci. U.S.A.*, May 1989, 86(10):3833-3837.

Ørum et al., "Efficient method for constructing comprehensive murine Fab antibody libraries displayed on phage." *Nucleic Acids Res.*, Sep. 25, 1993, 21(19):4491-4498.

Papanastassiou et al., "The potential for efficacy of the modified (ICP 34.5') herpes simplex virus HSV1716 following intratumoural injection into human malignant glioma: a proof of principle study," *Gene Therapy*, Mar. 2002, 9(6):398-406.

Pearlman et al., *Peptide and Protein Drug Delivery, Chapter 6: Analysis of Protein Drugs*, Lee, ed., 1991, pp. 247-301, Marcel Dekker Publishing, New York.

Peipp et al., "Antibody fucosylation differentially impacts cytotoxicity mediated by NK and PMN effector cells," *Blood*, 2008, 112(6):2390-2399.

Plückthun, "Mono- and bivalent antibody fragments produced in *Escherichia coli*: Engineering, folding and antigen binding," *Immunol. Rev.*, Dec. 1992, 130:151-188.

Plückthun, *Handbook of Experimental Pharmacology*, vol. 113: *The Pharacology of Monoclonal Antibodies, Chapter 11: Antibodies from Escherichia coli*, Rosenberg et al., eds., 1994, pp. 269-315, Springer-Verlag, Berlin.

Presta et al., "Humanization of an antibody directed against IgE," *J. Immunol.*, Sep. 1, 1993, 151(5):2623-2632.

Presta et al., "Humanization of an anti-vascular endothelial growth factor monoclonal antibody for the therapy of solid tumors and other disorders," *Cancer Res.*, Oct. 15, 1997, 57(20):4593-4599.

Presta, "Antibody engineering," *Curr. Opin. Biotechnol.*, Aug. 1992, 3(4):394-398.

Presta, "Antibody engineering," *Curr. Opin. Struct. Biol.*, Aug. 1992, 2(4):593-596.

Proba et al., "Functional antibody single-chain fragments from the cytoplasm of *Escherichia coli*: influence of thioredoxin reductase (TrxB)," *Gene*, Jul. 4, 1995, 159(2):203-207.

Puigbò P, Guzmán E, Romeu A, Garcia-Vallvé S. Optimizer: a web server for optimizing the codon usage of DNA sequences. *Nucleic Acids Res.* Jul. 2007;35(Web Server issue):W126-31. Epub Apr. 16, 2007.

Ramm et al., "The periplasmic *Escherichia coli* peptidylprolyl cis,trans-isomerase FkpA. II. Isomerase-independent chaperone activity in vitro," *J. Biol. Chem.*, Jun. 2, 2000, 275(22):17106-17113.

Ravetch et al., "Divergent roles for Fc receptors and complement in vivo," *Ann. Rev. Immunol.*, 1998, 16:421-432.

Ravetch et al., "Fc receptors," *Annu. Rev. Immunol.*, 1991, 9:457-492.

Reyes et al., "Expression of human β-interferon cDNA under the control of a thymidine kinase promoter from herpes simplex virus," *Nature*, Jun. 17, 1982, 297(5867):598-601.

Riechmann et al., "Reshaping human antibodies for therapy," *Nature*, Mar. 24, 1988, 332(6162):323-327.

Roguska et al., "Humanization of murine monoclonal antibodies through variable domain resurfacing," *Proc. Natl. Acad. Sci. U.S.A.*, Feb. 1, 1994, 91(3):969-973.

Roos et al., "Specific inhibition of the classical complement pathway by C1q-binding peptides," *J. Immunol.*, Dec. 15, 2001, 167(12):7052-7059.

Rowland et al, "Drug localisation and growth inhibition studies of vindesine-monoclonal anti-CEA conjugates in a human tumour xenograft," *Cancer Immunol. Immunother.*, 1986, 21(3):183-187.

Ruiz et al., "IMGT, the international ImMunoGeneTics database," *Nucl. Acids Res.*, Jan. 1, 2000, 28(1):219-221.

(56) References Cited

OTHER PUBLICATIONS

Saito et al., "Expression of globo-series gangliosides in human renal cell carcinoma," *Jpn. J. Cancer Res.*, Jul. 1997, 88(7):652-659.
Saito et al., "Human α2,3-sialyltransferase (ST3Gal II) is a stage-specific embryonic antigen-4 synthase," *J. Biol. Chem.*, Jul. 18, 2003, 278(29):26474-26479.
Sastry et al., "Cloning of the immunological repertoire in *Escherichia coli* for generation of monoclonal catalytic antibodies: construction of a heavy chain variable region-specific cDNA library," *Proc. Natl. Acad. Sci. U.S.A.*, Aug. 1989, 86(15):5728-5732.
Schenkel-Brunner, *Human Blood Groups, Chapter 8: P System*, 1995, pp. 211-234, Springer-Verlag, Vienna.
Schier et al., "Identification of functional and structural amino-acid residues by parsimonious mutagenesis," *Gene*, Mar. 9, 1996, 169(2):147-155.
Sell, "Cancer-associated carbohydrates identified by monoclonal antibodies," *Hum. Pathol.*, Oct. 1990, 21(10):1003-1019.
Shalaby et al., "Development of humanized bispecific antibodies reactive with cytotoxic lymphocytes and tumor cells overexpressing the HER2 protooncogene," *J. Exp. Med.*, Jan. 1, 1992, 175(1):217-225.
Shields et al., "High resolution mapping of the binding site on human IgG1 for FcγRI, FcγRII, FcγRIII, and FcRn and design of IgG1 variants with improved binding to the FcγR," *J. Biol. Chem.*, Mar. 2, 2001, 276(9):6591-6604.
Shields et al., "Lack of fucose on human IgG1 N-linked oligosaccharide improves binding to human FcγRIII antibody-dependent cellular toxicity," *J. Biol. Chem.*, Jul. 26, 2002, 277(30):26733-26740.
Shinkawa et al., "The absence of fucose but not the presence of galactose or bisecting N-acetylglucosamine of human IgG1 complex-type oligosaccharides shows the critical role of enhancing antibody-dependent cellular cytotoxicity," *J. Biol. Chem.*, Jan. 31, 2003, 278(5):3466-3473.
Sidhu et al., "Phage-displayed antibody libraries of synthetic heavy chain complementarity determining regions," *J. Mol. Biol.*, Apr. 23, 2004, 338(2):299-310.
Siebenlist et al., "*E. coli* RNA polymerase interacts homologously with two different promoters," *Cell*, Jun. 1980, 20(2):269-281.
Simmons et al., "Expression of full-length immunoglobulins in *Escherichia coli*: Rapid and efficient production of aglycosylated antibodies," *J. Immunol. Methods*, May 1, 2002, 263(1-2):133-147.
Sims et al., "A humanized CD18 antibody can block function without cell destruction," *J. Immunol.*, Aug. 15, 1993, 151(4):2296-2308.
Skerra, "Bacterial expression of immunoglobulin fragments," *Curr. Opinion in Immunol.*, Apr. 1993, 5(2):256-262.
Slamon DJ, et al., "Human breast cancer: correlation of relapse and survival with amplification of the HER-2/neu oncogene" *Science*. Jan. 9, 1987; 235(4785):177-82.
Smith RA et al., "The active form of tumor necrosis factor is a trimer" *J Biol Chem*. May 25, 1987;262(15):6951-4.
Smyth MJ, et al., "CD4+CD25+ T regulatory cells suppress NK cell-mediated immunotherapy of cancer" *J Immunol*. Feb. 1, 2006;176(3):1582-7.
Suresh et al., "Bispecific monoclonal antibodies from hybrid hybridomas," *Methods in Enzymology*, 1986, 121:210-228.
Suzuki E, et al., "A nonfucosylated anti-HER2 antibody augments antibody-dependent cellular cytotoxicity in breast cancer patients" *Clin Cancer Res*. Mar. 15, 2007;13(6):1875-82.
Svennerholm et al., "Human brain gangliosides: Developmental changes from early fetal stage to advanced age," *Biochim. Biophys. Acta*, Sep. 25, 1989, 1005(2):109-117.
Syrigos et al., "Antibody directed enzyme prodrug therapy (ADEPT): a review of the experimental and clinical considerations," *Anticancer Research*, Jan.-Feb. 1999, 19(1A):605-614.
Takeda et al., "Construction of chimaeric processed immunoglobulin genes containing mouse variable and human constant region sequences," *Nature*, Apr. 4-10, 1985, 314(6010):452-454.

Taylor-Papadimitriou et al., "Exploiting altered glycosylation patterns in cancer: Progress and challenges in diagnosis and therapy," *Trends Biotechnol.*, Jun. 1994, 12(6):227-233.
Thorpe, (1985) "Antibody Carriers of Cytotoxic Agents in Cancer Therapy: A Review," in *Monoclonal Antibodies '84: Biological and Clinical Applications*, A. Pinchera et al. (ed.s), pp. 475-506.
Tomlinson et al., "The repertoire of human germline $V_H$ sequences reveals about fifty groups of $V_H$ segments with different hypervariable loops," *J. Mol. Biol.*, Oct. 5, 1992, 227(3):776-798.
Traunecker et al., "Bispecific single chain molecules (Janusins) target cytotoxic lymphocytes on HIV infected cells," *EMBO J.*, Dec. 1991, 10(12):3655-3659.
Traylor et al., "Gangliosides of human cerebral astrocytomas," *J. Neurochem.*, Jan. 1980, 34(1):126-131.
Tsai Ti, et al., "Effective sugar nucleotide regeneration for the large-scale enzymatic synthesis of Globo H and SSEA4" *J Am Chem Soc*. Oct. 2, 2013;135(39):14831-9, Epub Sep. 17, 2013.
Tutt et al., "Trispecific F(ab')₃ derivatives that use cooperative signaling via the TCR/CD3 complex and CD2 to activate and redirect resting cytotoxic T cells," *J. Immunol.*, Jul. 1, 1991, 147(1):60-69.
Tyagarajan K et al., "Exoglycosidase purity and linkage specificity: assessment using oligosaccharide substrates and high-pH anion-exchange chromatography with pulsed amperometric detection" *Glycobiology*. Jan. 1996;6(1):83-93.
Urlaub et al., "Isolation of Chinese hamster cell mutants deficient in dihydrofolate reductase activity." *Proc. Natl. Acad. Sci. U.S.A.*, Jul. 1980, 77(7):4216-4220.
Valentine MA, et al., "Phosphorylation of the CD20 phosphoprotein in resting B lymphocytes. Regulation by protein kinase C" *J Biol Chem*. Jul. 5, 1989;264(19):11282-7.
van Beek et al., "Increased sialic acid density in surface glycoprotein of transformed and malignant cells—a general phenomenon?" *Cancer Res.*, Nov. 1973, 33(11):2913-2922.
Van Meir et al., "Exciting new advances in neuro-oncology: the avenue to a cure for malignant glioma," *CA Cancer J. Clin.*, May-Jun. 2010, 60(3):166-193.
Van Slambrouck et al., "Clustering of monosialyl-Gb5 initiates downstream signalling events leading to invasion of MCF-7 breast cancer cells," *Biochem. J.*, Feb. 1, 2007, 401(3):689-699.
Vaswani et al., "Humanized antibodies as potential therapeutic drugs," *Ann. Allergy, Asthma Immunol.*, Aug. 1998, 81(2):105-116, 119.
Verhoeyen et al., "Reshaping human antibodies: grafting an antilysozyme activity," *Science*, Mar. 25, 1988, 239(4847):1534-1536.
Vermeer Aw et al., "The thermal stability of immunoglobulin: unfolding and aggregation of a multi-domain protein" *Biophys J*. Jan. 2000;78(1):394-404.
Wang et al., "Glycan microarray of Globo H and related structures for quantitative analysis of breast cancer," *Proc. Natl. Acad. Sci. U.S.A.*, Aug. 19, 2008, 105(33):11661-11666.
Ward et al., "Binding activities of a repertoire of single immunoglobulin variable domains secreted from *Escherichia coli*," *Nature*, Oct. 12, 1989, 341(6242):544-546.
Waterhouse et al., "Combinatorial infection and in vivo recombination: a strategy for making large phage antibody repertoires," *Nuc. Acids Res.*, May 11, 1993, 21(9):2265-2266.
Wikstrand et al., "Monoclonal antibody therapy of human gliomas: Current status and future approaches," *Cancer Metastasis Rev.*, 1999, 18(4):451-464.
Williams et al., "Cloning and sequencing of human immunoglobulin V lambda gene segments." *Eur. J. Immunol.*, Jul. 1993, 23(7):1456-1461.
Winter et al., "Making antibodies by phage display technology," *Annu. Rev. Immunol.*, 1994, 12:433-455.
Woof et al., "Human antibody-Fc receptor interactions illuminated by crystal structures," *Nat. Rev. Immunol.*, Feb. 2004, 4(2):89-99.
Yansura et al., "Nucleotide sequence selection for increased expression of heterologous genes in *Escherichia coli*," *Methods: A Companion to Methods in Enzymol.*, Aug. 1992, 4(2):151-158.
Ye et al., "Stage-specific embryonic antigen 4 expression in epithelial ovarian carcinoma," *Int. J. Gynecol. Cancer*, Aug. 2010, 20(6):958-964.

(56) References Cited

OTHER PUBLICATIONS

Yelton et al., "Affinity maturation of the BR96 anti-carcinoma antibody by codon-based mutagenesis." *J. Immunol.*, Aug. 15, 1995, 155(4):1994-2004.

Yu et al., "Anti-GD2 antibody with GM-CSF, interleukin-2, and isotretinoin for neuroblastoma," *N. Engl. J. Med.*, Sep. 30, 2010, 363(14):1324-1334.

Zapata et al., "Engineering linear F(ab')$_2$ fragments for efficient production in *Escherichia coli* and enhanced antiproliferative activity," *Protein Eng.*, Oct. 1995, 8(10):1057-1062.

Zarei et al., "Separation and identification of GM1b pathway Neu5Ac- and Neu5Gc gangliosides by on-line nanoHPLC-QToF MS and tandem MS: toward glycolipidomics screening of animal cell lines," *Glycobiology*, Jan. 2010, 20(1):118-126.

Zhang et al., "Selection of tumor antigens as targets for immune attack using immunohistochemistry: I. Focus on gangliosides," *Int. J. Cancer*, Sep. 26, 1997, 73(1):42-49.

European Search Report issued in connection with corresponding European Patent Application No. 15181446.4, Dec. 7, 2015, 10 pages.

International Search Report and Written Opinion issued for International application No. PCT/US2015/032738, Oct. 20, 2015, 15 pages.

International Search Report and Written Opinion issued for International application No. PCT/US2015/032744, Oct. 2, 2015, 12 pages.

International Search Report and Written Opinion issued for International application No. PCT/US2015/032740, Oct. 26, 2015, 13 pages.

International Search Report and Written Opinion issued for International application No. PCT/US2015/032737, Oct. 1, 2015, 13 pages.

International Search Report and Written Opinion issued for International application No. PCT/US2015/032745, Oct. 8, 2015, 13 pages.

International Search Report issued for International application No. PCT/US2015/049014, Dec. 14, 2015, 3 pages.

\* cited by examiner

SEQUENCE LISTING

```
<160> NUMBER OF SEQ ID NOS: 4

<210> SEQ ID NO 1
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
tggtcagcaa gtgcwtgcca tg                                          22

<210> SEQ ID NO 2
<211> LENGTH: 21
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 2
gacactggac cacaactgcc t                                              21

<210> SEQ ID NO 3
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
gctggacgct cccaactacc actacgagga gtg                                 33

<210> SEQ ID NO 4
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
gtagttggga gcgtccagct ccacggac                                       28
```

ZANAMIVIR PHOSPHONATE CONGENERS WITH ANTI-INFLUENZA ACTIVITY AND DETERMINING OSELTAMIVIR SUSCEPTIBILITY OF INFLUENZA VIRUSES

CROSS-REFERENCE TO RELATED APPLICATIONS

This application is a U.S. national stage filing under section 371 of International Patent Application Serial No. PCT/US2011/035982, filed May 10, 2011 and which claims priority of U.S. Provisional Patent Application Ser. No. 61/333,137, filed May 10, 2010 and titled "Compositions and Methods for Determining Oseltamivir Susceptibility of Influenza Viruses," the contents of which are incorporated herein in their entirety by reference.

SEQUENCE LISTING

The instant application contains a Sequence Listing which has been submitted electronically in ASCII format and is hereby incorporated by reference in its entirety. Said ASCII copy, created on Jul. 17, 2015, is named G2112-01501_SL.txt and is 1,376 bytes in size.

TECHNICAL FIELD OF THE INVENTION

The invention relates to novel compounds that are effective against influenza virus. The invention relates to novel phosphonate compounds that inhibit influenza virus neuraminidase from wild-type and oseltamivir-resistant strains of H1N1, H5N1 and H3N2 influenza viruses. The invention relates to detection of drug resistant pathogens. In particular, the invention relates to the detection of ostelamivir-resistant influenza viruses. More particularly, the invention relates to the detection of ostelamivir-resistant influenza viruses using novel compounds disclosed in the present invention.

BACKGROUND OF THE INVENTION

Outbreaks of influenza A virus continue to cause widespread morbidity and mortality worldwide. In the United States alone, an estimated 5 to 20% of the population is infected by influenza A virus annually, causing approximately 200,000 hospitalizations and 36,000 deaths. The establishment of comprehensive vaccination policies has been an effective measure to limit influenza morbidity. However, the frequent genetic drifting of the virus requires yearly reformulation of the vaccine, potentially leading to a mismatch between the viral strain present in the vaccine and that circulating.

Influenza A virus consists of 9 structural proteins and codes additionally for two nonstructural NS1 proteins with regulatory functions. The segmented nature of the viral genome allows the mechanism of genetic reassortment (exchange of genome segments) to take place during mixed infection of a cell with different viral strains. The influenza A virus is classified into various subtypes depending on the different hemagglutinin (HA) and neuraminidase (NA) viral proteins displayed on their surface. Influenza A virus subtypes are identified by two viral surface glycoproteins, hemagglutinin (HA or H) and neuraminidase (NA or N). Each influenza virus subtype is identified by its combination of H and N proteins. There are 16 known HA subtypes and 9 known NA subtypes.

Influenza virus is a negative-sense segmented RNA virus that can infect many animal species including human. The replication of influenza genome by the viral coded RNA dependent RNA polymerase is an error prone process generating progenies with varied genetic sequences at all times. Viable viruses with genetic alterations are designated "antigenic drift" mutants. The segmented nature of the viral genome and the possibility to infect different animal species could produce "antigenic shift" mutants (P. K. Cheng et al., Emerg. Infect. Dis. 15, 966 (2009)). Under desirable conditions, dominant variants may become prominent pathogens for human or animals. The multi-step selection processes leading to mutant evolution are not completely understood (L. Cohen-Daniel et al., J. Clin. Virol. 44, 138 (2009); R. Wagner, M. Matrosovich, H. D. Klenk, Rev. Med. Virol. 12, 159 (2002)). Whereas vaccines are often used for the prevention of influenza virus infections, the most useful therapies for the treatment of influenza infections involve administration of Tamiflu® (the phosphate salt of oseltamivir ethyl ester, Roche Laboratories, Inc.) and Relenza® (zanamivir, Glaxo Wellcome, Inc.). (N. J. Cox, J. M. Hughes, N. Engl. J. Med. 341, 1387 (1999)). Oseltamivir and zanamivir are viral sialidase (neuraminidase) inhibitors that prevent the release and dispersal of progeny virions within the mucosal secretions and thereby reduce viral infectivity. Neuraminidase (NA), a glycoprotein expressed on the influenza virus surface, is essential for virus replication and infectivity by breaking the linkage between the progeny virus from the surface sialo-receptor of host cells. Thus, inhibition of NA by the structure-based strategy has been applied in discovery of anti-influenza drugs.

Zanamivir (Relenza™) (von Itzstein, M. et al. Nature 1993, 363, 418. Dunn, C. J.; Goa, K. L. Drugs 1999, 58, 761.) is a popular drug for the treatment of influenza. Tamiflu is a prodrug that is readily hydrolyzed by hepatic esterases to give the corresponding oseltamivir carboxylic acid as the active inhibitor to interact with three arginine residues (Arg118, Arg292 and Arg371) in the active site of viral neuraminidase (NA). (von Itzstein, M. et al. Nature 1993, 363, 418. Lew, W. et al. Curr. Med. Chem. 2000, 7, 663. Russell, R. J. et al. Nature 2006, 443, 45.) Both oseltamivir and zanamivir inhibit influenza virus NA that is essential for virus propagation by cleaving the linkage between the progeny virus from the surface sialo-receptor of host cells. The NA inhibitors are designed to have (oxa)cyclohexene scaffolds to mimic the oxonium transition-state in the enzymatic cleavage of sialic acid (N-acetylneuraminic acid), the outmost saccharide on the cell surface glycoprotein for binding with the active site of viral NA. To accommodate the binding with oseltamivir carboxylic acid, an induced fit of the NA to create a large hydrophobic pocket is needed for the 3-pentyl side chain. (Collins, P. J., et al. Nature 2008, 453, 1258.) In comparison, zanamivir is less susceptible to the newly evolved resistant viruses than oseltamivir phosphate. In the absence of the need for generating the hydrophobic binding pocket, the inhibition potency of zanamivir to the NA mutant (e.g. the clinically relevant H274Y mutant) is unchanged.

Influenza A (H1N1) viruses bear a oseltamivir resistance conferring amino acid change of histidine to tyrosine at position 274 (H274Y) of the neuraminidase (NA) protein. The 2008 surge of the oseltamivir resistant H274Y mutants in seasonal H1N1 (A. Moscona, N. Engl. J. Med. 360, 953 (2009)) was puzzling because the increases of these mutations are not correlated to oseltamivir usage in many of the H274Y prevalent areas (J. Mossong et al., Antiviral Res. 84, 91 (2009); M. Jonges et al., Antiviral Res. 83, 290 (2009)). In addition, the H274Y oseltamivir resistant pandemic H1N1 (A. Gulland, Br. Med. J. 339, b4975 (2009)) and the H5N1 mutants (Q. M. Le et al., Nature 437, 1108 (2005)) are reported in patients suggesting that these mutants could impact influenza therapy options (I. Stephenson et al., *Clin. Infect. Dis.* 48, 389 (2009)).

Many derivatives of zanamivir have been prepared by modification at the glyceryl moiety scaffolds to mimic the oxonium transition-state in the enzymatic cleavage of sialic acid. The phosphonate group is generally used as a bioisostere of carboxylate in drug design. (White, C. L. et al. *J. Mol. Biol.* 1995, 245, 623. Schug, K. A.; Lindner, W. *Chem. Rev.* 2005, 105, 67. Streicher, H.; Busseb, H. *Bioorg. Med. Chem.* 2006, 14, 1047.) In comparison with the carboxylate-guanidinium ion-pair, a phosphonate ion will exhibit stronger electrostatic interactions with the guanidinium ion. Thus, the zanamivir phosphonate congener is expected to have more potent against the neuraminidases of H1N1 and H5N1 viruses, even the H274Y mutant. The enhanced affinity may be attributable to the strong electrostatic interactions of the phosphonate group with the three arginine residues (Arg118, Arg292 and Arg371) in physiological conditions.

Solution-phase neuraminidase inhibition assays normally use the fluorogenic substrate, 2'-(4-methylumbelliferyl)-.alpha.-D-acetyl-neuraminic acid, which is cleaved by neuraminidase to yield a fluorescent product that can be quantified using a fluorometer (Potier et al., Anal. Biochem. 94:287-296 (1979)), however, this assay method is not amenable to a high-throughput format. In addition, due to the fast emergence of resistant viral strains (see McKimm-Breschkin, J. L. Antiviral Res. 2000, 47, 1-17), there remains a need to find new influenza neuraminidase inhibitors.

SUMMARY OF THE INVENTION

The worldwide surge of oseltamivir resistant H1N1 influenza viruses in 2008 has prompted the survey for resistant mutants and the need for development of quick tests for oseltamivir susceptibility. In the midst of the potentially prevalent oseltamivir resistant H1N1 viruses, there is a need for a "point-of-care" test for quick assessment of the oseltamivir susceptibility of a patient's specimens in a doctor's office that will benefit decisions regarding treatment options.

Novel phosphonate compounds are described. The compounds have activity as neuraminidase inhibitors against wild-type and oseltamivir-resistant strains of H1N1, H5N1 and H3N2 influenza viruses. In some embodiments, the oseltamivir-resistant influenza strain comprises a H274Y mutation in neuraminidase. The present disclosure also provides an enantioselective synthetic route to the novel phosphonate compounds via sialic acid.

According to a feature of the present disclosure, a compound according to formula (I) is disclosed (I)

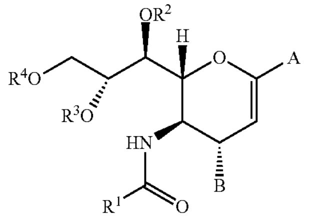

wherein A is PO(OR)(OR5), wherein R and $R^5$ are independently selected from H, C1-C10 alkyl, aryl, aralkyl and X, wherein X is a cationic counterion selected from the group consisting of ammonium, methyl ammonium, dimethylammonium, trimethylammonium, tetramethylammonium, ethanol-ammonium, dicyclohexylammonium, guanidinium, ethylenediammonium cation, lithium cation, sodium cation, potassium cation, cesium cation, beryllium cation, magnesium cation, calcium cation, and zinc cation, wherein B is $NHR^6$, $NH_3^+Y^-$, $R^6N(C{=}NH)NH_2$ or $R^6N(C{=}NH_2^+)NH_2Y^-$, wherein $R^6$ represents hydrogen, C1-C10 alkyl, aryl, or aralkyl, wherein Y− is a anionic counterion selected from the group consisting of chloride, bromide, iodide, acetate, trifluoroacetate, phosphate, diphosphate, nitrate, sulfate, benzenesulfonate, benzoate, salicylate, hydroxynaphthoate, fumarate, maleate, lactate, malate, succinate, tartrate, citrate, glutamate, gluconate, and stearate, wherein $R^1$ is $CH_3$ or $CF_3$; wherein $R^2$ is H, C1-C10 alkyl or $O{=}C{-}NHR^7$, wherein $R^7$ represents a linker annexed with functional moiety such as biotin, fluorophore and anti-inflammatory agents, and wherein $R^3$ and $R^4$ are independently hydrogen, C1-C10 alkyl or $O{=}C{-}R^8$, where $R^8$ represents C1-C10 alkyl, aryl, or aralkyl.

A composition is disclosed comprising a therapeutically effective amount of formula (I) and a pharmaceutically acceptable excipient, wherein the composition is designed to be administered to an organism to inhibit the activity of influenza virus neuraminidase.

According to a feature of the invention, a composition is disclosed comprising a therapeutically effective amount of at least one of:

(1a)

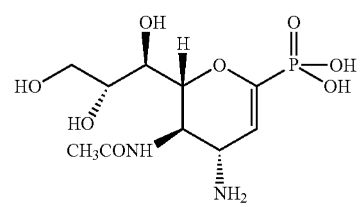

and (1b)

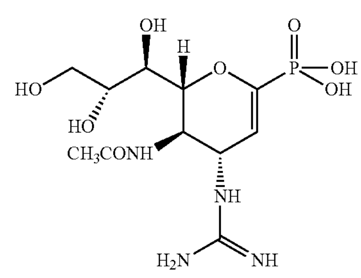

or at least one of:

(1c)

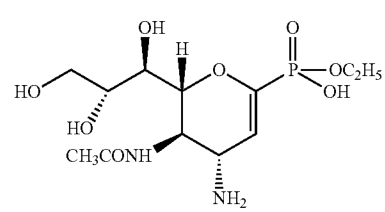

and

-continued

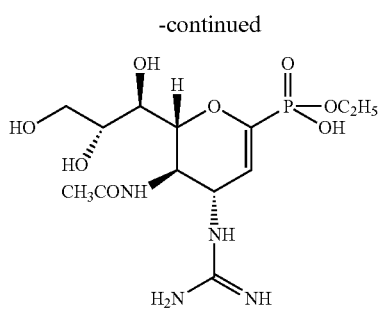
(1d)

or at least one of:

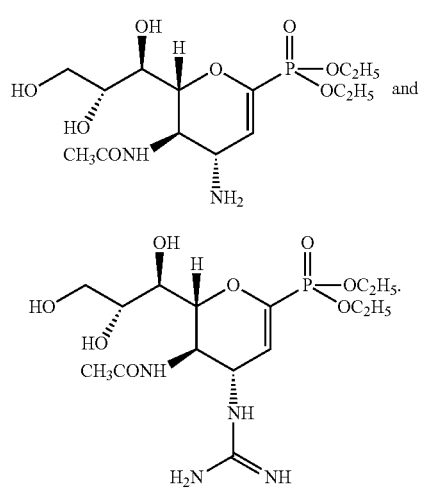
(1e)

(1f)

According to a feature of the present disclosure, a process is disclosed for making a composition of formula I the process comprising the steps of:

(a) acetylating a chiral precursor sialic acid (2) to prepare an intermediate compound (3).

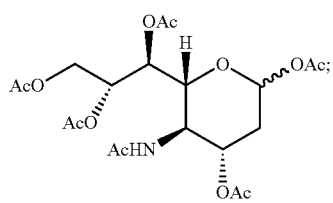
(3)

(b) treating intermediate compound (3) with diethyl trimethylsilyl phosphite to form intermediate compound (4):

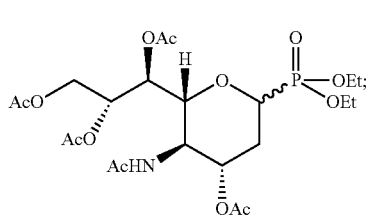
(4)

(c) treating intermediate (4) with N-bromosuccinimide under light irradiation to give a bromo-substituted compound, which forms intermediate (5) in pyridine:

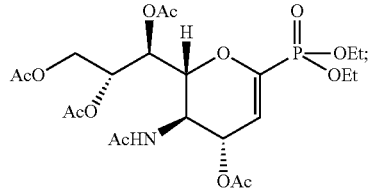
(5)

(d) treating intermediate compound (5) with trimethylsilyl trifluorosulfonate to form intermediate compound (6):

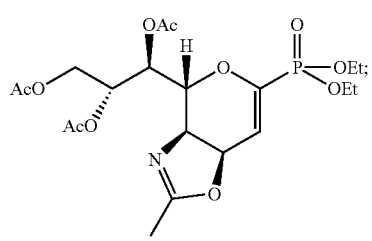
(6)

and (e) treating intermediate compound (6) with trimethylsilyl azide to form intermediate compound (7):

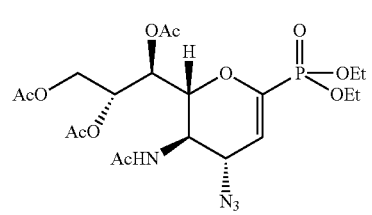
(7)

In some embodiments, the process further comprises treating intermediate compound (7) with bromotrimethylsilane, with sodium methoxide and then hydrogenating in sequence, to form compound (1a):

(1a)

In some embodiments, the process further comprises treating intermediate compound (7) with sodium ethoxide and then hydrogenating to form compound (1c):

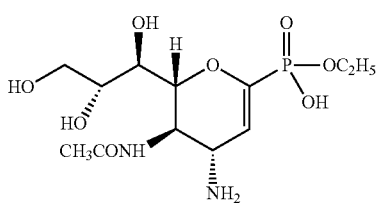
(1c)

In some embodiments, the process further comprises hydrogenating intermediate compound (7), and then reacting with 1,3-bis(tert-butoxycarbonyl)-2-methylthiopseudourea and Et3N to form intermediate compound (8):

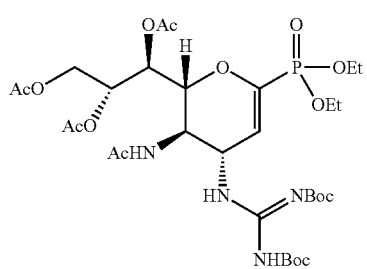
(8)

In some embodiments, the process further comprises treating intermediate compound (8) with bromotrimethylsilane, and then with sodium methoxide to form compound (1b):

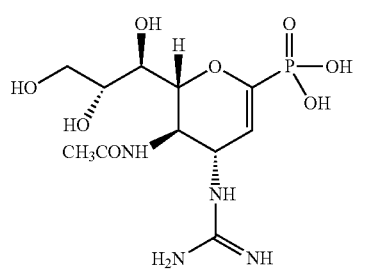
(1b)

In some embodiments, the process further comprises the step of treating intermediate compound (8) with sodium ethoxide and then trifluoroacetic acid to form compound (1d):

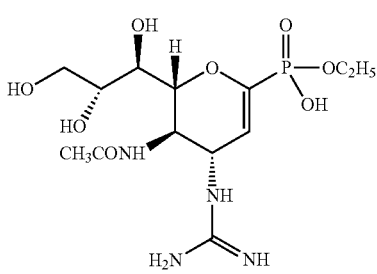
(1d)

In one aspect the invention relates to any product according to formula (I) produced by a process disclosed herein.

According to a feature of the present disclosure, a method is disclosed for treating influenza infection, comprising providing a therapeutically effective amount of a composition according to formula (I) to a subject in need thereof.

According to certain aspects of the invention, the compound according to formula (I) is at least one of:

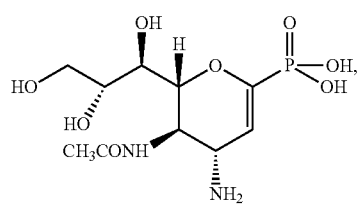
(1a)

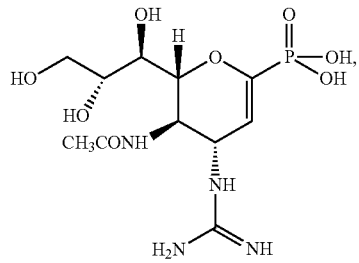
(1b)

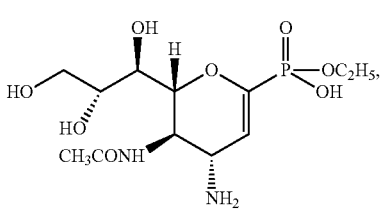
(1c)

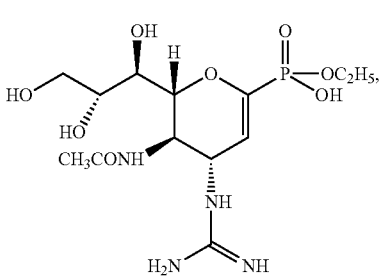
(1d)

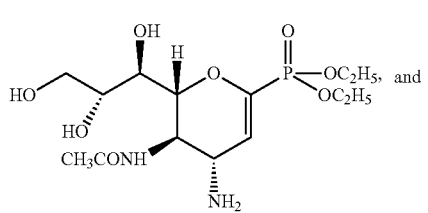
(1e)

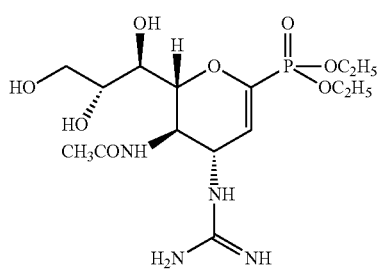
(1f)

Another implementation of the invention provides a method of inhibiting the activity of a neuraminidase comprising contacting said neuraminidase with of any one of compounds (I). In one aspect, the neuraminidase is an influenza neuraminidase and the activity is inhibited in vivo. In another aspect, the activity is inhibited in vitro.

The invention relates to determining the drug susceptibility of a pathogen by measuring binding of the drug and competitive inhibitors thereof.

The invention relates to a method for determining the presence of oseltamivir-resistant influenza virus, the method comprising the steps of: (a) providing a sample suspected of comprising an oseltamivir-resistant influenza-virus or virus particle; (b) contacting the sample with a binding molecule comprising a influenza neuraminidase recognition unit (R) in the presence and absence of ostelamivir carboxylate (OC); and (c) determining a difference in binding of the binding molecule to the influenza virus, or viral particle, in the presence and absence of oseltamivir, wherein a lack of reduction in binding level by the recognition unit (R) in the presence of oseltamivir as compared to the reduction in the level of binding when contacted with a ostelamivir-sensitive influenza virus control, indicates the presence of an ostelamivir-resistant influenza virus in the sample. The binding of the recognition unit (R) to the influenza virus is competitively inhibited by the concurrent binding by oseltamivir carboxylate.

In some embodiments, the oseltamivir-resistant influenza comprises a mutation at amino acid position 274 of the neuraminidase (NA) protein of influenza. In some embodiments, the mutation is H274Y.

In some aspects, the influenza virus containing sample is selected from the group consisting of mucus, saliva, respiratory secretion, throat wash, nasal wash, spinal fluid, sputum, urine, semen, sweat, feces, plasma, blood, broncheoalveolar fluid, vaginal fluid, tear fluid and tissue biopsy. In some embodiments, the influenza virus is obtained from a cell culture. In some embodiments, the cell culture is a Vero cell culture. In some embodiments, the influenza virus containing sample is a cell infected with influenza virus.

In some aspects, the influenza virus containing sample is immobilized on a solid substrate. The solid substrate may be selected from the group consisting of a microwell, microtiter plates, silicon chips, glass slides, beads, microparticles, films, chromatography paper, membranes, bottles, dishes, slides, blotting material, filters, fibers, woven fibers, shaped polymers, particles, dip-sticks, test tubes, chips, microchips, Langmuir Blodgett film, glass, germanium, silicon, (poly) tetrafluoroethylene, polystyrene, gallium arsenide, gallium phosphide, silicon oxide, silicon nitride, and combinations thereof. In some embodiments, the influenza virus or virus particle is immobilized on the solid substrate via the binding of a carbohydrate receptor to the hemagglutinin component of influenza virus.

In some aspects, the immobilization of the influenza virus or virus particle to the solid substrate does not alter the binding of the binding molecule or oseltamivir carboxylate to neuraminidase component of the influenza virus or particle thereof.

In some embodiments, the recognition unit (R) is selected from zanamivir, or tamiphosphor guanidine monoester, or phosphazanamivir or its monoester, and salts, esters and derivatives thereof. In some embodiments, the recognition unit (R) is coupled to a sensing unit (S) that is detectable. In some embodiments, the recognition unit (R) is coupled to the sensing unit via a linker (L), such that the binding molecule has the structure R-L-S. In some embodiments, the linker (L) reduces the effect of the binding of the recognition unit to the influenza virus to the detection of the sensing unit (S).

The linker (L) may be selected from an aliphatic chain, a triazole, a water-soluble linker, and an ethylene glycol linker.

In some aspects, the sensing unit is directly or indirectly detectable. In some embodiments, the sensing unit is coupled to the detectable moiety by a streptavidin-biotin interaction.

In some aspects, the sensing unit is a detectable moiety selected from a fluorescent label, a gold label, an enzyme label, a radioactive label, a quantum dot label, and a protein label. In some embodiments, the detectable moiety is detected by a signal selected from a luminescent, colorimetric, fluorimetric, or radioactive signal.

In some embodiments, the fluorescent label is selected from the group consisting of fluorescein, BODIPY, Alexa Fluor, Cy3, Cy5, Oregon Green, tetramethylrhodamine, Rhodamine Red, Texas Red, pyridyloxazole, benzoxadiazole derivatives, NBD halides, iodoacetamides, SBD; Lucifer Yellow, iodoacetamide; stilbene, coumarin, naphthalene, aziridine, dapoxyl, pyrene, bimanes, xanthene, cyanine, pyrene, phthalocyanine, phycobiliprotein, squarene dye, energy transfer dye combinations, and derivatives thereof.

In some embodiments, a biotin sensing unit is detectable by fluorescence labeled streptavidin. In some embodiments, a fluorescence sensing unit is selected from fluorescein isothiocyanate (FITC), Alexa dyes and quantum dots. In some embodiments, the biotin sensing unit is detectable by streptavidin conjugated enzymes such as alkalian phosphatase, beta-galactosidase, or horse radish peroxidase. In some embodiments, a tamiphosphor guanidine monoester is an ammonium salt thereof. In some embodiments, a phosphazanamivir is an ammonium salt thereof.

The disclosure relates to a compound that binds to the neuraminidase of an influenza virus or particle thereof, wherein the binding is competitively inhibited by oseltamivir carboxylate (OC), the compound comprising the formula R-L-S, wherein: R is selected from zanamivir, or tamiphosphor guanidine monoester, or phosphazanamivir or its monoester, and salts, esters and derivatives thereof; L is optional, and selected from a triazole linker, an aliphatic linker, or an ethylene glycol linker; and S is selected from (a) a moiety directly detectable by a method selected from fluorescence, colorimety, luminescence and radioactive detection, or (b) an indirectly detectable moiety selected from biotin and streptavidin conjugated reporting systems.

The disclosure relates to diagnostic kits, comprising a packaging material and a composition for detecting presence of an oseltamivir-resistant influenza virus in a sample, wherein said composition comprises a compound according to the disclosure. In some embodiments, the kit further comprises a label or package insert comprising indications or directions for use of the kit for detection of oseltamivir-resistant influenza virus in a sample.

These and other aspects will become apparent from the following description of the preferred embodiment taken in conjunction with the following drawings, although variations and modifications therein may be affected without departing from the spirit and scope of the novel concepts of the disclosure.

BRIEF DESCRIPTION OF THE DRAWINGS

The following drawings form part of the present specification and are included to further demonstrate certain aspects of the present disclosure, the inventions of which can be better understood by reference to one or more of these drawings in combination with the detailed description of specific embodiments presented herein.

FIG. 14 shows RABC assay of immobilized WSN viruses for estimating the OC resistant viral contents by ZB binding with competing OC. Mixed WSN virus samples with varying 274H and 274Y virus contents were immobilized in triplicates each in anti-HA coated microwells at $10^5$ PFU (triangles), $10^4$ PFU (squares), and $10^3$ PFU (circles) per well. They were added with 30 nM ZB and 150 nM OC for one hr followed by coupling with streptavidin conjugated alkaline phosphatase to determine the estimated percent OC resistant values that are plotted against the contents of 274Y used for the experiment.

DETAILED DESCRIPTION OF THE INVENTION

Figure 1:
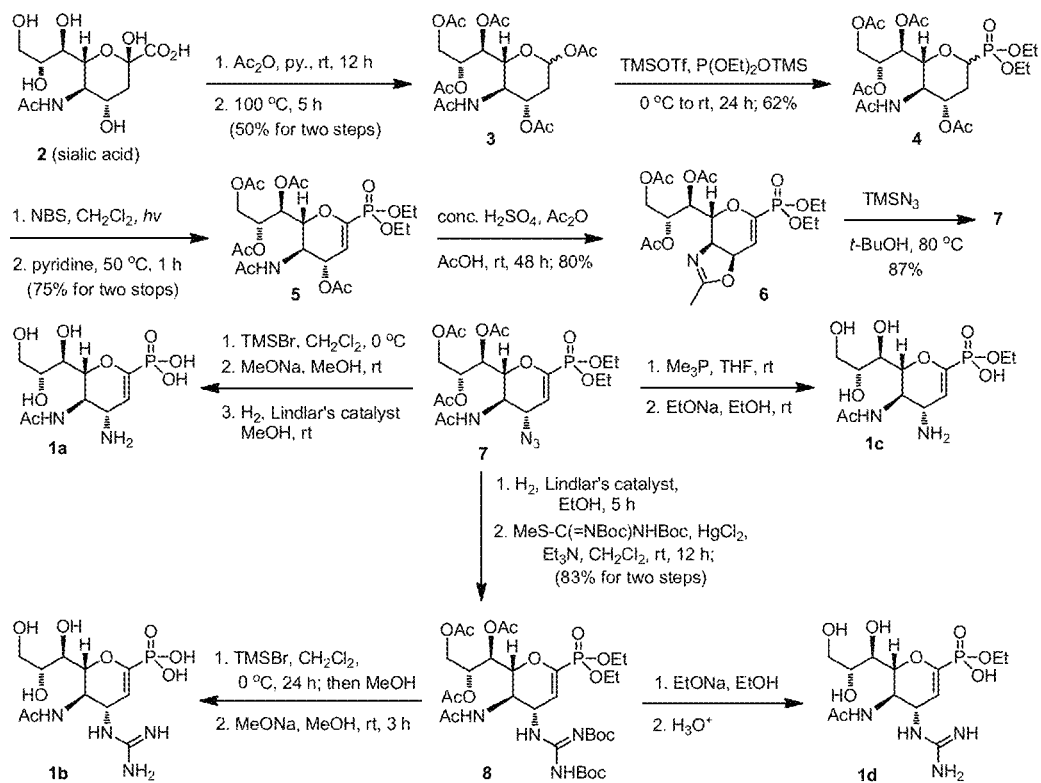
FIG. 1 shows a scheme for the synthesis of zanamivir phosphonate congener and derivatives.

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and in no way limits the scope and meaning of the invention or of any exemplified term. Likewise, the invention is not limited to various embodiments given in this specification.

Unless otherwise defined, all technical and scientific terms used herein have the same meaning as commonly understood by one of ordinary skill in the art to which this invention pertains. In the case of conflict, the present document, including definitions will control.

Oseltamivir is an oral prodrug that is converted by endogenous esterases to oseltamivir carboxylate (OC). Zanamivir works by binding to the active site of the neuraminidase protein, rendering the influenza virus unable to escape its host cell and infect others. (Cyranoski D (September 2005) *Nat. Medicine* 11 (9): 909). It is also an inhibitor of influenza virus replication in vitro and in vivo. Bioavailability of zanamivir is 2% and it is usually administered by inhalation.

Recent reports on the drug resistant avian flu infections and the side effects in children receiving Tamiflu® treatments suggest that new chemical identities for neuraminidase inhibitors (NAIs) are needed for the battle against the threat of the pandemic flu. The NA inhibitors are designed to have (oxa)cyclohexene scaffolds to mimic the oxonium transition-state in the enzymatic cleavage of sialic acid, (Russell et al., Nature 2006, 443:45). On hydrolysis by hepatic esterases, the active carboxylate, oseltamivir is exposed to interact with three arginine residues (Arg118, Arg292 and Arg371) in the active site of NA. (Id.).

Synthesis of Zanamivir Phosphonate Congeners with Anti-Influenza Activity

The present disclosure provides a novel synthetic route to novel phosphonate congers of zanamivir. D-Sialic acid was utilized as a chiral precursor for the synthesis of novel active neuraminidase inhibitors. Novel phosphonate congers exhibit better anti-flu activities than zanamivir and oseltamivir by inhibiting the neuraminidases of the wild-type and H274Y mutant of H1N1 and H5N1 viruses.

In one implementation, the invention provides a novel synthetic method to enantioselective synthesis of various zanamivir phosphonate congeners and the derivatives with reasonably high yields. The synthetic route is shown in FIG. 1. Reagents and steps described in FIG. 1 are as follows:

Step 1. Sialic acid (2) was treated with acetic anhydride in pyridine to afford the peracetylation intermediate, which was heated at 100° C. to induce decarboxylation, giving compound 3. (Horn, E. J., et al Carbohydr. Res. 2008, 343, 936).

Step 2. Compound 3 was treated with trimethylsilyl diethyl phosphate as the appropriate nucleophile to afford the phosphonate compound 4 as a mixture of α and β anomers (2:3), which could be separated by chromatography and characterized by NMR spectral analyses.

Step 3. Phosphonates 4 (as an anomeric mixture) was irradiated with N-bromosuccinimide (NBS) in $CH_2Cl_2$ solution to undergo a radical type bromination, which was treated in situ with pyridine to afford a β-elimination product 5, a phosphonate derivative of Neu5Ac2en (DANA). This synthetic method for 5 was much more efficient than a lengthy procedure reported previously for its analogue of dimethyl phosphonate (Vasella, A.; Wyler, R. Helv. Chim. Acta 1991, 74, 451).

Step 4. In a media of acetic anhydride, acetic acid and concentrated $H_2SO_4$, compound 5 was converted into the oxazoline 6.

Step 5. The regio- and stereoselective ring-opening reaction of oxazoline 6 with azidotrimethylsilane was carried out to afford an azido compound 7 as the pivotal intermediate leading to compounds 1a, 1b, 1c and 1d.

Step 6. Compound 7 was converted to phosphonic acid 1a by a sequence of three reactions: removal of both ethyl groups from phosphonate 7 with bromotrimethylsilane, deacetylation using sodium methoxide in methanol, and selective reduction of the azido group to amine by hydrogenation in the presence of Lindlar catalyst.

Alternatively, only one ethyl group was removed from phosphonate diester 7 on treatment with sodium ethoxide in ethanol, giving phosphonate diester 1c after the subsequent reduction of the azido group.

Step 7. To introduce a guanidino substituent, the azido group in compound 7 was first reduced to give amine, which reacted with 1,3-bis(tert-butoxycarbonyl)-2-methylthiopseudourea in the presence of mercury chloride and triethylamine to afford guanidine compound 8.

Step 8. Both ethyl groups in phosphonate 8 were removed by bromotrimethylsilane, and the concurrent removal of tert-butoxycarbonyl (Boc) groups was realized by workup with methanol due to the in situ generated HBr. The zanamivir phosphonate (1b) was obtained by deacetylation.

Alternatively, phosphonate diester 7 was converted to a monoester with sodium ethoxide, followed by removal of Boc groups with trifluoroacetic acid, to give compound 1d.

The compositions of this invention optionally comprise salts of the compounds herein, especially pharmaceutically acceptable non-toxic salts containing, for example, $Na^+$, $Li^+$, $K^+$, $Ca^{++}$ and $Mg^{++}$. Such salts may include those derived by combination of appropriate cations such as alkali and alkaline earth metal ions or ammonium and quaternary amino ions with an acid anion moiety.

Metal salts are prepared by reacting the metal hydroxide with a compound of this invention. Examples of metal salts which are prepared in this way are salts containing $Na^+$, $Li^+$, $K^+$.

In addition, salts may be formed from acid addition of certain organic and inorganic acids, e.g., HCl, HBr, $H_2SO_4$, or organic sulfonic acids, to basic centers, typically amines. Finally, it is to be understood that the compositions herein comprise compounds of the invention in their un-ionized, as well as zwitterionic form, and combinations with stoichiometric amounts of water as in hydrates. Another aspect of the invention relates to methods of inhibiting the activity of neuraminidase comprising the step of treating a sample suspected of containing neuraminidase with a compound of the invention.

The compounds of this invention are formulated with conventional carriers and excipients, which will be selected in accord with ordinary practice. Tablets will contain excipients, glidants, fillers, binders and the like. Aqueous formulations are prepared in sterile form, and when intended for delivery by other than oral administration generally will be isotonic. All formulations will optionally contain excipients such as those set forth in the "Handbook of Pharmaceutical Excipients" (1986), which is expressly incorporated by reference in its entirety. Excipients include ascorbic acid and other antioxidants, chelating agents such as EDTA, carbohydrates such as dextrin, hydroxyalkylcellulose, hydroxyalkylmethylcellulose, stearic acid and the like. The pH of the formulations ranges from about pH 3 to about pH 11, but is ordinarily about pH 7 to pH 10.

One or more compounds of the invention (herein referred to as the active ingredients) are administered by any route appropriate to the condition to be treated. Suitable routes include oral, rectal, nasal, topical (including buccal and sublingual), vaginal and parenteral (including subcutaneous, intramuscular, intravenous, intradermal, intrathecal and epidural), and the like. It will be appreciated that the preferred route may vary with for example the condition of the recipient.

While it is possible for the active ingredients to be administered alone it may be preferable to present them as pharmaceutical formulations. The formulations, both for veterinary and for human use, of the invention comprise at least one active ingredient, as above defined, together with one or more acceptable carriers therefore and optionally other therapeutic ingredients. The carrier(s) must be "acceptable" in the sense of being compatible with the other ingredients of the formulation and physiologically innocuous to the recipient thereof.

The formulations include those suitable for the foregoing administration routes. The formulations may conveniently be presented in unit dosage form and may be prepared by any of the methods well known in the art of pharmacy. Techniques and formulations generally are found in Remington's Pharmaceutical Sciences (Mack Publishing Co., Easton, Pa.). Such methods include the step of bringing into association the active ingredient with the carrier which constitutes one or more accessory ingredients. In general the formulations are prepared by uniformly and, intimately bringing into association the active ingredient with liquid carriers or finely divided solid carriers or both, and then, if necessary, shaping the product.

Formulations of the invention suitable for oral administration are prepared as discrete units such as capsules, cachets or tablets each containing a predetermined amount of the active ingredient; as a powder or granules; as solution or a suspension in an aqueous liquid or a non-aqueous liquid; or as an oil-in-water liquid emulsion or a water-in-oil liquid emulsion. The active ingredient may also be presented as a bolus, electuary or paste.

A tablet is made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered active ingredient moistened with an inert liquid diluent. The tablets may optionally be coated or scored and optionally are formulated so as to provide slow or controlled release of the active ingredient.

For infections of the eye or other external tissues e.g. mouth and skin, the formulations are preferably applied as a topical ointment or cream containing the active ingredient(s) in an amount of, for example, 0.075 to 20% w/w (including active ingredient(s) in a range between 0.1% and 20% in increments of 0.1% w/w such as 0.6% w/w, 0.7% w/w, etc.), preferably 0.2 to 15% w/w and most preferably 0.5 to 10% w/w. When formulated in an ointment, the active ingredients may be employed with either a paraffinic or a water-miscible ointment base. Alternatively, the active ingredients may be formulated in a cream with an oil-in-water cream base.

If desired, the aqueous phase of the cream base may include, for example, at least 30% w/w of a polyhydric alcohol, i.e. an alcohol having two or more hydroxyl groups such as propylene glycol, butane 1,3-diol, mannitol, sorbitol, glycerol and polyethylene glycol (including PEG 400) and mixtures thereof. The topical formulations may desirably include a compound which enhances absorption or penetration of the active ingredient through the skin or other affected areas. Examples of such dermal penetration enhancers include dimethyl sulphoxide and related analogs.

The oily phase of the emulsions of this invention may be constituted from known ingredients in a known manner. While the phase may comprise merely an emulsifier (otherwise known as an emulgent), it desirably comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations.

Emulgents and emulsion stabilizers suitable for use in the formulation of the invention include Tween™ 60, Span™ 80, cetostearyl alcohol, benzyl alcohol, myristyl alcohol, glyceryl mono-stearate and sodium lauryl sulfate.

The choice of suitable oils or fats for the formulation is based on achieving the desired cosmetic properties. The cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils are used.

Formulations suitable for topical administration to the eye also include eye drops wherein the active ingredient is dissolved or suspended in a suitable carrier, especially an aqueous solvent for the active ingredient. The active ingredient is preferably present in such formulations in a concentration of 0.5 to 20%, advantageously 0.5 to 10% particularly about 1.5% w/w.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for intrapulmonary or nasal administration have a particle size for example in the range of 0.1 to 500 microns (including particle sizes in a range between 0.1 and 500 microns in increments microns such as 0.5, 1, 30 microns, 35 microns, etc.), which is administered by rapid inhalation through the nasal passage or by inhalation through the mouth so as to reach the alveolar sacs. Suitable formulations include aqueous or oily solutions of the active ingredient. Formulations suitable for aerosol or dry powder administration may be prepared according to conventional methods and may be delivered with other therapeutic agents such as compounds heretofore used in the treatment or prophylaxis of influenza A or B infections.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

The formulations are presented in unit-dose or multi-dose containers, for example sealed ampoules and vials, and may be stored in a freeze-dried (lyophilized) condition requiring only the addition of the sterile liquid carrier, for example water for injection, immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

It should be understood that in addition to the ingredients particularly mentioned above the formulations of this invention may include other agents conventional in the art having regard to the type of formulation in question, for example those suitable for oral administration may include flavoring agents.

The invention further provides veterinary compositions comprising at least one active ingredient as above defined together with a veterinary carrier therefor. Veterinary carriers are materials useful for the purpose of administering the composition and may be solid, liquid or gaseous materials which are otherwise inert or acceptable in the veterinary art and are compatible with the active ingredient. These veterinary compositions may be administered orally, parenterally or by any other desired route. Compounds of the invention are used to provide controlled release pharmaceutical formulations containing as active ingredient one or more compounds of the invention ("controlled release formulations") in which the release of the active ingredient are controlled and regulated to allow less frequency dosing or to improve the pharmacokinetic or toxicity profile of a given active ingredient. Effective dose of active ingredient depends at least on the nature of the condition being treated, toxicity, whether the compound is being used prophylactically (lower doses) or against an active influenza infection, the method of delivery, and the pharmaceutical formulation, and will be determined by the clinician using conventional dose escalation studies. It can be expected to be from about 0.0001 to about 100 mg/kg body weight per day. Typically, from about 0.01 to about 10 mg/kg body weight per day. More typically, from about 0.01 to about 5 mg/kg body weight per day. More typically, from about 0.05 to about 0.5 mg/kg body weight per day. For example, for inhalation the daily candidate dose for an adult human of approximately 70 kg body weight will range from 1 mg to 1000 mg, preferably between 5 mg and 500 mg, and may take the form of single or multiple doses.

In one implementation, active ingredients of the invention are also used in combination with other active ingredients. Such combinations are selected based on the condition to be treated, cross-reactivities of ingredients and pharmaco-properties of the combination. For example, when treating viral infections of the respiratory system, in particular influenza infection, the compositions of the invention are combined with antivirals (such as amantidine, rimantadine and ribavirin), mucolytics, expectorants, bronchialdilators, antibiotics, antipyretics, or analgesics. Ordinarily, antibiotics, antipyretics, and analgesics are administered together with the compounds of this invention.

Another implementation of the invention includes in vivo metabolic products of the compounds described herein, to the extent such products are novel and unobvious over the prior art. Such products may result for example from the oxidation, reduction, hydrolysis, amidation, esterification and the like of the administered compound, primarily due to enzymatic processes. Accordingly, the invention includes novel and unobvious compounds produced by a process comprising contacting a compound of this invention with a mammal for a period of time sufficient to yield a metabolic product thereof. Such products typically are identified by preparing a radiolabeled (e.g. $^{14}C$ or $^{3}H$) compound of the invention, administering it parenterally in a detectable dose (e.g. greater than about 0.5 mg/kg) to an animal such as rat, mouse, guinea pig, monkey, or to man, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g. by MS or NMR analysis. In general, analysis of metabolites is done in the same way as conventional drug metabolism studies well-known to those skilled in the art. The conversion products, so long as they are not otherwise found in vivo, are useful in diagnostic assays for therapeutic dosing of the compounds of the invention even if they possess no neuraminidase inhibitory activity of their own.

Prodrugs of the novel phosphonate congeners are contemplated. Both the polar phosphonate and guanidinium groups may be optionally further functionalized by techniques known in the art to enhance pharmacokinetic and/or pharmacodynamic properties. For example, formulation and use of prodrugs, e.g. acyloxymethyl- and aryl phosphonate esters, may be utilized to enhance oral bioavailability (Krise and Stella, *Adv. Drug Deliv. Rev.* 1996, 19, 287).

In one aspect of the invention, samples suspected of containing neuraminidase include natural or man-made materials such as living organisms; tissue or cell cultures; biological samples such as biological material samples (blood, serum, urine, cerebrospinal fluid, tears, sputum, saliva, tissue samples, and the like); laboratory samples; food, water, or air samples; bioproduct samples such as extracts of cells, particularly recombinant cells synthesizing a desired glycoprotein; and the like. Typically the sample will be suspected of containing an organism which produces neuraminidase, frequently a pathogenic organism such as a virus. Samples can be contained in any medium including water and organic solvent/water mixtures. Samples include living organisms such as humans, and man-made materials such as cell cultures.

The treating step of the invention comprises adding the composition of the invention to the sample or it comprises adding a precursor of the composition to the sample. The addition step comprises any method of administration as described above. If desired, the activity of neuraminidase after application of the composition can be observed by any method including direct and indirect methods of detecting neuraminidase activity. Quantitative, qualitative, and semi-quantitative methods of determining neuraminidase activity are all contemplated. Typically one of the screening methods described above are applied, however, any other method such as observation of the physiological properties of a living organism are also applicable.

Organisms that contain neuraminidase include bacteria (*Vibrio cholerae, Clostridium perfringens, Streptococcus pneumoniae*, and *Arthrobacter sialophilus*) and viruses (especially orthomyxoviruses or paramyxoviruses such as influenza virus A (e.g. H1N1, H5N1), and B, parainfluenza virus, mumps virus, Newcastle disease virus, fowl plague virus, and sendai virus). Inhibition of neuraminidase activity obtained from or found within any of these organisms is within the objects of this invention. The virology of influenza viruses is described in "Fundamental Virology" (Raven Press, New York, 1986), Chapter 24. The compounds of this invention are useful in the prophylaxis of influenza infections or treatment of existing influenza infections in animals such as ducks and other birds, rodents, swine, or in humans.

Compositions of the invention are screened for inhibitory activity against neuraminidase by any of the conventional techniques for evaluating enzyme activity. Within the context of the invention, typically compositions are first screened for inhibition of neuraminidase in vitro and compositions showing inhibitory activity are then screened for activity in vivo. Compositions having in vitro $K_i$ (inhibitory constants) of less than about $5 \times 10^{-6}$ M, typically less than about $1 \times 10^{-7}$ M and preferably less than about $5 \times 10^{-8}$ M are preferred for in vivo use.

Useful in vitro screens have been described in detail and will not be elaborated here. (Itzstein, M. von et al.; "Nature", 363(6428):418-423 (1993); Potier, M.; et al.; "Analyt. Biochem.", 94:287-296 (1979); Chong, A. K. J.; et al.; "Biochem. Biophys. Acta", 1077:65-71 (1991); and Colman, P. M.; et al.; International Publication No. WO 92/06691 (Int. App. No. PCT/AU90/00501, publication date Apr. 30, 1992)). In vivo screens have also been described in detail (Itzstein, et al., 1993 in particular page 421, column 2, first full paragraph, to page 423, column 2, first partial paragraph, and Colman, p. 36).

Table 1 shows neuraminidase inhibition, anti-influenza, and cytotoxicity activities of zanamivir phosphonate derivatives 1a and 1b in comparison with zanamivir and oseltamivir acid. The phosphonate derivatives 1a and 1b showed greater potencies than zanamivir against various wild-type and mutant influenza viruses.

The neuraminidase inhibitory assays were measured against the neuraminidase of several influenza strains using the influenza associated neuraminidase as the enzyme sources. A fluorescence substrate MUNANA (2'-(4-methylumbelliferyl)-α-D-N-acetylneuraminic acid) was used to measure the neuraminidase activities for all viral enzymes. Table 1 shows the $IC_{50}$ values that measure the compound concentrations for 50% inhibition of neuraminidase activities and assess the relative neuraminidase inhibitory potencies of these compounds.

The $IC_{50}$ values for both 1a and 1b against all five neuraminidases are all noticeably more potent than zanamivir and similar to those for oseltamivir acid. These two phosphonate compounds are significantly more active in inhibiting the oseltamivir-resistant neuraminidase mutant of WSN 274Y that has a tyrosine residue replacing the parental histidine at the 274 position of the neuraminidase.

The anti-influenza activities of these compounds were measured against five influenza strains for abilities to protect the influenza infection mediated cytopathic effects. The anti-influenza activities were determined as $EC_{50}$ values that are the concentrations for 50% protection of the infection mediated cytopathic effects. Table 1 shows that 1a and 1b have greater anti-influenza activities against the H1N1 influenza viruses, such as the WSN and the 2009 pandemic H1N1 strains.

The anti-influenza activities of 1a and 1b are particularly noticeable against the oseltamivir-resistant WSN (H1N1) virus. H1N1 influenza viruses carrying the oseltamivir-resistant neuraminidase mutation at the 274 position have been the prevailing H1N1 isolates in clinic (Moscona, A. *N. Engl. J. Med.* 2005, 353, 2633). The superior anti-influenza activities of 1a and 1b for this mutant neuraminidase may impact the option for treating this prevailing influenza strain. In addition to being potent anti-influenza inhibitors against the H1N1 influenza strains, 1a and 1b are also comparable to zanamivir as anti-influenza agents against the RG14 (H5N1) and the Udorn (H3N2) influenza strains.

Bioassay measurements showed that both 1a and 1b are potent anti-neuraminidase and anti-influenza compounds. They are generally more potent than zanamivir and are very active against the oseltamivir-resistant H1N1 influenza viruses. In addition to be potent anti-influenza agents, they are nontoxic to the human 293T cells at the highest testing concentrations (Table 1).

TABLE 1

Neuraminidase inhibition, anti-influenza activity, and cytotoxicity assay

| Bioassay[a] | Measurement | 1a | 1b | Zanamivir | Oseltamivir acid |
|---|---|---|---|---|---|
| WSN (H1N1) | $IC_{50}$ (nM)[b] | 0.65 ± 0.05 | 1.2 ± 0.4 | 5.3 ± 2.1 | 2.6 ± 1.1 |
|  | $EC_{50}$ (nM)[c] | 1.3 | 2.4 ± 0.8 | 23.5 ± 8.5 | 12.2 ± 2.3 |
| WSN_274Y (H1N1) | $IC_{50}$ (nM)[b] | 0.5 | 0.25 ± 0.05 | 1.75 ± 0.75 | 593 ± 68 |
|  | $EC_{50}$ (nM)[c] | 27 | 26 ± 8 | 290 ± 15 | 30000 ± 1600 |
| Pandemic (H1N1) | $IC_{50}$ (nM)[b] | 0.9 | 0.8 | 4.3 | 1.7 |
|  | $EC_{50}$ (nM)[c] | 20.3 | 26.5 | 267 | 76 |
| RG14 (H5N1) | $IC_{50}$ (nM)[b] | 1.0 | 0.8 | 4.0 | 0.6 |
|  | $EC_{50}$ (nM)[c] | 978 | 1700 ± 500 | 16360 ± 2980 | 1250 ± 440 |
| Udorn (H3N2) | $IC_{50}$ (nM)[b] | 6.4 | 5.2 | 37.9 | 3.2 |
|  | $EC_{50}$ (nM)[c] | 55 | 32 ± 23 | 41 ± 6 | 3.0 ± 1.8 |
| 293T cell | $CC_{50}$ (nM)[d] | >30,000 | >50,000 | >100,000 | >100,000 |

[a] Influenza viruses A/WSN/1933 (H1N1), H274Y neuraminidase mutant from A/WSN/1933 (H1N1), A/California/7/2009 (pandemic H1N1), A/Vietnam/1194/2004 RG14 (H5N1), and A/Udorn/307/1972 (H3N2) were used as bioassay materials for neuraminidase inhibition and anti-influenza assays. Human 293T cells were used for cytotoxicity measurements for compounds.
[b] A fluorescent substrate, 2'-(4-methylumbelliferyl)-α-D-N-acetylneuraminic acid (MUNANA) was used to determine the $IC_{50}$ values that are compound concentrations causing 50% inhibition of different influenza neuraminidase enzymes.
[c] Inhibition constants were determined by kinetic studies using MUNANA as the substrate.
[d] The anti-influenza activities against different influenza strains were measured as $EC_{50}$ values that are the compound concentrations for 50% protection of the cytopathic effects due to the infection by different influenza strains.
[e] The highest concentration used without noticeable toxic effects in the assay of cytotoxicity on 293T cells.

In one implementation of the present disclosure, phosphonate 1a is a potent NA inhibitor and anti-flu agent against A/WSN/1933 (H1N1) virus with $IC_{50}$ and $EC_{50}$ values of 0.65 and 1.3 nM, respectively.

In one implementation of the present disclosure, phosphonate 1a is a potent NA inhibitor and anti-flu agent against the H274Y mutant of A/WSN/1933 (H1N1) virus with $IC_{50}$ and $EC_{50}$ values of 0.5 and 27 nM, respectively. These $IC_{50}$ and $EC_{50}$ values of the zanamivir phosphonate are particularly impressive for Tamiflu-resistant H1N1 virus.

In one implementation of the present disclosure, phosphonate 1a is also a potent NA inhibitor and anti-flu agent against A/California/7/2009 (pandemic H1N1), A/Vietnam/1194/2004 RG14 (H5N1), and A/Udorn/307/1972 (H3N2) viruses.

In one implementation of the present disclosure, phosphonate 1b is a potent NA inhibitor and anti-flu agent against A/WSN/1933 (H1N1) virus with $IC_{50}$ and $EC_{50}$ values of 1.2 and 2.4 nM, respectively.

In one implementation of the present disclosure, phosphonate 1b is a potent NA inhibitor and anti-flu agent against the H274Y mutant of A/WSN/1933 (H1N1) virus with $IC_{50}$ and $EC_{50}$ values of 0.25 and 26 nM, respectively. The high potency of 1b against Tamiflu-resistant H1N1 virus is very significant.

In one implementation of the present disclosure, phosphonate 1b is also a potent NA inhibitor and anti-flu agent against A/California/7/2009 (pandemic H1N1), A/Vietnam/1194/2004 RG14 (H5N1), and A/Udorn/307/1972 (H3N2) viruses.

In one aspect of the invention, molecular modeling of the neuraminidase-phosphonate complex indicates a pertinent binding mode of the phosphonate with three arginine residues in the active site. The molecular docking experiments (FIG. 2) using the known N1 crystal structure (PDB code: 2HU4) reveal that the phosphonate inhibitor 1b binds strongly with the tri-arginine residues of NA, in addition to other interactions exerted by the $C_7$-$C_9$ glyceryl, $C_4$-acetamido and $C_5$-guanidino groups in the binding pocket similar to the neuraminidase-zanamivir complex.

Figure 2:
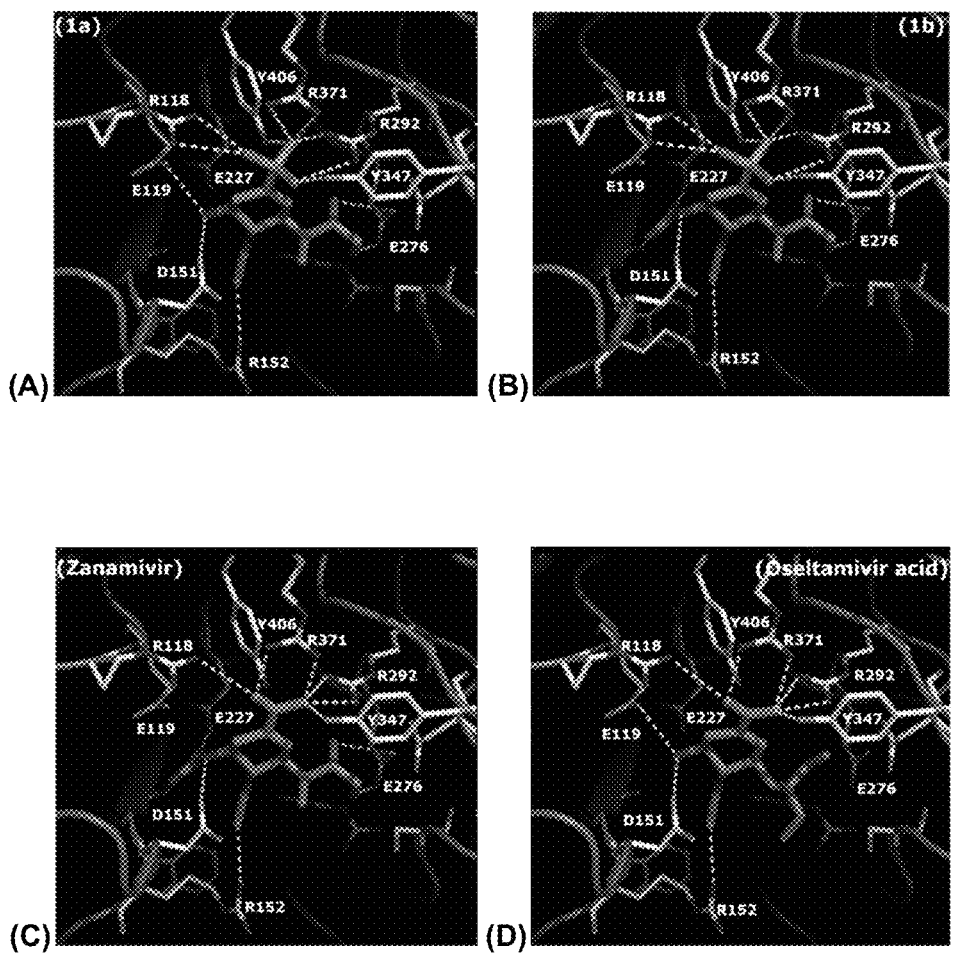
FIGS. 2A-2D show molecular models of compounds 1a (2A), 1b (2B), zanamivir (2C) and oseltamivir acid (2D).

In one aspect of the invention, molecular modeling of phosphonate inhibitor 1a showed the strong interactions with the three arginine residues of neuraminidase, in addition to other interactions exerted by the $C_7$-$C_9$ glyceryl, $C_4$-acetamido and $C_5$-amino groups in the binding pocket (FIG. 2).

Identification of Tamiflu-Resistant Viral Isolates

The specification herein discloses the design and practice of the method of Resistance Assessment by Binding Competition (RABC) for development of effective diagnostics for Tamiflu-resistant viral isolates.

Zanamivir and OC bind to the same active site of influenza neuraminidase (NA). However, oseltamivir-resistance H5N1 virus neuraminidase can still retain susceptibility to zanamivir. (Collins P J, et al. (2008). *Nature* 453 (7199): 1258-1261). An induced fit of the neuraminidase that involves the reorientation of the Glu276 residue toward Arg224 creating a larger hydrophobic pocket is needed to accommodate the side chain of OC (M. Z. Wang, C. Y. Tai, D. B. Mendel, *Antimicrob. Agents Chemother.* 46, 3809 (2002); P. J. Collins et al., *Nature* 453, 1258 (2008)). The N1 group neuraminidases can evolve to resistant forms with mutations such as H274Y that prevent the formation of the hydrophobic pocket resulting in several hundred fold increase in the oseltamivir $K_i$ values. In the absence of the need of a hydrophobic pocket, the zanamivir $K_i$ for the H274Y neuraminidase is unchanged (P. J. Collins et al., *Nature* 453, 1258 (2008)). In a feature of the invention, the binding difference was explored to develop a novel diagnosis for OC susceptibility of viral isolates.

Selection of a recognition unit (R) that binds to the oseltamivir-binding region of influenza virus neuraminidase and using the differential binding between oseltamivir-sensitive and oseltamivir-resistant versions of influenza virus has been surprisingly found to be a basis for detecting Tamiflu-resistant strains of influenza virus.

In certain aspects of the invention the recognition unit (R) is coupled to a sensor unit (S). In some embodiments, the recognition unit (R) is coupled to a linker (L) which is in turn coupled to a sensing unit (S). The R-L-S molecule is used to distinguish Tamiflu-resistant from Tamiflu-sensitive influenza viruses.

Being a potent neuraminidase inhibitor, oseltamivir carboxylate (OC; Tamiflu®) is an effective competitor for non-OC molecules (R) that bind to NA molecules in influenza viruses. However, OC is a poor competitor for the binding of the OC-resistant mutants (e.g., H274Y) that still binds non-OC recognition units (R) equally as well as wild type NA.

The recognition unit (R) is typically selected from a known NA binding moiety such a zanamivir, tamiphosphor guanidine monoester, or zanamivir phosphonate 1a or its derivatives 1b, 1c and 1d. In some embodiments, R is selected from oseltamivir-containing phosphonate compounds that have activity as neuraminidase inhibitors against wild-type and H274Y mutant of H1N1 and H5N1 viruses as disclosed in U.S. Pat. No. 7,888,337B2.

Binding to NA is detected by the signal from the sensing moiety (i.e. detectable moiety) can be observed. Such homogenous fluorescent and calorimetric sensing moieties are known to those skilled in the art. See, for example: Wang Q. M. et al., "A continuous calorimetric assay for rhinovirus-14 3C protease using peptide p-nitroanilides as substrates" Anal. Biochem. Vol. 252, pp. 238-45 (1997), and Basak S. et al. "In vitro elucidation of substrate specificity and bioassay of pro-protein convertase 4 using intramolecularly quenched fluorogenic peptides" Biochem. J. Vol. 380, pp. 505-14 (2004).

The sensor unit is linked directly or indirectly (via avidin/streptavidin-biotin, antibody-antigen, or other methods known in the art) to a detectable moiety selected from the group consisting of a fluorescent label, a gold label and an enzyme label. The various kinds of sensors are not particularly limited and can be appropriately selected according to the purpose. Examples thereof include radioactive labels, quantum dot labels, protein labels, and the like.

In some aspects the sensing unit forms a detectable binding complex with a conjugated binding partner, forming a binding pair, wherein said binding partner is conjugated to a reagent. The binding pair may be based on any of: the binding pair is any one selected from the group consisting of streptavidin:biotin; avidin:biotin; folic acid:folate binding protein; sialic acid, carbohydrates, or glycoproteins:lectins; oligo- or poly-dA:oligo- or poly-dT; oligo- or poly-dC:oligo- or poly-dG; phenylboronic acid:salicylhydroxamic acid; aldehyde and ketone moieties:hydrazides; sulfhydryl moiety:maleimides; amino moieties:N-hydroxysuccinimide esters; and heavy metals:thiols; the Fc portion of IgG: Protein A/Protein G/Protein A/G; digoxigenin:anti-digoxigenin; 5-bromodeoxyuridine:anti-bromodeoxyuridine; dinitrophenyl:anti-dinitrophenyl; fluorescein isothiocyanate:anti-fluorescein isothiocyanate; N-2-acetylaminofluorene:anti-N-2-acetylaminofluorene; and N-2-acetylamino-7-iodofluorene:anti-N-2-acetylamino-7-iodofluorene.

In certain aspects the label comprises a fluorphore. In some aspects, the fluorophore is selected from the group consisting of fluorescein, rhodamine, coumarin, resorufin, xanthene, cyanine, pyrene, phthalocyanine, phycobiliprotein, Alexa, Cy3, Cy5, squarene dye, combinations resulting in energy transfer dyes, and derivatives thereof. The Alexa fluorescent dye may be selected from the group consisting of Alexa Fluor 647, Alexa Fluor 546 and Alexa Fluor 532. In some embodiments the fluorophore is selected from the group consisting of: BODIPY maleimides, iodoacetamides and methyl bromides; Alexa Fluor maleimides; fluorescein 5- and 6-isomer maleimides and methyl bromides; Oregon Green isothiocyanates and maleimides; tetramethylrhodamine 5- and 6-isomer iodoacetamides and maleimides; Rhodamine Red maleimides; Texas Red bromoacetamides and maleimides; pyridyloxazole maleimides; benzoxadiazole derivatives including NBD halides and iodoacetamides, SBD; Lucifer Yellow iodoacetamide; stilbene iodoacetamides and maleimides; coumarin maleimides and iodoacetamides, i.e. MDCC, IDCC, and others; naphthalene derivatives, i.e. acrylodan, badan, IAANS, MIANS, IAEDANS, and Dansyl; aziridine; dapoxyl derivatives, i.e. dapoxyl (2-bromoacetamidly)sulfonamide; pyrene maleimides and iodoacetyl derivatives; and monobromo- and monochlorobimanes.

The method or means for detecting the signal from the sensor unit (S) is not particularly limited and can be appropriately selected according to the purpose. For example, when the signal is emission, quenching, etc., it is detected by a photodetector, camera, etc.

The combination of the light-emitting portion and the quenching portion is not particularly limited and can be appropriately selected according to the purpose. For example, those known as the technique of fluorescence resonance energy transfer (FRET), etc. can be suitably adopted.

The light-emitting portion is not particularly limited as long as it can generate emission, and can be appropriately selected according to the purpose. Examples thereof include those containing a fluorescent substance, chemiluminescent substance, electrochemiluminescent substance, etc. or those formed of these substances. These may be used alone or two or more may be used in combination. Among these, in the case where the quenching portion is present adjacent to the light-emitting portion, those of which emission is quenched by the action of the quenching portion are preferable, the fluorescent substance is more preferable in that visibility thereof is excellent and detection is easy. The fluorescent substance is not particularly limited and can be appropriately selected according to the purpose. Examples thereof include anthracene, fluorescein, fluorescein isothiocyanate (FITC), rhodamines such as tetramethyl rhodamine and sulforhodamine, dansyl chloride, Texas Red, AL 350, indocarbocyanine (CY), and the like.

The quenching portion is not particularly limited if it can quench the emission of the light-emitting portion when the quenching portion is located adjacent to the light-emitting portion, and the quenching portion can be appropriately selected according to the type, etc. of the light-emitting portion. Examples thereof include those containing a quenching substance, or those formed of the quenching substance. The quenching substance is not particularly limited and can be appropriately selected according to the purpose. When the light-emitting portion is formed of the fluorescent substance, examples of the quenching substance include substances capable of absorbing the energy released when the fluorescent substance emits light, and the like. Suitable examples include substances allowing fluorescence resonance energy transfer (FRET) between the light-emitting substance. Specific examples include tetramethylrhodamine isothiocyanate (TRITC), dimethylaminobenzenesulfonyl (DABSYL), gold nanoparticles, Black Hole Quencher, and the like.

The recognition unit is conjugated to a sensor which is in turn coupled to a light-emitting portion and a quenching portion. The quenching portion can quench emission of the light-emitting portion before the recognition unit binds to the target NA, i.e., when the quenching portion is present adjacent to the light-emitting portion. After the recognition unit has bound to the target NA, the quenching portion dissociates from the target nucleic acid. As a result, the quenching portion exists away from the light-emitting portion, resulting in the loss of the action of the quenching portion and allowing the light-emitting portion to generate emission.

The linker unit (L) is not particularly limited and can be appropriately selected as long as it does not impair the effect of the invention. For example, a water-soluble linker such as ethylene glycol linker can be used. The length of the water-soluble linker can be determined to an appropriate length.

In one aspect, either the influenza virus sample to be tested or the R-L-S complex is immobilized on a solid surface as an array. The solid surface may be selected from the group consisting of Langmuir Blodgett film, glass, germanium, silicon, (poly)tetrafluoroethylene, polystyrene, gallium arsenide, gallium phosphide, silicon oxide, silicon nitride, and combinations thereof. The solid surface may be any one selected from the group consisting of a microwell or microtiter plates or dishes, silicon chips, glass slides, beads, microparticles, films or membranes, bottles, dishes, slides, blotting material, filters, fibers, woven fibers, shaped polymers, particles, dip-sticks, test tubes, chips, and microchips.

In one embodiment, the influenza virus and/or virus particles are bound to a support containing at least one type of carbohydrate receptor selected from the group consisting of natural or synthetic oligosaccharide, which is conjugated to, or situated in composition with glycoproteins like glycophorin, $\alpha$1-acid glycoprotein, $\alpha$2-macroglobulin, ovomucoid, and combinations thereof which carbohydrate receptor binds to the hemagglutinin component of the viruses and/or virus particles. In particular, influenza viruses and/or virus particles comprising all known Avian Influenza (AI) sub-types that are normally sensitive to Tamiflu® can detected. The method is suitable to detect influenza viruses and/or virus particles comprising a highly pathogenic variant that is resistant to Tamiflu®. The invention can be performed in particular with a support which is a chromatographic paper or membrane. Such materials are well-known to the skilled person. According to the invention it is possible to covalently attach or physically adsorb the carbohydrate receptor to the support. (US Pub. Pat. App. Ser. No. 20100009339).

Methods of the invention can be used with suspected influenza virus containing samples selected from the group consisting of mucus, saliva, respiratory secretion, throat wash, nasal wash, spinal fluid, sputum, urine, semen, sweat, feces, plasma, blood, broncheoalveolar fluid, vaginal fluid, tear fluid and tissue biopsy. Similar techniques are also applicable for use with virus samples from cell culture, e.g., influenza samples grown in cells such as Vero cells, etc. The methods of the invention are suitable for practicing on intact influenza virus-infected cells or cell-free samples of influenza virus. The influenza virus can be of mammalian (human, equine, swine, etc.) or avian origin.

Kits

Kits which comprise the neuraminidase binding molecules of the present invention are also envisaged. The different kit components may be packaged in separate containers and admixed immediately before use. Such packaging of the components separately may permit long-term storage without losing the active components' functions. Embodiments in which two or more of components are found in the same container are also contemplated. An exemplary kit may comprise one or more of the following reagents: a wash buffer reagent for use using heterogeneous assays; a negative control reagent free of a neuraminidase-binding capability; a signal generation reagent for development of a detectable signal from the signaling moiety; and a sample collection means such as a syringe, throat swab, or other sample collection device. The kits of the present invention may, if desired, be presented in a pack which may contain one or more units of the kit of the present invention. The pack may be accompanied by instructions for using the kit. The pack may also be accommodated by a notice associated with the container in a form prescribed by a governmental agency regulating the manufacture, use or sale of laboratory supplements, which notice is reflective of approval by the agency of the form of the compositions.

Exemplary Embodiments of the Binding Molecules:

The invention relates to detection of Tamiflu-resistant influenza virus strains by determining the binding ability of specific binding molecules having the structure recognition unit (R)-optional linker (L)-sensing unit (S).

Examples of some embodiments of the binding molecule (BM) according to the invention are:

BM 1: Zanamivir-Triazole Linker-Biotin

The linker containing a triazole group is formed by click chemistry (1,3-dipolar cycloaddition of alkyne and azide). Fluorescence labeled streptavidin is used to detect the biotin unit.

BM 2: Zanamivir-Triazole Linker-Fluorescein

Fluorescein has an absorption maximum at 494 nm and emission maximum of 521 nm (in water). Fluorescein isothiocyanate (FITC) is used to connect with the linker. Alternatively, other fluorescent entities such as Alexa dyes and quantum dots, can be used.

BM 3: Zanamivir-Ethylene Glycol Linker-Biotin

The length of ethylene glycol linker can be tuned from x=1 to x=4.

BM 4: Zanamivir-Ethylene Glycol Linker-Fluorescein

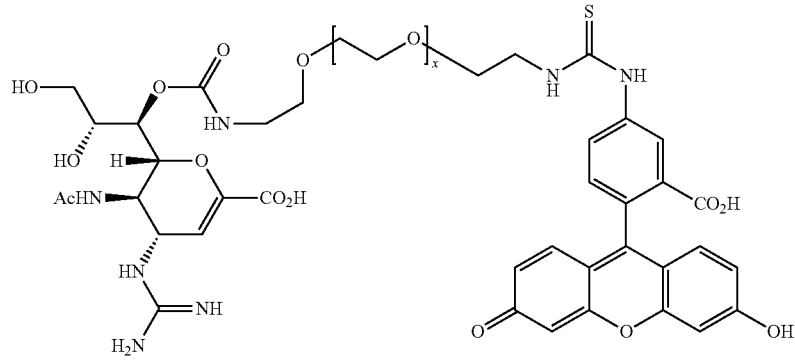

BM 5: Tamiphosphor Guanidine-Linker-Biotin

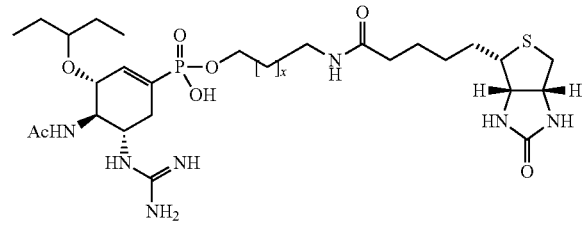

Tamiphosphor guanidine binds both Tamiflu-sensitive and Tamiflu-resistant strains (H274Y) of influenza viruses. The Tamiphosphor guanidine monoester can be in the salt form, such as the ammonium salt. The aliphatic chain can have 1-6 carbons (x=1-4) in the linker. Alternatively, the aliphatic chain can be replaced by ethylene glycol chain as shown in Example 3.

BM 6: Tamiphosphor Guanidine-Ethylene Glycol Linker-Fluorescein

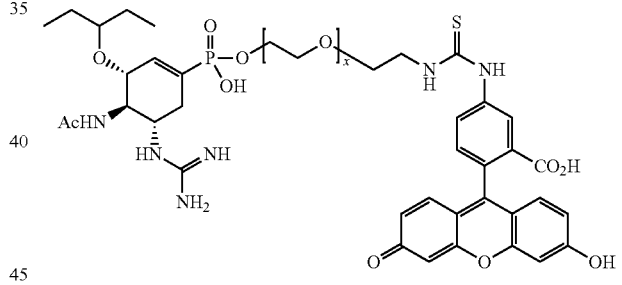

BM 7: PhosphaZanamivir-Triazole Linker-Biotin

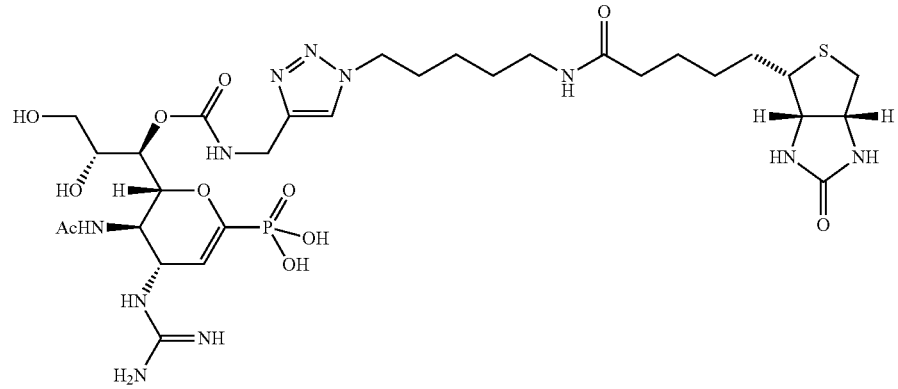

PhosphaZanamivir can be in the salt form, such as the ammonium salt.

BM 8: PhosphaZanamivir-Ethylene Glycol Linker-Fluorescein

PhosphaZanamivir can be in the salt form, such as the ammonium salt.

BM 9: PhosphaZanamivir Monoester-Ethylene Glycol Linker-Biotin

The length of ethylene glycol linker can be tuned from x=1 to x=4.

BM 10: PhosphaZanamivir Monoester-Ethylene Glycol Linker-Fluorescein

The length of ethylene glycol linker can be from x=1 to x=4.

Other exemplars of influenza NA-binding molecules of the general structure R-L-S are disclosed in Kale, R. R. et al., *Am. Chem. Soc.* 2008, 130, 8169-8171; Mckimm-Breschkin, J. L. et al., *Angew. Chem. Int. Ed.* 2003, 42, 3118-3121; Lu, C.-P. et al., *Angew. Chem. Int. Ed.* 2005, 44, 6888-6892; Kimura, Y. et al., *Tetrahedron Lett.* 2009, 50, 3205-3208.

The present disclosure for the first time reveals that NA-binding abilities of molecules of the structure R-L-S can be used to detect Tamiflu-resistant versions of influenza virus.

Competitive Binding of NA with Oseltamivir Carboxylate (OC) and R-L-S Type Binding Molecules A biotin-conjugated zanamivir (ZB) that binds influenza neuraminidases effectively was prepared. In the presence of oseltamivir carboxylate (OC) as the competitor for zanamivir binding, OC susceptibility could be determined. The OC binding competition assay confirmed the dramatic increase of OC resistant H1N1 isolates from 2008 and the appearance of OC resistant pandemic 2009 H1N1 in Taiwan. The Resistance Assessment by Binding Competition (RABC) assay was used to develop a prototype "point-of-care" test for OC susceptibility assessment. The RABC-assay principle could be generally applicable to high throughput survey and quick diagnosis for drug susceptibility of pathogens.

A biotin conjugated zanamivir (ZB) was prepared for this study (FIG. 1A, Examples). ZB was made by conjugation of a biotin through a linker to zanamivir at the 7-OH position that can be derivatized without much reduction in neuraminidase inhibition (D. M. Andrews et al., *Eur. J. Med. Chem.* 34, 563 (1999); T. Honda et al., *Bioorg. Med. Chem. Lett.* 12, 1925 (2002); W. H. Wen et al., *J. Med. Chem.* 52, 4903 (2009)). The $IC_{50}$ value of ZB against neuraminidase was found to be 7.7 nM, higher than that of zanamivir (2.1 nM). ZB binding to influenza neuraminidase was demonstrated using neuraminidase transfected cells (FIG. 4), influenza infected cells (see Examples), and immobilized influenza viruses (FIG. 1B). Being a potent neuraminidase inhibitor, oseltamivir carboxylate (OC) could be an effective competitor for ZB binding to influenza viruses.

Nevertheless, OC was also expected to be a poor competitor for the binding of the OC-resistant H274Y mutant that ZB binds equally well. FIG. 1B shows that significant OC inhibition ($p<0.001$) on ZB binding was shown in the measurements of 274H influenza virus with titers in the range of $10^3$-$10^5$ PFU. A residual ZB binding about 3% was noticed in OC competition of higher titer 274H viral samples. In contrast, significant inhibition of ZB binding by competing OC was not observed in the OC resistant 274Y WSN virus at the same titers.

Figure 14:
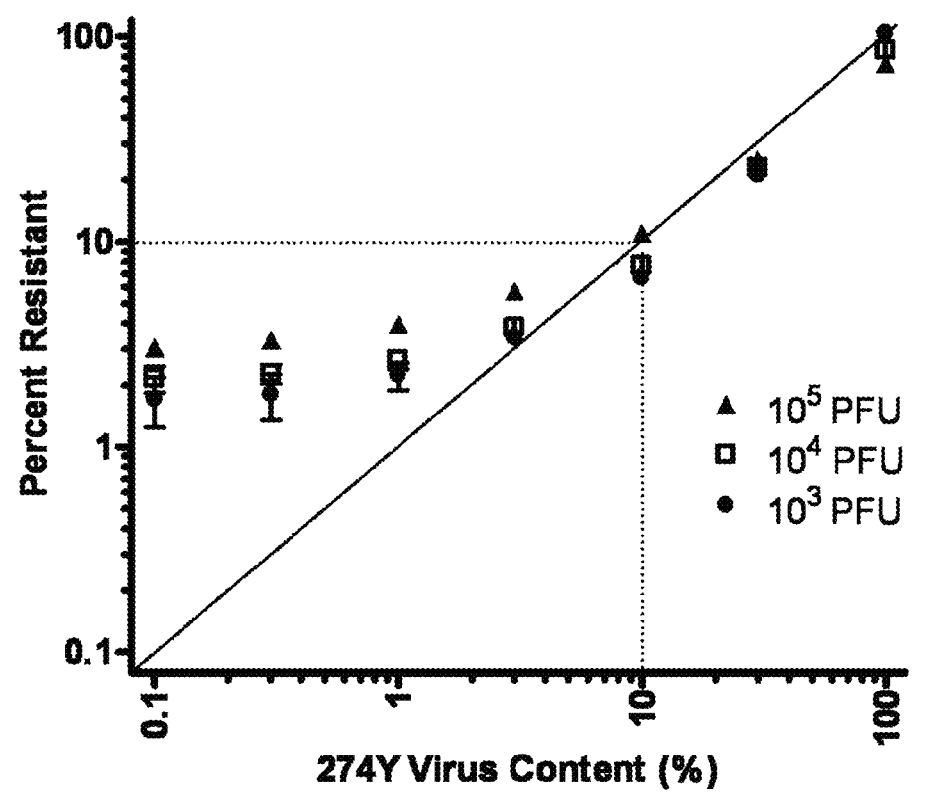

The same observations were demonstrated using transformed and influenza infected cells (FIGS. 11-14). We named this assay Resistance Assessment by Binding Competition, or RABC in short. We also showed that the RABC assay allows the detection of the OC-resistant 274Y mutants in mixed populations at greater than 10% resistant contents (FIG. 14).

Figure 8:
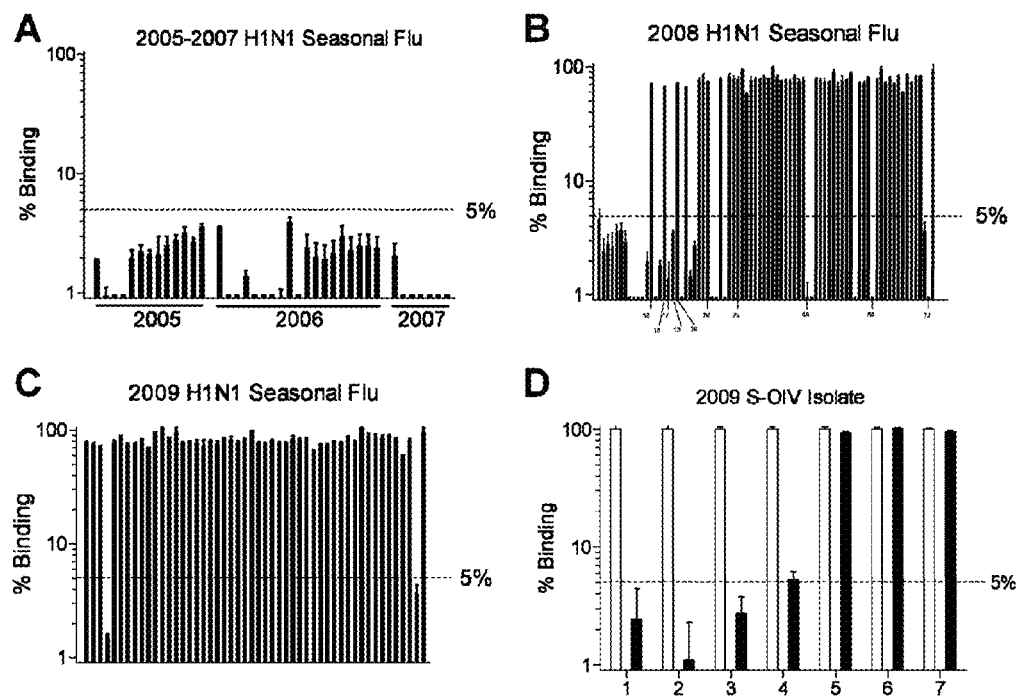
FIGS. 8A-8D show determination of OC susceptibility of clinical influenza isolates collected in Taiwan in the years 2005-2009. Seasonal H1N1 collected in Taiwan in years 2005-2007 (8A), 2008 (8B), and 2009 (8C) were used for OC susceptibility study. OC resistant ZB binding were measured and calculated as described in FIG. 1B. Binding values below 1% were presented as 1%. The dashed lines marked the 5% binding values were used to call the susceptibility status of the testing viruses. (8D) OC susceptibility of seven 2009 pandemic H1N1 isolates was measured in an identical fashion except triplicate measurements were made on total and OC-resistant bindings. In addition, both total and OC resistant bindings are shown.

A total of 137 Taiwan seasonal H1N1 clinical isolates collected in the years 2005-2009 were queried by the RABC assay for OC susceptibilities. The viral samples were immobilized in anti-H1N1 coated microplate wells and tested for binding using either 30 nM ZB or 30 nM ZB plus 150 nM OC in duplicate assays. The 5% residual ZB binding was used as the cut-off for OC susceptibility determination. The RABC assay results suggested that all tested seasonal H1N1 isolates collected before 2008 (FIG. 8A) or early in 2008 (FIG. 8B) were OC susceptible. Not until mid 2008, OC-resistant H1N1 was isolated in Taiwan (FIG. 8B). Similarly, 48 out of 50 seasonal H1N1 collected in 2009 were scored as OC resistant (FIG. 8C). We also examined the OC susceptibility of the pandemic 2009 H1N1 isolates collected in Taiwan. FIG. 8D shows that isolates ##1-4 and isolates ##5-7 are OC susceptible and OC resistant viruses, respectively. The RABC assays of the seven strains were conducted in blind, and the results were later shown to be consistent with their OC susceptibility and sequence results. To evaluate the susceptibility prediction using the RABC assay, 60 isolates of the seasonal H1N1 samples described in FIG. 8A-C were randomly picked to analyze their neuraminidase sequences. All samples predicted as OC sensitive by the RABC assay have histidines, while those predicted to be OC resistant have tyrosines at the corresponding residue 274 of the neuraminidases (Table 2). To seek the possible presence of evolving resistant populations, we took a closer look of those samples with 3-5% residual ZB binding values. Analyses of several isolated viral plaques from these samples failed to identify OC resistant viruses by binding or sequence analyses.

Table 2 lists all Taiwan clinical H1N1 isolates used in this study for determination of their OC susceptibility status by the RABC assays. Sixty viral isolates were randomly selected to determine their sequences at amino acid 274 ($AA_{274}$; N2 nomenclature) of the viral neuraminidase. In addition, a few samples were tested using the quick assay on membrane for OC susceptibility determinations. No discrepancies were found in all assay results, indicating that the RABC is reliable for OC susceptibility determinations.

TABLE 2

OC susceptibility determination of Taiwan seasonal H1N1 isolates. The OC susceptibility of each influenza isolate determined by the RABC assay is designated as R (resistant) or S (susceptible) according to the results of FIG. 8. Several isolates were randomly picked for confirmation by analysis of $AA_{274}$ and (or) quick test on a membrane (the numbers in parentheses corresponding to the sample number used in FIG. 8B).

| Name[a] | OC[b] | $AA_{274}$ | Quick test |
|---|---|---|---|
| 2009-03510 | R | Tyr | |
| 2009-02548 | R | Tyr | |
| 2009-02020 | R | | |
| 2009-01051 | R | | |
| 2009-01022 | R | | |
| 2009-00516 | R | | |
| 2009-00513 | R | | |
| 2009-00512 | R | | |
| 2009-01524 | R | Tyr | |
| 2009-00521 | R | | |
| 2009-00519 | R | | |
| 2009-00518 | R | | |
| 2009-04512 | R | | |
| 2009-00511 | R | | |
| 2009-03518 | R | | |
| 2009-03019 | R | Tyr | |
| 2009-03005 | R | Tyr | |
| 2009-90010 | R | | |
| 2009-02530 | R | Tyr | |
| 2009-02027 | R | Tyr | |
| 2009-02031 | R | | |
| 2009-01026 | R | Tyr | |
| 2009-04511 | R | Tyr | |
| 2009-01518 | R | | |
| 2009-01516 | R | | |
| 2009-04017 | R | | |
| 2009-03522 | R | Tyr | |
| 2009-03507 | R | | |
| 2009-03003 | R | Tyr | |
| 2009-03002 | R | Tyr | |
| 2009-02022 | R | | |
| 2009-01043 | R | | |
| 2009-03006 | R | | |
| 2009-00024 | R | Tyr | |
| 2009-04010 | R | Tyr | |
| 2009-00515 | R | Tyr | |
| 2009-00514 | R | | |
| 2009-00510 | R | | |
| 2009-04503 | R | Tyr | |
| 2009-01514 | R | | |
| 2009-01021 | S | His | |
| 2009-02013 | R | | |
| 2009-04007 | R | | |
| 2009-02010 | R | Tyr | |
| 2009-01522 | S | His | |
| 2008-03020 | S | His | S(73) |
| 2009-00009 | R | | |
| 2009-00008 | R | Tyr | |
| 2008-11526 | R | Tyr | |
| 2008-00846 | R | | |
| 2008-00842 | R | | |
| 2008-09219 | R | | |
| 2008-00843 | R | | |
| 2008-02904 | R | | |

TABLE 2-continued

OC susceptibility determination of Taiwan seasonal H1N1 isolates. The OC susceptibility of each influenza isolate determined by the RABC assay is designated as R (resistant) or S (susceptible) according to the results of FIG. 8. Several isolates were randomly picked for confirmation by analysis of $AA_{274}$ and (or) quick test on a membrane (the numbers in parentheses corresponding to the sample number used in FIG. 8B).

| Name[a] | OC[b] | $AA_{274}$ | Quick test |
|---|---|---|---|
| 2008-09202 | R | | |
| 2008-05878 | R | Tyr | |
| 2008-09201 | R | | |
| 2008-06020 | S | His | S(64) |
| 2008-05879 | R | Tyr | |
| 2008-02906 | R | | |
| 2008-08884 | S | His | |
| 2008-09200 | R | Tyr | |
| 2008-09199 | R | | |
| 2008-02415 | R | Tyr | |
| 2008-00841 | R | | |
| 2008-10128 | R | Tyr | |
| 2008-02418 | R | | |
| 2008-05877 | R | Tyr | |
| 2008-00302 | R | | |
| 2008-09198 | R | | |
| 2008-90003 | S | | S(49) |
| 2008-09020 | S | His | |
| 2008-11548 | R | | |
| 2008-05866 | R | Tyr | |
| 2008-05860 | R | Tyr | |
| 2008-05859 | R | Tyr | |
| 2008-05858 | R | Tyr | |
| 2008-05857 | R | Tyr | |
| 2008-11547 | R | | |
| 2008-00286 | R | Tyr | |
| 2008-05855 | R | Tyr | |
| 2008-02901 | R | | |
| 2008-00279 | R | Tyr | |
| 2008-00839 | R | | |
| 2008-00275 | R | | |
| 2008-08451 | R | Tyr | |
| 2008-00273 | R | | |
| 2008-09159 | R | Tyr | |
| 2008-09042 | R | Tyr | R(33) |
| 2008-08949 | R | Tyr | |
| 2008-08885 | S | His | |
| 2008-05853 | R | Tyr | |
| 2008-08416 | S | His | |
| 2008-00258 | S | His | |
| 2008-10103 | R | Tyr | R(26) |
| 2008-06758 | R | Tyr | |
| 2008-02885 | R | Tyr | |
| 2008-06723 | S | His | |
| 2008-10099 | R | Tyr | |
| 2008-10095 | S | His | |
| 2008-08319 | S | His | |
| 2008-02832 | R | Tyr | R(19) |
| 2008-00233 | S | His | S(18) |
| 2008-05506 | S | His | S(17) |
| 2008-07903 | S | | |
| 2008-07895 | R | | R(16) |
| 2008-07860 | R | Tyr | R(13) |
| 2008-02808 | S | His | |
| 2008-05815 | S | His | |
| 2008-03293 | S | | |
| 2008-09169 | S | | |
| 2008-04240 | S | | |
| 2008-03135 | S | | |
| 2008-02612 | S | | |
| 2008-04226 | S | | |
| 2008-04063 | S | | |
| 2008-04169 | S | | |
| 2007-05601 | S | | |
| 2007-02774 | S | | |
| 2007-02578 | S | | |
| 2007-05222 | S | | |
| 2007-04656 | S | | |
| 2007-02820 | S | | |
| 2007-02523 | S | | |
| 2007-02864 | S | | |
| 2007-03700 | S | | |
| 2007-02782 | S | | |
| 2006-05288 | S | | |
| 2006-06542 | S | | |
| 2006-00061 | S | | |
| 2006-05751 | S | | |
| 2006-00010 | S | | |
| 2006-04130 | S | | |
| 2005-05524 | S | | |
| 2005-10393 | S | | |
| 2005-05515 | S | | |
| 2005-03468 | S | | |

[a]CDC virus names
[b]OC susceptibility

Point of Care Assay

Figure 9:
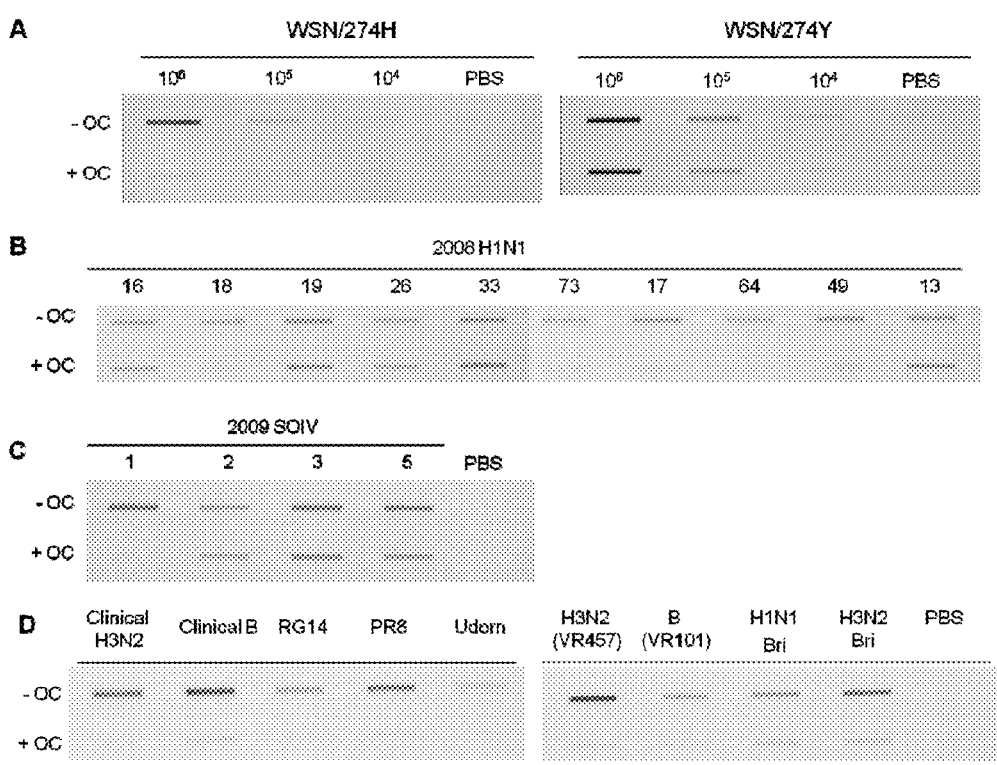
FIGS. 9A-9D show the prototype "point-of-care" assay for OC susceptibility determination of influenza viral samples. (9A) A PVDF membrane with immobilized anti-HA antibody slots was used to absorb influenza samples that were pre-incubated with either 30 nM ZB or 30 nM ZB plus 150 nM OC. In this study, the wild type WSN (274H) or the OC resistant WSN (274Y) mutant viruses at $10^4$, $10^5$, $10^6$ PFU per slot were used. After blotting and washing, the membrane was treated with streptavidin conjugated alkaline phosphatase and stained with BCIP/NBT to visually determine the OC susceptibility of the virus samples. (9B) Ten 2008 Taiwan seasonal H1N1 isolates, described in FIG. 8B, were validated using the membrane assay. (9C) Similarly, four pandemic H1N1 viral strains tested in FIG. 8D were evaluated using the prototype assay. (9D) OC competition of ZB binding was determined in several other A-type or B-type influenza viruses using a modified method involving direct immobilization of the virus samples to a PVDF membrane without an antibody and then processed in an identical fashion.

Disclosed herein is a prototype assay on membrane for visual assessment of the OC susceptibility state of the influenza viruses. FIG. 9A shows that the staining of the OC susceptible H1N1 (WSN) by ZB was blocked by OC competition while the staining of the OC resistant 274Y WSN was resistant to the same competition. We used the staining on membrane to confirm the status of the OC susceptibility of several seasonal and pandemic H1N1 isolates (FIGS. 9B and 9C). The sensitive ZB binding was also demonstrated on H1N1, H3N2, H5N1, and flu B influenza viruses that were directly immobilized on a membrane (FIG. 9D). The prototype RABC based staining assay is quick and requires no instruments for detections. It could be used as a "point-of-care" assay in a doctor's office for timely decision on treatment options for the seasonal H1N1 or pandemic H1N1 infections. In addition, the test could be used to differentiate influenza virus versus other respiratory infections as most other respiratory infective pathogens do not have neuraminidases.

The RABC assay is a simple and robust method and has been demonstrated on different influenza viruses and infected cells using a variety of assay platforms. The assay principle could be applicable to other pathogen targets for drug susceptibility assessments.

EXAMPLES

Without intent to limit the scope of the invention, exemplary instruments, apparatus, methods and their related results according to the embodiments of the present invention are given below. Note that titles or subtitles may be used in the examples for convenience of a reader, which in no way should limit the scope of the invention. Moreover, certain theories are proposed and disclosed herein; however, in no way they, whether they are right or wrong, should limit the scope of the invention so long as the invention is practiced according to the invention without regard for any particular theory or scheme of action.

All the reagents were commercially available and used without further purification unless indicated otherwise. All solvents were anhydrous grade unless indicated otherwise. All non-aqueous reactions were carried out in oven-dried glassware under a slight positive pressure of argon unless otherwise noted. Reactions were magnetically stirred and monitored by thin-layer chromatography on silica gel. Flash chromatography was performed on silica gel of 60-200 μm particle size. Yields are reported for spectroscopically pure compounds. Melting points were recorded on an Electrothermal MEL-TEMP® 1101D melting point apparatus and are not corrected. $^1$H and $^{13}$C NMR spectra were recorded on Bruker AVANCE 600 spectrometer. The $^{31}$P NMR spectra were recorded on Bruker AVANCE 500 spectrometer. Chemical shifts are given in δ values relative to tetramethylsilane (TMS); coupling constants J are given in Hz. Internal standards were CDCl$_3$ ($\delta_H$=7.24), MeOH-d$_4$ ($\delta_H$=3.31) or D$_2$O ($\delta_H$=4.79) for $^1$H-NMR spectra, CDCl$_3$ ($\delta_c$=77.0) or MeOH-d$_4$ ($\delta_c$=49.15) for $^{13}$C-NMR spectra, and H$_3$PO$_4$ in D$_2$O ($\delta_P$=0.00) for $^{31}$P-NMR spectra. The splitting patterns are reported as s (singlet), d (doublet), t (triplet), q (quartet), m (multiplet), br (broad) and dd (double of doublets). IR spectra were recorded on a Thermo Nicolet 380 FT-IR spectrometer. Optical rotations were recorded on a Perkin-Elmer Model 341 polarimeter. High resolution ESI mass spectra were recorded on a Bruker Daltonics spectrometer.

Example 1

3-Acetamido-4,6-diacetoxy-2-(1,2,3-triacetoxy)propyl-3,4,5,6-tetrahydro-2H-pyran (3)

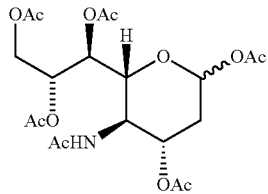 [SMILES: CC(=O)N[C@H]1[C@H]([C@H](OC(C)=O)[C@@H](COC(C)=O)OC(C)=O)OC(OC(C)=O)C[C@@H]1OC(C)=O]

Under an atmosphere of nitrogen, a suspension of N-acetylneuraminic acid (5 g, 16.2 mmol) in pyridine (75 mL) and acetic anhydride (75 mL) was stirred at room temperature for 12 h, and then heated at 100° C. for 5 h. The reaction mixture was cooled to room temperature, and concentrated under reduced pressure. The residual brownish glassy oil was dissolved in CH$_2$Cl$_2$ (150 mL), and washed successively with saturated aqueous NaHCO$_3$ (100 mL), aqueous 1 M HCl (100 mL) and brine (100 mL). The organic layer was dried over MgSO$_4$, filtered and concentrated. The brownish residue was purified by column chromatography on silica gel (EtOAc/hexane, 67:33 to 100:0) to afford 3 as a pale yellow foam (3.8 g, 50%), which contained inseparable mixture of anomers (α/β=1:5). The anomeric mixture of 3 was used in the next step without further separation. C$_{20}$H$_{29}$NO$_{12}$; TLC (EtOAc) R$_f$=0.35; $^1$H NMR (600 MHz, CDCl$_3$) δ 6.26 (0.83 H, d, J=2.5 Hz, H-1β), 5.62 (0.17 H, dd, J=10.3, 2.1 Hz, H-1α), 5.43 (0.17 H, ddd, J=6.1, 4.4, 1.9 Hz), 5.29-5.27 (1.66 H, m), 5.22 (0.83 H, td, J=10.6, 4.9 Hz), 5.17 (0.83 H, td, J=6.5, 2.7 Hz), 5.11-5.07 (0.34 H, m), 5.03 (0.17 H, ddd, J=6.5, 2.7 Hz), 4.36 (0.17 H, dd, J=12.5, 2.6 Hz), 4.31 (0.83 H, dd, J=12.5, 2.8 Hz), 4.08-3.98 (2.83 H, m), 3.74 (0.17 H, dd, J=10.5, 2.5 Hz), 2.17-2.15 (0.17 H, m), 2.15-2.13 (0.83 H, m), 2.11 (2.49 H, s), 2.10 (0.51 H, s), 2.09 (0.51 H, s), 2.08 (2.49 H, s), 2.07 (0.51 H, s), 2.04 (2.49 H, s), 2.03 (0.51 H, s), 2.017 (2.49 H, s), 2.013 (0.51 H, s), 2.00 (2.49 H, s), 2.00-1.98 (0.83 H, m), 1.98-1.96 (0.17 H, m), 1.88 (2.49 H, s), 1.87 (0.51 H, s).

Example 2

Diethyl (5-acetamido-4-acetoxy-6-(1,2,3-triacetoxy)propyl-3,4,5,6-tetrahydro-2H-pyran-2-yl) phosphonate (4)

The anomeric mixture of 3 (2.15 g, 4.52 mmol) and diethyl trimethylsilyl phosphite (3.11 mL, 13.65 mmol) in anhydrous CH$_2$Cl$_2$ (30 mL) was treated with trimethylsilyl trifluoromethylsulfonate (TMSOTf, 1.23 mL, 6.78 mmol) at 0° C. After 30 min, the mixture was warmed to room temperature, and stirred for 24 h. The mixture was poured into ice water (20 mL), and the aqueous layer was extracted with CH$_2$Cl$_2$ (20 mL, 2×). The combined extracts were washed successively with saturated aqueous NaHCO$_3$ (50 mL) and brine (50 mL), dried over MgSO$_4$, filtered and concentrated. The residue was purified by column chromatography on silica gel (acetone/EtOAc, 1:9) to afford 4 as a colorless syrup (1.55 g, 62%), which contained a mixture of the α- and β-anomers (2:3). The anomeric mixture of phosphonate 4 was used in the next step without further separation. The analytical samples of pure α- and β-anomers (4α and 4β) were obtained by flash column chromatography on silica gel (EtOAc/acetone, 100:0 to 90:10).

α-Anomer 4α: C$_{22}$H$_{36}$NO$_{13}$P; colorless foam; TLC (EtOAc/acetone, 9:1) R$_f$=0.25; (α)$_D^{20}$=+39.4 (c=4.6, CH$_2$Cl$_2$); $^1$H NMR (600 MHz, CDCl$_3$) δ 5.30 (1 H, dd, J=5.7, 1.7 Hz), 5.24 (1 H, d, J=9.9 Hz, NH), 5.18 (1 H, td, J=6.6, 2.5 Hz), 4.98 (1 H, td, J=10.6, 5.0 Hz), 4.40 (1 H, dd, J=12.3, 5.0 Hz), 4.22-4.09 (5 H, m), 3.97 (1 H, q, J=10.1 Hz), 3.74 (1 H, td, J=12.5, 2.4 Hz), 3.62 (1 H, dd, J=10.3, 2.0 Hz), 2.27 (1 H, dd, J=12.8, 4.9 Hz), 2.09 (3 H, s), 2.05 (3 H, s), 2.02 (3 H, s), 2.01 (3 H, s), 1.98-1.92 (1 H, m), 1.87 (3 H, s), 1.35-1.31 (6 H, m); $^{13}$C NMR (150 MHz, CDCl$_3$) δ 170.9 (C), 170.5 (C), 170.3 (C), 170.2 (C), 170.1 (C), 79.0 (CH, d, $^3J_{c-p}$=17.3 Hz), 71.8 (CH, d, $^1J_{c-p}$=174.6 Hz, C-1), 71.6 (CH, d, $^3J_{c-p}$=20.9 Hz), 71.0 (CH), 67.9 (CH), 63.4 (CH$_2$, d, $^2J_{c-p}$=6.9 Hz, POCH$_2$), 62.8 (CH$_2$, d, $^2J_{c-p}$=6.2 Hz, POCH$_2$), 62.2 (CH$_2$, C-8), 49.6 (CH, C-4), 31.3 (CH$_2$, C-2), 23.1 (CH$_3$), 20.9 (CH$_3$), 20.8 (CH$_3$), 20.7 (CH$_3$, 2×), 16.5 (CH$_3$, d, $^3J_{c-p}$=5.4 Hz, POCH$_2$CH$_3$), 16.3 (CH$_3$, d, $^3J_{c-p}$=5.4 Hz, POCH$_2$CH$_3$); $^{31}$P NMR (202 MHz, CDCl$_3$) δ 18.48; HRMS calcd for C$_{22}$H$_{35}$NO$_{13}$P: 552.1846, found: m/z 552.1921 (M−H)$^+$.

β-Anomer 4β: C$_{22}$H$_{36}$NO$_{13}$P; colorless foam; TLC (EtOAc/acetone, 9:1) R$_f$=0.28; (α)$_D^{20}$=−40.1 (c=3.0, CH$_2$Cl$_2$); $^1$H NMR (600 MHz, CDCl$_3$) δ 5.45 (1 H, d, J=10.1 Hz, NH), 5.35 (1 H, dd, J=7.3, 2.3 Hz), 5.32 (1 H, td, J=15.0, 4.8 Hz), 5.21-5.18 (1 H, m), 4.45 (1 H, d, J=10.0 Hz), 4.33 (1 H, dd, J=12.4, 2.8 Hz), 4.30 (1 H, dd, J=12.3, 7.1 Hz), 4.19-4.13 (2 H, m), 4.12-4.04 (4 H, m), 2.35-2.31 (1 H, m), 2.11 (3 H, s), 2.08 (3 H, s), 2.017 (3 H, s), 2.011 (3 H, s), 2.09-2.03 (1 H, m), 1.88 (3 H, s), 1.34 (3 H, t, J=7.0 Hz), 1.33 (3 H, t, J=7.0 Hz); $^{13}$C NMR (150 MHz, CDCl$_3$) δ 170.8 (C), 170.6 (C), 170.2 (C), 170.1 (C), 169.8 (C), 74.0 (CH), 69.7 (CH), 69.5 (CH), 67.9 (CH, d, $^1J_{c-p}$=157.2 Hz, C-1), 67.7 (CH), 63.0 (CH$_2$, d, $^2J_{c-p}$=7.2 Hz, POCH$_2$), 62.7 (CH$_2$, d, $^2J_{c-p}$=6.6 Hz, POCH$_2$), 62.0 (CH$_2$, C-8), 49.0 (CH, C-4), 29.5 (CH$_2$, d, $^2J_{c-p}$=3.2 Hz, C-2), 23.1 (CH$_3$), 21.0 (CH$_3$), 20.9 (CH$_3$), 20.7 (CH$_3$, 2×), 16.2 (CH$_3$, d, $^3J_{c-p}$=5.1 Hz, POCH$_2$CH$_3$), 16.3 (CH$_3$, d, $^3J_{c-p}$=5.1 Hz, POCH$_2$CH$_3$); $^{31}$P NMR (202 MHz, CDCl$_3$) δ 21.36; HRMS calcd for C$_{22}$H$_{35}$NO$_{13}$P: 552.1846, found: m/z 552.1879 (M−H)$^+$.

Example 3

Diethyl (5-acetamido-4-acetoxy-6-(1,2,3-triacetoxy)propyl-4,5,6-trihydropyran-2-yl) phosphonate (5)

The anomeric mixture of phosphonate 4 (1.1 g, 2 mmol) and N-bromosuccinimide (885 mg, 5 mmol) in anhydrous $CH_2Cl_2$ (20 mL) was heated to reflux under irradiation from a 100 W tungsten lamp. The progress of reaction was monitored by TLC. On completion (~6 h) the mixture was cooled to room temperature, and the precipitate succinimide was filtered off. The filtrate was evaporated under reduced pressure to give a crude 2-bromo derivative as yellow syrup, which was used in the next step without further purification.

A solution of the above-prepared bromo compound in anhydrous pyridine (10 mL) was stirred at 50° C. for 2 h. The solution was concentrated under reduced pressure, and the brown residue was purified by column chromatography on silica gel (EtOAc/acetone, 100:0 to 90:10) to afford conjugated phosphonate 5 as colorless foam (827 mg, 75% for two steps). $C_{22}H_{34}NO_{13}P$; TLC (EtOAc/acetone, 9:1) $R_f$=0.28; $(\alpha)_D^{20}$=+43.8 (c=0.59, $CH_2Cl_2$); $^1H$ NMR (600 MHz, $CDCl_3$) δ 5.74 (1 H, dd, J=10.7, 2.2 Hz), 5.54 (1 H, d, J=8.2 Hz, NH), 5.42-5.40 (2 H, m), 5.26 (1 H, td, J=6.4, 2.9 Hz), 4.39-4.34 (2 H, m), 4.29 (1 H, q, J=9.1 Hz), 4.17-4.09 (5 H, m), 2.09 (3 H, s), 2.05 (3 H, s), 2.04 (3 H, s), 2.02 (3 H, s), 1.91 (3 H, s), 1.35 (3 H, t, J=7.0 Hz), 1.31 (3 H, t, J=7.0 Hz); $^{13}C$ NMR (150 MHz, $CDCl_3$) δ 170.8 (C), 170.4 (C), 170.3 (C), 169.8 (C), 169.7 (C), 147.8 (C, d, $^1J_{c-p}$=225 Hz, C-1), 113.0 (CH, d, $^2J_{c-p}$=22.8 Hz, C-2), 76.5 (CH, d, $^3J_{c-p}$=9.3 Hz), 69.9 (CH), 68.4 (CH, d, $^3J_{c-p}$=15.2 Hz), 67.2 (CH), 63.2 ($CH_2$, d, $^2J_{c-p}$=5.4 Hz, $POCH_2$), 63.0 ($CH_2$, d, $^2J_{c-p}$=5.7 Hz, $POCH_2$), 61.8 ($CH_2$, C-8), 46.4 (CH, C-4), 23.0 ($CH_3$), 20.78 ($CH_3$), 20.73 ($CH_3$), 20.63 ($CH_3$), 20.60 ($CH_3$), 16.16 ($CH_3$, d, $^3J_{c-p}$=4.8 Hz, $POCH_2CH_3$), 16.12 ($CH_3$, d, $^3J_{c-p}$=4.8 Hz, $POCH_2\underline{C}H_3$); $^{31}P$ NMR (202 MHz, $CDCl_3$) δ 6.374; HRMS calcd for $C_{22}H_{33}NO_{13}P$: 550.1690, found: m/z 550.1684 $(M-H)^+$.

Example 4

Diethyl (4-(1,2,3-triacetoxy)propyl-2-methyl-3a,7a-dihydro-4H-pyrano(3,4-d)oxazol-6-yl)phosphonate (6)

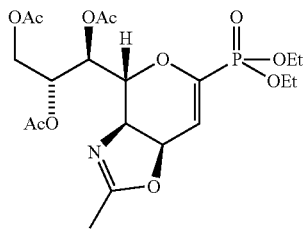 [SMILES: CCOP(=O)(OCC)C1=C[C@H]2OC(C)=N[C@H]2[C@H]([C@H](OC(C)=O)[C@@H](COC(C)=O)OC(C)=O)O1]

To a solution of phosphonate 5 (550 mg, 1 mmol) in a mixture of acetic acid (2 mL) and acetic anhydride (2 mL) was treated with conc. $H_2SO_4$ (0.2 mL). The mixture was stirred for 48 h at room temperature, poured into cold (0° C.) saturated aqueous $NaHCO_3$ (pH 9), and stirred for 30 min before extraction with EtOAc (30 mL, 5×). The combined extracts were dried over $MgSO_4$, filtered and concentrated under reduced pressure. The residual oil was purified by column chromatography on silica gel (acetone/EtOAc, 1:9) to afford 6 as pale yellow syrup (394 mg, 80% for two steps). $C_{20}H_{30}NO_{11}P$; TLC (EtOAc/acetone, 9:1) $R_f$=0.30; $(\alpha)_D^{20}$=−11.6 (c=0.50, $CH_2Cl_2$); $^1H$ NMR (600 MHz, $CDCl_3$) δ 6.20 (1 H, dd, J=10.3, 4.0 Hz), 5.58 (1 H, ddd, J=6.6, 2.9, 1.1 Hz), 5.38 (1 H, td, J=7.7, 2.4 Hz), 4.71 (1 H, ddd, J=8.6, 4.0, 2.0 Hz), 4.40 (1 H, dd, J=12.4, 2.5 Hz), 4.19 (1 H, dd, J=12.5, 5.9 Hz), 4.18-4.07 (4 H, m), 3.93 (1 H, td, J=9.2, 0.6 Hz), 3.34 (1 H, dd, J=10.1, 2.7 Hz), 2.11 (3 H, s), 2.04 (3 H, s), 2.03 (3 H, s), 1.98 (3 H, s), 1.34 (3 H, t, J=7.0 Hz), 1.32 (3 H, t, J=7.0 Hz); $^{13}C$ NMR (150 MHz, $CDCl_3$) δ 170.5 (C), 169.7 (C), 169.4 (C), 167.2 (C, N=$\underline{C}CH_3$), 150.1 (C, d, $^1J_{c-p}$=225 Hz, C-1), 111.9 (CH, d, $^2J_{c-p}$=23.4 Hz, C-2), 76.1 (CH, d, $^3J_{c-p}$=6.3 Hz), 71.2 (CH, d, $^3J_{c-p}$=15.3 Hz), 69.6 (CH), 68.8 (CH), 63.1 ($CH_2$, d, $^2J_{c-p}$=5.9 Hz, $POCH_2$), 62.9 ($CH_2$, d, $^2J_{c-p}$=5.7 Hz, $POCH_2$), 61.8 (CH, C-4), 61.6 ($CH_2$, C-8), 20.7 ($CH_3$), 20.6 ($CH_3$), 20.5 ($CH_3$), 16.2 ($CH_3$, d, $^3J_{c-p}$=5.1 Hz, $POCH_2CH_3$), 16.1 ($CH_3$, d, $^3J_{c-p}$=5.1 Hz, $POCH_2CH_3$), 14.0 ($CH_3$, N=$CCH_3$); $^{31}P$ NMR (202 MHz, $CDCl_3$) δ 6.375; HRMS calcd for $C_{20}H_{29}NO_{11}P$: 490.1478, found: m/z 490.1374 $(M-H)^+$.

Example 5

Diethyl (5-acetamido-4-azido-6-(1,2,3-triacetoxy) propyl-4,5,6-trihydropyran-2-yl) phosphonate (7)

To a solution of oxazoline 6 (393 mg, 0.8 mmol) in t-BuOH (10 mL) was treated with azidotrimethylsilane (0.53 mL, 4 mmol) at 80° C. for 24 h. The solution was poured into saturated aqueous $NaHCO_3$, and extracted with EtOAc (30 mL, 3×). The combined extracts were dried over $MgSO_4$, filtered and concentrated to afford the azido compound 7 as a colorless syrup (371 mg, 87%), which was practically pure to be used in the next step. An analytical sample was obtained by flash column chromatography on silica gel (10% acetone in EtOAc). $C_{20}H_{31}N_4O_{11}P$; TLC (EtOAc/acetone, 9:1) $R_f$=0.30; $(\alpha)_D^{20}$=+82.7 (c=0.58, $CH_2Cl_2$); $^1H$ NMR (600 MHz, $CDCl_3$) δ 5.75 (1 H, dd, J=10.3, 2.4 Hz), 5.73 (1 H, d, J=8.6 Hz), 5.38 (1 H, dt, J=7.1, 1.5 Hz), 5.26 (1 H, ddd, J=8.5, 5.8, 2.6 Hz), 4.53-4.50 (2 H, m), 4.36 (1 H, dd, J=12.5, 2.6 Hz), 4.17-4.08 (5 H, m), 3.67 (1 H, q, J=9.2 Hz), 2.10 (3 H, s), 2.05 (3 H, s), 2.02 (3 H, s), 1.99 (3 H, s), 1.34 (3 H, t, J=7.1 Hz), 1.32 (3 H, t, J=7.1 Hz); $^{13}C$ NMR (150 MHz, $CDCl_3$) δ 170.8 (C), 170.5 (C), 170.1 (C), 169.7 (C), 147.7 (C, d, $^1J_{c-p}$=224 Hz, C-1), 112.4 (CH, d, $^2J_{c-p}$=22.9 Hz, C-2), 75.9 (CH, d, $^3J_{c-p}$=9.2 Hz), 69.7 (CH), 67.3 (CH), 63.5 ($CH_2$, d, $^2J_{c-p}$=5.7 Hz, $POCH_2$), 63.3 ($CH_2$, d, $^2J_{c-p}$=5.9 Hz, $POCH_2$), 61.9 ($CH_2$, C-8), 57.8 (CH, d, $^3J_{c-p}$=14.7 Hz), 48.5 (CH, C-4), 23.2 ($CH_3$), 20.8 ($CH_3$), 20.77 ($CH_3$), 20.71 ($CH_3$), 16.27 ($CH_3$, d, $^3J_{c-p}$=5.7 Hz, $POCH_2CH_3$), 16.23 ($CH_3$, d, $^3J_{c-p}$=5.7 Hz, $POCH_2\underline{C}H_3$).

Example 6

Diethyl {5-acetamido-4-($N^2$,$N^3$-bis(tert-butoxycarbonyl))guanidino-6-(1,2,3-triacetoxy)propyl-4,5,6-trihydropyran-2-yl}phosphonate (8)

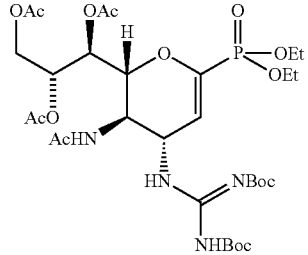

A solution of azide 7 (350 mg, 0.71 mmol) in ethanol (25 mL) was hydrogenated with Lindlar catalyst (30 mg) under an atmosphere of hydrogen. The mixture was stirred for 5 h, filtered through a pad of Celite, and washed with ethanol. The filtrate was concentrated under reduced pressure to give a colorless foam (278 mg). The crude amine product was dissolved in anhydrous $CH_2Cl_2$ (30 mL) and treated with 1,3-bis(tert-butoxycarbonyl)-2-methylthiopseudourea (247 mg, 0.85 mmol) and $Et_3N$ (230 μL, 1.7 mmol). The mixture was cooled to 0° C., and $HgCl_2$ (231 mg, 0.85 mmol) was added slowly. The suspension was warmed to room temperature and stirred for 12 h. After which the mixture was diluted with EtOAc and filtered through a pad of Celite. The filtrate was concentrated and purified by flash column chromatography (EtOAc) to afford guanidine 8 (442 mg, 83% yield) as a colorless foam. TLC (EtOAc) $R_f$=0.45; $(\alpha)_D^{20}$=+18.5 (c=0.88, $CH_2Cl_2$); $^1H$ NMR (600 MHz, $CDCl_3$) δ 11.32 (1 H, s), 8.48 (1 H, d, J=8.5 Hz), 6.12 (1 H, d, J=8.5 Hz), 5.71 (1 H, dd, J=10.3, 2.0 Hz), 5.35 (1 H, d, J=6.6 Hz), 5.23 (1 H, td, J=6.5, 2.7 Hz), 5.10-5.06 (1 H, m), 4.37 (1 H, dd, J=12.5, 2.8 Hz), 4.25-4.20 (2 H, m), 4.19-4.12 (2 H, m), 4.12-4.05 (3 H, m), 2.09 (3 H, s), 2.06 (3 H, s), 2.02 (3 H, s), 1.85 (3 H, s), 1.46 (9 H, s), 1.45 (9 H, s), 1.36 (3 H, t, J=7.1 Hz), 1.31 (3 H, t, J=7.1 Hz); $^{13}C$ NMR (150 MHz, $CDCl_3$) δ 171.0 (C), 170.5 (C), 170.1 (C), 169.8 (C), 162.7 (C), 157.2 (C), 152.6 (C), 147.4 (C, d, $^1J_{c-p}$=224 Hz, C-1), 114.2 (CH, d, $^2J_{c-p}$=23.3 Hz, C-2), 83.9 (C), 79.8 (C), 77.9 (CH, d, $^3J_{c-p}$=9.3 Hz), 70.1 (CH), 67.4 (CH), 63.4 ($CH_2$, d, $^2J_{c-p}$=5.7 Hz, $POCH_2$), 63.0 ($CH_2$, d, $^2J_{c-p}$=5.7 Hz, $POCH_2$), 62.1 ($CH_2$, C-8), 49.0 (CH, d, $^3J_{c-p}$=15.2 Hz), 48.1 (CH, C-4), 28.2 ($CH_3$, 3×), 28.0 ($CH_3$, 3×), 23.1 ($CH_3$), 20.9 ($CH_3$), 20.8 ($CH_3$), 20.7 ($CH_3$), 16.29 ($CH_3$, $POCH_2CH_3$), 16.25 ($CH_3$, $POCH_2CH_3$); HRMS calcd for $C_{31}H_{50}N_4O_{15}P$ (M$^+$–H): 749.3010, found: m/z 749.3172.

Example 7

(5-Acetamido-4-amino-6-(1,2,3-hydroxy)propyl-4,5,6-trihydropyran-2-yl) phosphonic acid (1a)

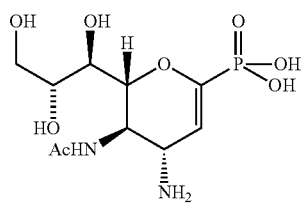 [SMILES: CC(=O)N[C@H]1[C@H]([C@H](O)[C@H](O)CO)OC(P(=O)(O)O)=C[C@@H]1N]

A solution of diethyl phosphonate 7 (80 mg, 0.15 mmol) in anhydrous $CH_2Cl_2$ (4 mL) at 0° C. was treated with bromotrimethylsilane (0.12 mL, 0.87 mmol). After stirring for 24 h at 0° C., MeOH (2 mL) was added, and the mixture was concentrated under reduced pressure. The residue was dissolved in anhydrous MeOH (5 mL) and treated with sodium methoxide (5.4 M solution in MeOH, 0.9 mL, 4.86 mmol). After stirring for 1 h at room temperature, the mixture was filtered through Dowex 50WX8 (H$^+$ form), and then concentrated under reduced pressure. The residue was dissolved in MeOH (5 mL) and subjected to hydrogenation (1 atm) in the presence of Lindlar's catalyst (20 mg) at room temperature. After 3 h, the mixture was filtered through a pad of Celite, and rinsed with MeOH. The filtrate was concentrated, and the residual solids were washed with $Et_2O$ (3×10 mL) to afford the phosphonate 1a.

Example 8

(5-Acetamido-4-guanidino-6-(1,2,3-hydroxy)propyl-4,5,6-trihydropyran-2-yl) phosphonic acid (1b)

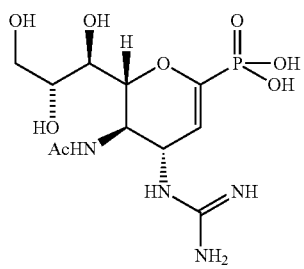 [SMILES: CC(=O)N[C@H]1[C@H]([C@H](O)[C@H](O)CO)OC(P(=O)(O)O)=C[C@@H]1NC(=N)N]

A solution of diethyl phosphonate 8 (130 mg, 0.17 mmol) in anhydrous $CH_2Cl_2$ (4 mL) was treated with bromotrimethylsilane (0.13 mL, 0.94 mmol) at 0° C., and the reaction mixture was stirred for 24 h at 0° C. MeOH (2 mL) was added under vigorous stirring. After 30 min, the solution was evaporated under reduced pressure and the residue as a solution in anhydrous MeOH (5 mL) was treated with a 5.4 M solution of sodium methoxide in methanol (1 mL, 5.4 mmol). After stirring for 1 h at room temperature, the solution was filtered through Dowex 50WX8 (H$^+$ form) and subjected to lyophilisation. The residual pale yellow solid was washed with $Et_2O$ (3×20 mL) to afford the phosphonate 1b as a white solid.

Example 9

(5-Acetamido-4-amino-6-(1,2,3-hydroxy)propyl-4,5,6-trihydropyran-2-yl) phosphonic acid monoethyl ester (1c)

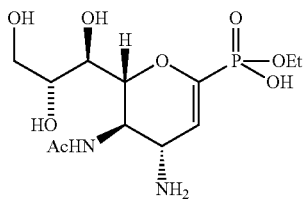 [SMILES: CCOP(=O)(O)C1=C[C@H](N)[C@@H](NC(C)=O)[C@H]([C@H](O)[C@H](O)CO)O1]

Under an atmosphere of argon, a solution of $PMe_3$ (1.4 mL, 1.4 M in THF) was added dropwise to a solution of azide 7 (148 mg, 0.28 mmol) in anhydrous THF (5 mL) at 0° C. The mixture was stirred at room temperature for 19 h. $Et_3N$ (0.5 mL) and $H_2O$ (0.5 mL) was added, and the mixture was stirred for another 30 min. The mixture was concentrated under reduced pressure, and purified by silica gel column chromatography (MeOH/$CH_2Cl_2$, 6:94 to 10:90) to afford an amine product (112 mg, 79% yield).

The amine product (110 mg, 0.22 mmol) was dissolved in EtOH (2 mL), and a solution of NaOEt (490 μL, 2.68 M in EtOH) was added dropwise. The mixture was stirred for 2 days and monitored by TLC. After neutralized by Dowex 50W resin, the filtrate was concentrated under reduced pressure, and subjected to silica gel column chromatography (n-PrOH/H$_2$O, 7:3). The appropriate fractions were collected and concentrated under reduced pressure. The residue was treated with 1 M HCl (2 mL), and then concentrated in vacuo to give phosphonate monoester 1c (50 mg, 60% yield). $C_{12}H_{23}N_2O_8P$: $^1$H NMR (600 MHz, D$_2$O) δ 5.48 (1 H, dd, J=9.4, 7.6 Hz), 4.38-4.33 (2 H, m), 4.18-4.17 (1 H, m), 3.98-3.93 (2 H, m), 3.91-3.86 (2 H, m), 3.69-3.64 (2 H, m), 2.07 (3 H, s), 1.26 (3 H, t, J=7.1 Hz); $^{13}$C NMR (150 MHz, D$_2$O) δ 174.7, 153.3 (d, $^1J_{C-P}$=208.8 Hz), 104.3 (d, $^2J_{C-P}$=22.5 Hz), 75.4 (d, $^3J_{C-P}$=8.0 Hz), 69.6, 67.6, 62.9, 62.2 (d, $^2J_{C-P}$=5.1 Hz), 49.9 (d, $^3J_{C-P}$=13.4 Hz), 45.8, 22.1, 15.8 (d, $^3J_{C-P}$=5.7 Hz); HRMS calcd for $C_{12}H_{22}N_2O_8P$: 353.1108, found: m/z 353.1198 [M−H]$^-$.

Example 10

(5-Acetamido-4-guanidino-6-(1,2,3-hydroxy)propyl-4,5,6-trihydropyran-2-yl) phosphonic acid monoethyl ester (1d)

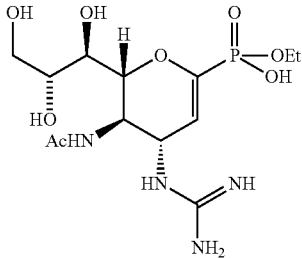 [SMILES: CCOP(=O)(O)C1=C[C@H](NC(=N)N)[C@@H](NC(C)=O)[C@H]([C@H](O)[C@H](O)CO)O1]

Compound 8 (52 mg, 0.07 mmol) was dissolved in EtOH (1 mL) and a solution of NaOEt (209 μL, 2.68 M in EtOH) was added dropwise. The mixture was stirred for 4 days and monitored by TLC. After neutralized by Dowex 50W resin, the filtrate was concentrated under reduced pressure, and subjected to silica gel column chromatography (n-PrOH/H$_2$O, 8:2). The appropriate fractions were collected and concentrated under reduced pressure. The residue was treated with 1 M HCl (2 mL), and then concentrated in vacuo to give phosphonate monoester 1d (9 mg, 30% yield). $C_{13}H_{25}N_4O_8P$: $^1$H NMR (600 MHz, D$_2$O) δ 5.41 (1 H, dd, J=9.4, 7.5 Hz), 4.42-4.40 (1 H, m), 4.35 (1 H, d, J=10.6 Hz), 4.21 (1 H, t, J=9.9 Hz), 3.97-3.93 (2 H, m), 3.90-3.85 (2 H, m), 3.67-3.62 (2 H, m), 2.01 (3 H, s), 1.25 (3 H, t, J=7.1 Hz); $^{13}$C NMR (150 MHz, D$_2$O) δ 174.3, 156.9, 151.3 (d, $^1J_{C-P}$=211.2 Hz), 108.2 (d, $^2J_{C-P}$=21.6 Hz), 75.8, (d, $^3J_{C-P}$=8.6 Hz), 69.7, 67.9, 62.9, 62.1 (d, $^2J_{C-P}$=4.8 Hz), 50.9 (d, $^3J_{C-P}$=13.7 Hz), 47.8, 21.9, 15.8 (d, $^3J_{C-P}$=5.7 Hz).

Example 11

Synthesis of Zanamivir Biotin Conjugate

Figure 3:
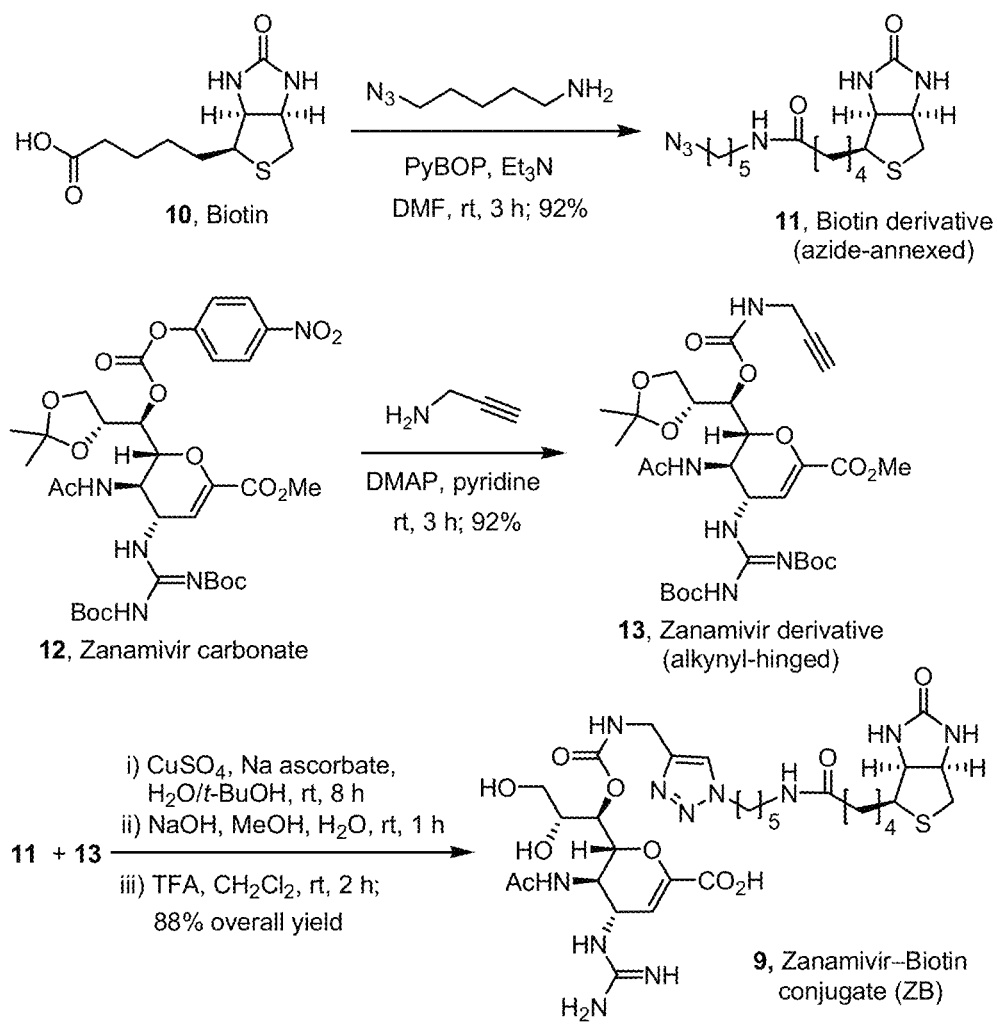
FIG. 3 shows a scheme for synthesis of zanamivir-biotin conjugate (ZB, 9).

FIG. 3 shows the synthesis of zanamivir-biotin conjugate 9. The azide-annexed biotin derivative 11 was prepared by condensation of biotin (10) with 5-azido-1-pentylamine in the presence of triethylamine and benzotriazol-1-yl-oxytripyrrolidinophosphonium hexafluorophosphate (PyBOP). (J. W. Lee, S. I. Jun, K. Kim, Tetrahedron Lett. 42, 2709 (2001)). On the other hand, zanamivir p-nitrophenyl carbonate 12, prepared from sialic acid according to the known procedure, (M. Chandler et al., J. Chem. Soc., Perkin Trans. 1: 1173 (1995); L. Ying, J. Gervay-Hague, ChemBioChem 6, 1857 (2005)) was coupled with propargylamine to afford the zanamivir derivative 13 with an alkynyl hinge. (W.-H. Wen et al., J. Med. Chem. 52, 4903 (2009)). The subsequent 1,3-dipolar addition (click reaction; V. V. Rostovtsev et al., Angew. Chem., Int. Ed. 41, 2596 (2002); B.-Y. Lee et al., Tetrahedron Lett. 47, 5105 (2006)) between the azide-annexed biotin derivative 11 and the alkynyl zanamivir derivative 13 was conducted in a mixed solvent of CH$_2$Cl$_2$/H$_2$O (1:1) to give the desired zanamivir-biotin conjugate 9 in 88% overall yield after removal of the protecting groups.

Example 12

Biotin Derivative 11

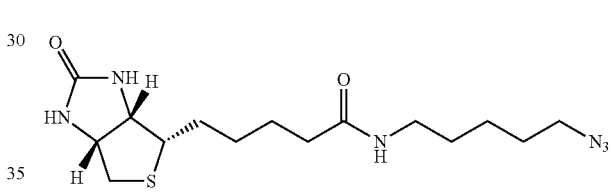

A solution of PPh$_3$ (5.0 g, 19.1 mmol) and 1,5-diazidopentane (3.36 g, 21.8 mmol), prepared from the substitution reaction of 1,5-dibromopentane with NaN3, was vigorously stirred with 5% aqueous HCl (22 mL) in EtOAc/Et2O (v/v=1:1, 35 mL) at room temperature for 24 h to give 5-azido-1-pentylamines1 (1.60 g, 59%). (J. W. Lee, S. I. Jun, K. Kim, Tetrahedron Lett. 42, 2709 (2001).)

A sample of biotin (10, 136 mg, 0.56 mmol) was stirred with 5-azido-1-pentylamine (11, 86 mg, 0.69 mmol), benzotriazol-1-yl-oxytripyrrolidinophosphonium hexafluorophosphate (PyBOP, 360 mg, 0.69 mmol) and Et3N (0.116 mL, 0.84 mol) in DMF solution (5 mL) at room temperature for 3 h. The mixture was concentrated under reduced pressure, and washed with H2O. The residue was purification by silica gel chromatography (CH2Cl2/MeOH=15:1) to give the azide-annexed biotin derivative 11 (180 mg, 92%). C15H26N6O2S; colorless solid, mp 121-122° C.; [α]19D +87.6 (c 0.0275, MeOH); IR vmax (neat) 3297, 2924, 2100, 1698, 1647 cm-1; 1H NMR (400 MHz, CDCl3) δ 7.34 (1 H, t, J=5.2 Hz), 6.40 (1 H, s), 6.34 (1 H, s), 4.30-4.27, (1 H, m), 4.12-4.09 (1 H, m), 3.29 (2 H, t, J=6.8 Hz), 3.10-3.05 (1 H, m), 3.03-2.98 (2 H, m), 2.80 (1 H, dd, J=12.4, 5.2 Hz), 2.56 (1 H, d, J=12.4 Hz), 2.03 (2 H, t, J=7.2 Hz), 1.64-1.22 (12 H, m); $^{13}$C NMR (100 MHz, DMSO) δ 171.5, 162.4, 61.0, 59.1, 55.4, 50.6, 39.8, 38.1, 35.2, 28.7, 28.3, 28.1, 28.0, 25.4, 23.6; ESI-HRMS calculated for $C_{15}H_{27}N_6O_2S$: 355.1916, found: m/z 355.1913 [M+H]$^+$.

Example 13

Zanamivir-Biotin Conjugate 9

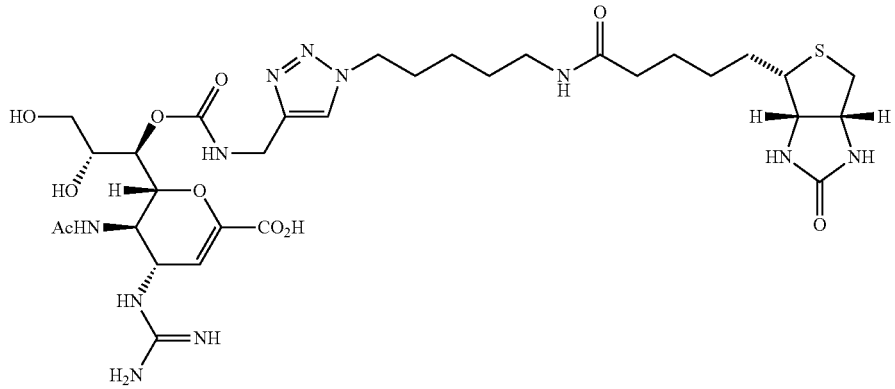

A solution of the azide-annexed biotin derivative 11 (100 mg, 0.28 mol), and the alkynyl-hinged zanamivir derivative 13 (188 mg, 0.28 mmol) was stirred with $CuSO_4 \cdot 5H_2O$ (10 mg, 0.04 mmol) and sodium ascorbate (25 mg, 0.13 mmol) in $CH_2Cl_2/H_2O$ (6 mL, v/v=1:1) at room temperature for 8 h. The aqueous layer was extracted with $CH_2Cl_2$. The organic layer was combined, dried over $MgSO_4$, filtered, and concentrated by rotary evaporation under reduced pressure. The residue was purified by column chromatography ($CH_2Cl_2$/MeOH=20:1 to 10:1) to afford a zanamivir-biotin conjugate containing protective groups (270 mg, 95%). $C_{45}H_{71}N_{11}O_{14}S$; TLC ($CH_2Cl_2$/MeOH=9:1) $R_f$=0.29; colorless solid, mp 157-158° C.; $[\alpha]^{22}_D$ +16.6 (c 0.5, $CH_2Cl_2$); IR $v_{max}$ (neat) 2930, 1727, 1689, 1643, 1612 cm$^{-1}$; $^1$H NMR (400 MHz, CDCl$_3$) δ 11.37 (1 H, s), 8.20 (1 H, d, J=7.6 Hz), 8.04 (1 H, d, J=9.2 Hz), 7.95 (1 H, s), 7.76-7.70 (2 H, m), 6.40 (1 H, s), 6.33 (1 H, s), 5.81 (1 H, d, J=2.0 Hz), 5.17 (1 H, d, J=5.6 Hz), 4.79 (1 H, t, J=7.6 Hz), 4.36 (1 H, d, J=11.6 Hz), 4.30-4.21 (4 H, m), 4.15-4.10 (3 H, m), 4.04-3.97 (2 H, m), 3.86 (1 H, dd, J=8.8, 5.6 Hz), 3.71 (3 H, s), 3.10-3.05 (1 H, m), 3.00-2.95 (2 H, m), 2.80 (1 H, dd, J=12.4, 5.2 Hz), 2.56 (1 H, d, J=12.4 Hz), 2.02 (2 H, t, J=7.2 Hz), 1.80-1.77 (2 H, m), 1.74 (3 H, s), 1.64-1.19 (10 H, m), 1.45 (9 H, s), 1.39 (9 H, s), 1.25 (6 H, s); $^{13}$C NMR (100 MHz, CDCl$_3$) δ 173.0, 170.7, 163.7, 162.8, 161.8, 156.7, 155.6, 152.4, 145.4, 144.6, 122.9, 110.1, 108.6, 83.6, 79.6, 77.5, 77.2, 75.1, 69.9, 65.7, 61.9, 60.2, 55.8, 53.5, 52.5, 50.0, 49.5, 47.4, 40.6, 38.9, 37.0, 35.8, 29.6, 28.6, 28.3 (3×), 28.1 (3×), 26.5, 25.6, 25.5, 23.5, 23.2; ESI-HRMS calcd for $C_{45}H_{72}N_{11}O_{14}S$: 1022.4981, found: m/z 1022.4986 [M+H]$^+$.

A sample of the protected zanamivir-biotin conjugate (34 mg, 0.033 mmol) was treated with aqueous NaOH (1 M, 1 mL) in MeOH (1 mL) at room temperature for 15 min. The mixture was neutralized with Dowex 50W×8 (H$^+$), filtered, and concentrated under reduced pressure. The residue was then stirred with trifluoroacetic acid (TFA, 1 mL) in $CH_2Cl_2$ (1 mL) at room temperature for 1.5 h. The mixture was evaporated under reduced pressure, and $H_2O$ (1 mL) was added at room temperature. After stirring for 10 min, the mixture was concentrated under reduced pressure, and purified by chromatography on a Sephadex G-10 column (eluent: 0.1% TFA in $H_2O$) to give the desired zanamivir-biotin derivative 9 (24 mg, 93%). $C_{31}H_{49}N_{11}O_{10}S$; colorless solid, mp 170-172° C.; IR $v_{max}$ (neat) 3355, 2937, 1675 cm$^{-1}$; $^1$H NMR (400 MHz, CDCl$_3$) δ 7.92 (1 H, s), 5.96 (1 H, s), 4.98 (1 H, d, J=8.4 Hz), 4.61-4.57 (2 H, m), 4.47-4.39 (5 H, m), 4.33-4.29 (1 H, m), 4.16 (1 H, t, J=9.2 Hz), 4.06-4.04 (1 H, m), 3.65 (1 H, d, J=9.6 Hz), 3.47 (1 H, dd, J=6.4, 12.0 Hz), 3.31 (1 H, m), 3.20-3.10 (2 H, m), 2.98 (1 H, dd, J=4.8, 13.2 Hz), 2.77 (1 H, d, J=13.2 Hz), 2.22 (2 H, t, J=7.2 Hz), 1.97 (3 H, s), 1.93-1.90 (2 H, m), 1.73-1.51 (6 H, m), 1.38-1.22 (4 H, m); $^{13}$C NMR (100 MHz, CDCl$_3$) δ 176.4, 173.8, 165.3, 164.9, 162.9 ($CO_2$ of TFA, q, J=35.0 Hz), 157.0, 156.5, 124.1, 116.5 ($CF_3$ of TFA, q, J=288.1 Hz), 109.1, 75.9, 70.2, 69.0, 62.6, 62.4, 60.5, 55.7, 51.3, 50.8, 47.4, 40.0, 39.2, 36.0, 35.8, 29.4, 29.3, 28.2, 28.1, 28.0, 25.5, 23.3, 22.2; ESI-HRMS calculated for $C_{31}H_{50}N_{11}O_{10}S$: 768.3463, found: m/z 768.3458 [M+H]$^+$.

Example 14

Compound 14

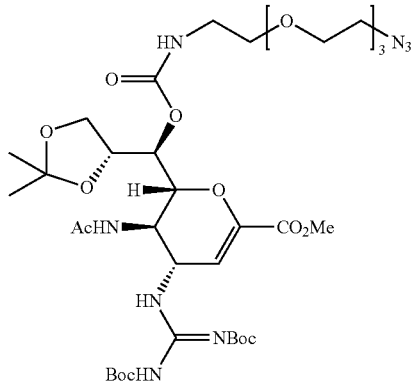

To a solution of carbonate 12 (0.25 g, 0.33 mmol), 4-dimethylaminopyridine (DMAP, 60 mg, 0.50 mmol) in pyridine (2 mL) was added an amine $H_2N(CH_2CH_2O)_3CH_2CH_2N_3$ (0.14 g, 0.66 mmol). The mixture was stirred for 40 h at room temperature under an atmosphere of $N_2$, and then extracted with HCl (10 mL of 1 M aqueous solution) and EtOAc (50 mL). The organic layer was washed with brine (30 mL) and saturated $NaHCO_3(a_q)$ (30 mL), dried over MgSO4, and concentrated under reduced pressure. The residue was purified by column chromatography (silica gel, EtOAc/hexane=1:1) to give carbamate 14 (0.2 g, 74%). $C_{35}H_{58}N_8O_{15}$; $^1$H NMR (CDCl3, 600 MHz) δ 11.41 (1 H, s), 8.45 (1 H, d, J=9 Hz), 6.08 (1 H, d, J=9 Hz), 5.91 (1 H, s), 5.45 (1 H, t, J=6 Hz), 5.26 (1 H, t, J=10 Hz), 5.22 (1 H, d, J=6 Hz), 4.41 (1 H, d, J=9 Hz), 4.38 (1 H, q, J=10, 6 Hz), 4.10-4.14 (2 H, m), 3.81 (3 H, s), 3.60-3.77 (12 H, m), 3.56-3.57 (1 H, m), 3.41 (2 H, t, J=5 Hz), 3.37 (2 H, d, J=5 Hz), 1.92 (3 H, s), 1.50 (18 H, s), 1.41 (3 H, s), 1.37 (3 H, s); 13C NMR (CDCl$_3$) δ 170.6, 163.0, 161.9, 156.9, 155.6, 152.7, 145.2, 132.1, 132.0, 131.9, 128.5, 128.4, 109.8, 108.9, 83.6, 79.6, 77.4, 74.5, 70.6, 70.5, 70.2, 70.0, 69.7, 66.0, 60.4, 52.4, 50.6, 48.7, 48.3, 41.0, 28.2, 28.0, 26.6, 25.4, 23.1; ESI-HRMS calcd for C35H59N8O15: 831.4100, found: m/z 831.4134 [M+H]$^+$.

Example 15

Zanamivir-FITC Conjugate 15

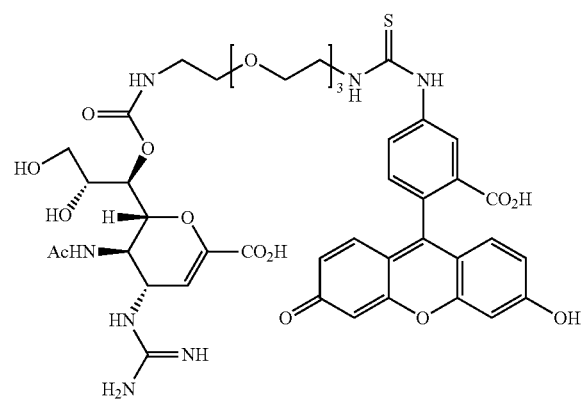

To a solution of azide 14 (80 mg, 0.096 mmol) in EtOH (1 mL) was added Pd(OH)$_2$ (9 mg, 0.058 mmol). The mixture was stirred for 1.5 h at room temperature under an atmosphere of H$_2$, and then filtered through a pad of Celite by elution with MeOH. The mixture was concentrated under reduced pressure to give an amine product (66 mg). $C_{35}H_{60}N_6O_{15}$; $^1$H NMR (CDCl$_3$, 600 MHz) δ 11.36 (1 H, s), 8.40 (1 H, d, J=8 Hz), 6.18 (1 H, d, J=9 Hz), 6.04 (1 H, s), 5.87 (1 H, s), 5.17-5.22 (1 H, m), 4.32-4.39 (2 H, m), 3.98-4.10 (3 H, m), 3.75 (3 H, s), 3.55-3.72 (12 H, m), 3.31 (4 H, s), 2.89 (1 H, s), 2.73 (1 H, d, J=7 Hz), 1.88 (3 H, s), 1.45 (18 H, s), 1.36 (3 H, s), 1.32 (3 H, s).

Under an atmosphere of N$_2$, fluorescene thiocyanate (FITC, 37 mg, 0.095 mmol) was added to a solution of the above-prepared amine compound in anhydrous THF (1 mL). The mixture was stirred for 4 h at room temperature, concentrated under reduced pressure, and purified by column chromatography (silica gel, CH$_2$Cl$_2$/MeOH=92:8) to give a conjugation product (50 mg, 52%). $C_{56}H_{71}N_7O_{20}S$; $^1$H NMR (MeOD, 600 MHz) δ 7.80 (1 H, s), 7.56-7.59 (2 H, m), 7.48 (1 H, t, J=8 Hz), 7.17 (1 H, d, J=8 Hz), 7.09 (1 H, d, J=8 Hz), 6.63 (2 H, s), 6.56 (2 H, d, J=9 Hz), 6.48-6.51 (3 H, m), 5.86 (1 H, d, J=8 Hz), 4.30 (1 H, t, J=10 Hz), 4.12-4.23 (2 H, m), 4.07-4.10 (2 H, m), 3.96-4.06 (2 H, m), 3.93 (1 H, t, J=8 Hz), 3.60-3.77 (15 H, m), 3.44-3.58 (4 H, m), 3.16-3.24 (2 H, m), 1.82 (3 H, s), 1.40-1.42 (18 H, m), 1.32 (3 H, s), 1.30 (3 H, s).

A solution of the above-prepared FITC conjugate (47 mg, 0.039 mmol) in MeOH (1.5 mL) was treated with NaOH (1 mL of 1 M aqueous solution). The mixture was stirred for 1 h at room temperature, neutralized with Dowex 50w×8 (H$^+$), and filtered. The filtrate was concentrated, and the residue was treated with trifluoroacetic acid (TFA, 1 mL) in CH$_2$Cl$_2$ (1 mL). The mixture was stirred for 1 h, concentrated under reduced pressure, and purified by chromatography on a Sephadex G-10 column (eluent: 0.1% TFA in H$_2$O) to give the desired zanamivir-FITC conjugate 15 (10 mg, 56%). $C_{38}H_{41}N_7O_{14}S$; $^1$H NMR (MeOD, 600 MHz) δ 8.31 (1 H, s), 7.88 (1 H, d, J=8 Hz), 7.48-7.57 (3 H, m), 7.30 (1 H, s), 7.36 (1 H, s), 7.13 (2 H, d, J=9 Hz), 6.00 (1 H, s), 4.30-4.32 (1 H, m), 4.10-4.12 (2 H, m), 3.81-3.97 (2 H, m), 3.58-3.80 (14 H, m), 3.13-3.28 (3 H, m), 1.80 (3 H, s).

Example 16

Zanamivir-FITC Conjugate 17

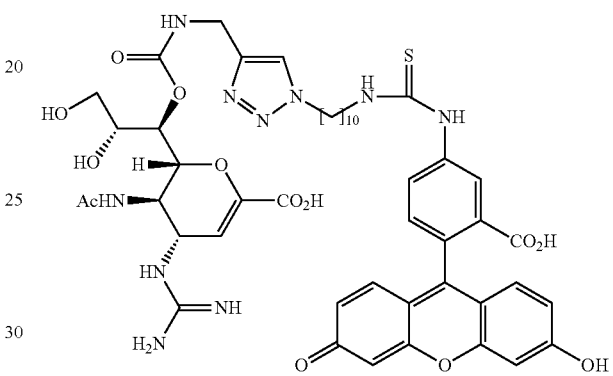

To a solution of alkyne 13 (87 mg, 0.13 mmol) and 10-azidodecanamine (30 mg, 0.16 mmol) in t-BuOH (1 mL) and H$_2$O (1 mL) were added CuSO$_4$.5H$_2$O (4 mg, 0.016 mmol), sodium ascorbate (18 mg, 0.091 mmol) and tris[(1-benzyl-1H-1,2,3-triazol-4-yl)methyl]amine (TBTA, 8 mg, 0.04 mmol). The mixture was stirred for 12 h at room temperature, and then extracted with CH$_2$Cl$_2$ (30 mL) and H$_2$O (30 mL). The organic layer was dried over MgSO$_4$, concentrated under reduced pressure, and purified by column chromatography (silica gel, CH$_2$Cl$_2$/MeOH=9:1) to give compound 16 (53 mg, 50%). $C_{40}H_{67}N_{19}O_{12}$; yellow solid, mp=116° C. $^1$H NMR (CDCl$_3$, 600 MHz) δ 11.38 (1 H, s), 8.43 (1 H, d, J=8 Hz), 7.84 (1 H, br s), 5.88 (1 H, d, J=14 Hz), 5.11-5.28 (2 H, m), 4.33-4.45 (6 H, m), 4.18 (1 H, s), 4.08 (1 H, s), 3.99 (1 H, s), 3.76 (3 H, s), 1.89 (3 H, s), 1.31 (18 H, s), 1.23 (22 H, s).

To a solution of the above-prepared amine (0.1 g, 0.115 mmol) in THF (1 mL) and MeOH (2 mL) were added FITC (45 mg, 0.115 mmol) and diisopropylethylamine (0.038 mL). The mixture was stirred at room temperature for 20 h, and then concentrated under reduced pressure to give a conjugation product as red solids. A solution of the above-prepared conjugation compound in MeOH (1 mL) was stirred with NaOH (1 mL of 1 M aqueous solution) for 1 h at room temperature, neutralized by Dowex 50w×8 (H$^+$), and filtered. After concentration, the residue was dissolved in CH$_2$Cl$_2$ (1 mL) and TFA (1 mL). The mixture was stirred for 30 min at room temperature, concentrated under reduced pressure, and purified by chromatography on a Sephadex G-10 column (eluent: 0.1% TFA in H$_2$O) to give the desired zanamivir-FITC conjugate 17 (50 mg, 43%). $C_{47}H_{56}N_{10}O_{13}S$; yellow solid, mp=112° C.; $^1$H NMR (d-MeOD, 600 MHz) δ 8.13 (1 H, d, J=7 Hz), 7.63-7.67 (4 H, m), 7.55-7.58 (3 H, m), 6.89 (1 H, d, J=7 Hz), 4.54 (1 H, br s), 4.31-4.38 (2 H, m), 4.17 (1 H, s), 4.00 (1 H, br s), 3.58-3.68 (12 H, m), 3.56 (2 H, t, J=5 Hz), 3.42-3.47 (2 H, m), 2.00 (3 H, s), 1.70-1.72 (4H, m), 1.18-

1.36 (12H, m); ESI-HRMS calcd for $C_{47}H_{57}N_{10}O_{13}S$: 1001.3827; found: m/z 1001.3768 [M+H]$^+$.

Example 17

Synthesis of Tamiphosphor-Biotin Conjugate

Figure 4:
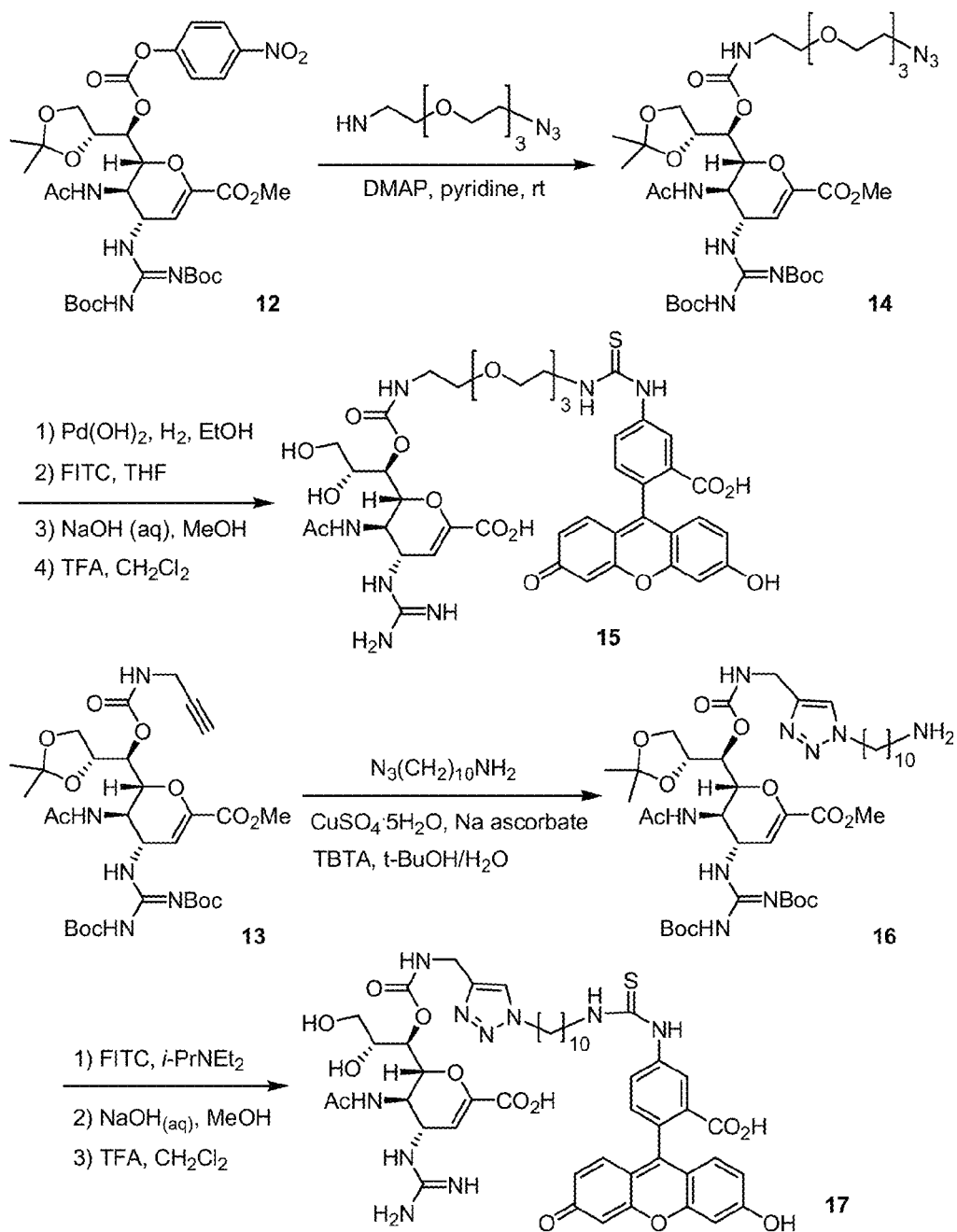
FIG. 4 shows a scheme for synthesis of zanamivir-fluorescene conjugates 15 and 17.
Figure 5:
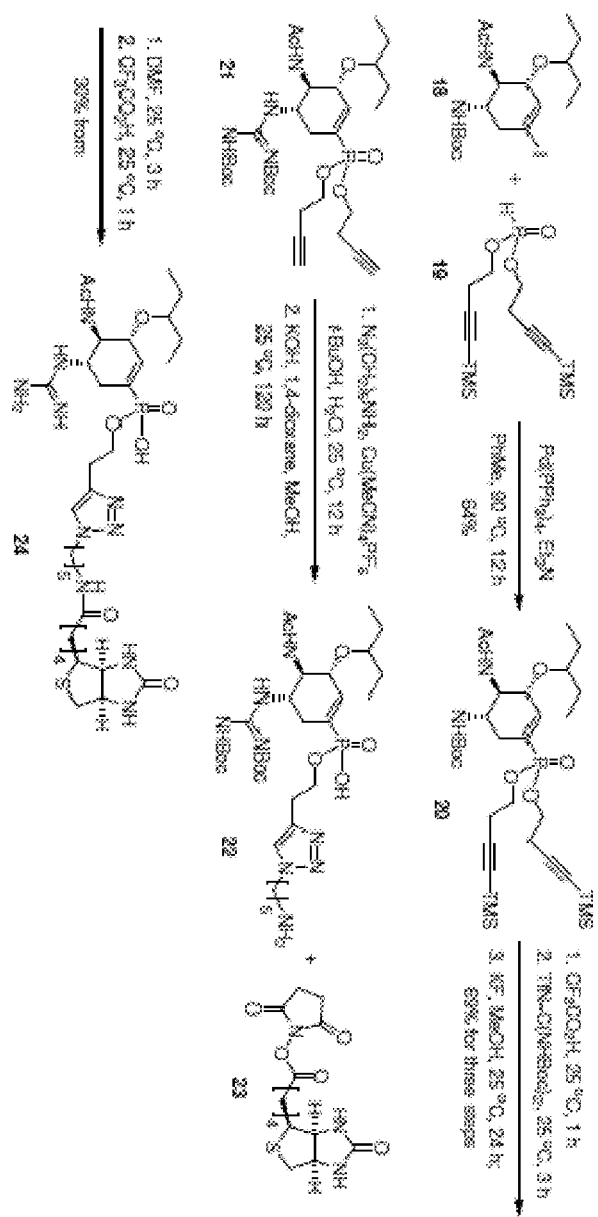
FIG. 5 shows a scheme for synthesis of tamiphosphor-biotin conjugate 24
Figure 6:
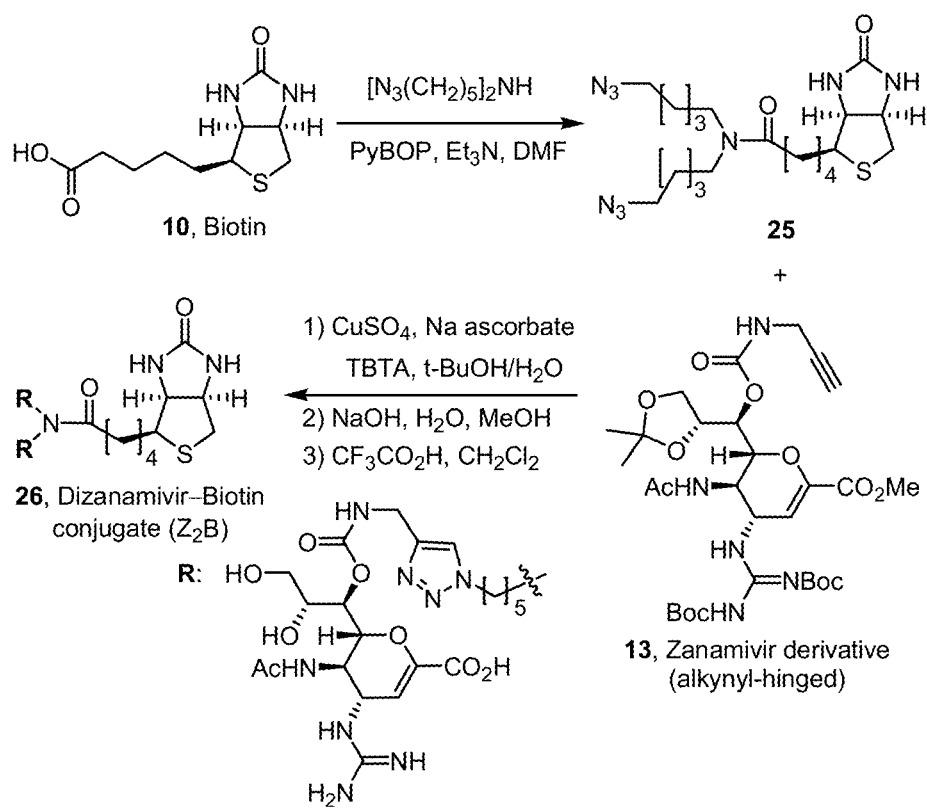
FIG. 6 shows a scheme for synthesis of dizanamivir-biotin conjugate 26

FIG. 4 shows the synthesis of tamiphosphor-biotin conjugate 24. The iodide compound 18 was prepared according to the previously reported procedure. [Shie, J.-J., et al. *Angew. Chem. Int. Ed.* 2008, 47, 5788.] Di[4-(trimethylsilyl)but-3-yn-1-yl] Dialkyl phosphite 17 was prepared by the substitution reaction of $PCl_3$ with two equivalents of 4-(trimethylsilyl)but-3-yn-1-ol. Phosphonylation of 18 with phosphite 19 was achieved by the catalysis of $Pd(PPh_3)_4$ to afford the phosphonate 20 in 64% yield. After removal of the Boc group, the amine intermediate was treated with N,N'-di-Boc-N''-trifluoromethanesulfonyl-guanidine, followed by removal of trimethylsilyl group with KF, to give compound 21. The click reaction of 21 with 5-azidopentanamine, followed by treatment with KOH, afforded phosphonate monoester 22. The coupling reaction of 20 with biotin-OSu (23) culminated in the desired tamiphosphor-biotin conjugate 24 after removal of the protecting Boc groups.

Example 18

Compound 20

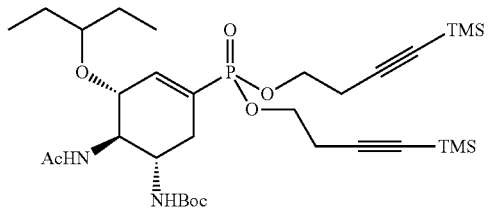 [SMILES: CCC(CC)O[C@@H]1C=C(P(=O)(OCCC#C[Si](C)(C)C)OCCC#C[Si](C)(C)C)C[C@H](NC(=O)OC(C)(C)C)[C@H]1NC(C)=O]

A mixture of iodine 18 (100 mg, 0.21 mmol), phosphite 19 (85 mg, 0.26 mmol) and diisopropylethylamine (100 mg, 0.64 mmol) in anhydrous toluene (2.1 mL) was deoxygenated by bubbling with nitrogen for 10 min, and then added to tetrakis(triphenylphosphine)palladium(0) (10 mg, 8.6 μmol) that was placed in a round bottomed flask under nitrogen atmosphere. The resulting solution was gradually heated to 90° C. and maintained at this temperature for 12 h. The reaction mixture was filtered through a pad of Celite, and the filtrate was evaporated under reduced pressure to give yellow foam (110 mg), which was purified by flash chromatography on a silica gel column [EtOAc/hexane=1:1 to EtOAc] to afford phosphonate 20 (92 mg, 64%). $C_{32}H_{57}N_4O_9P$; yellow oil; TLC (EtOAc/hexane, 1:1) $R_f$=0.29; $^1$H NMR (400 MHz, CDCl$_3$) δ 6.59 (1 H, d, J=22.0 Hz), 5.85 (1 H, d, J=9.2 Hz), 5.04 (1 H, d, J=9.2 Hz), 3.97-4.11 (5 H, m), 3.89 (1 H, br), 3.75-3.81 (1 H, m), 3.29-3.32 (1 H, m), 2.57-2.61 (1 H, m), 2.59 (4 H, t, J=1.2 Hz), 2.20 (1 H, td, J=10.0, 3.2 Hz), 2.00 (3 H, s), 1.43-1.51 (4 H, m), 1.39 (9 H, s), 0.83-0.88 (6 H, m), 0.07-0.21 (18 H, m); $^{13}$C NMR (100 MHz, CDCl$_3$) δ 170.2, 155.6, 142.1, 127.2, 101.2, 87.0, 82.2 (2×), 79.7, 76.0, 63.7 (2×), 54.8, 49.3, 49.1, 31.4, 28.6 (3×), 26.4, 25.9, 23.7, 22.6, 22.5, 10.1, 9.9, 0.5 (6×); $^{31}$P NMR (162 MHz, CDCl$_3$) δ 18.0.

Example 19

Compound 21

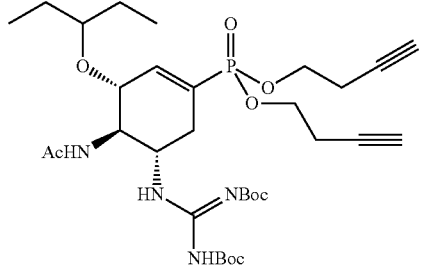

A solution of phosphonate 20 (92 mg, 0.14 mmol) in anhydrous $CH_2Cl_2$ (1.0 mL) was cooled to 0° C. in an ice bath, and trifluoroacetic acid (0.16 mL, 2.1 mmol) was added. The mixture was stirred for 1 h at room temperature, and concentrated under reduced pressure, and then dissolved in anhydrous $CH_2Cl_2$ (1.0 mL). N-N'-Di-Boc-N''-trifluoromethanesulfonylguanidine (67 mg, 0.21 mmol) and triethylamine (0.06 mL, 0.41 mmol) were added. The mixture was stirred at room temperature for 3 h, and extracted with 1 M HCl (5 mL) and $CH_2Cl_2$ (5 mL×3). The organic layer was dried over $MgSO_4$, filtered, concentrated, and purified by flash chromatography on a silica gel column (EtOAc/hexane=1:1) to yield a guanidine derivative.

To a solution of the guanidine compound in MeOH/H$_2$O (1.2 mL/1.2 mL, v/v) was added KF (71 mg, 1.2 mmol). The mixture was stirred at room temperature for 24 h, and then concentrated under reduced pressure. The mixture was extracted with $CH_2Cl_2$ (5 mL×3) and $H_2O$ (5 mL). The organic layer was dried over $MgSO_4$, filtered, concentrated, and purified by flash chromatography on a silica gel column (EtOAc/hexane=1:1) to yield compound 21 (63 mg, 69%). $C_{32}H_{51}N_4O_9P$; colorless oil; TLC (EtOAc/hexane, 1:1) $R_f$=0.24; $[\alpha]_D^{22}$=−27.47 (c=1, $CH_2Cl_2$); IR (film) $v_{max}$ 3450, 2923, 2018, 1925, 1870, 1720, 1626, 1342, 1249, 1203; $^1$H NMR (400 MHz, CDCl$_3$) δ 11.34 (1 H, s), 8.56 (1 H, d, J=8.0 Hz), 6.66 (1 H, d, J=22.4 Hz), 6.28 (1 H, d, J=9.2 Hz), 4.34-4.40 (1 H, m), 4.06-4.16 (5 H, m), 3.96-4.04 (1 H, m), 3.29-3.33 (1 H, m), 2.65-2.71 (1 H, m), 2.59-2.61 (4 H, m), 2.26-2.40 (1 H, m), 2.03 (1 H, s), 2.00 (1 H, s), 1.90 (3 H, s), 1.00-1.78 (22 H, m), 0.83-0.90 (6 H, m); $^{31}$P NMR (162 MHz, CDCl$_3$) δ 18.0; HRMS calcd for $C_{32}H_{52}N_4O_9P$: 667.3472, found: m/z 667.3450 [M+H]$^+$.

Example 20

Tamiphosphor-Biotin Conjugate 24

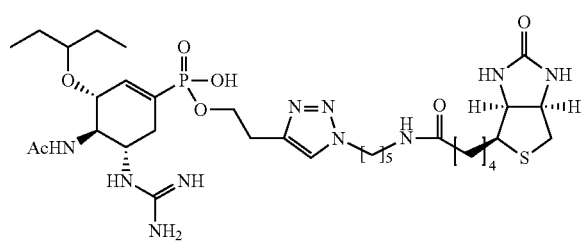

To a solution of 5-azido-1-pentanamine azide (46 mg, 0.36 mmol) and compound 19 (120 mg, 0.18 mmol) in t-BuOH/H$_2$O (0.6 mL, v/v=1:1) was added tetrakis(acetonitrile)copper(I) phosphorus hexafluoride. The mixture was stirred at room temperature for 12 h, concentrated by reduced pressure, and purified on a by RP-18 reversed-phase column with elution of MeOH/H$_2$O (1:9 to 9:1). The crude product of triazole compound was dissolved in 1,4-dioxane (1.0 mL), and added 1 M KOH$_{(aq)}$ (1.0 mL). The solution was stirred at 25° C. for 120 h (monitored by $^1$H NMR), and added Dowex 50W×8 to neutralize the solution. The mixture was filtered and concentrated under reduced pressure. The crude product (10 mg, 0.013 mmol) was dissolved in anhydrous DMF (0.1 mL), and biotin-OSu (4.5 mg, 0.013 mmol) and diisopropylethylamine (4.2 mg, 0.026 mmol) were added. The mixture was stirred at room temperature for 3 h, and concentrated under reduced pressure. The residue was dissolved in MeOH (0.5 mL), cooled to 0° C. in an ice bath, and added trifluoroacetic acid (0.16 mL, 2.1 mmol). The mixture was stirred for 1 h at room temperature, concentrated under reduced pressure, and purified on a RP-18 reversed-phase column with elution of MeOH/H$_2$O (1:9 to 9:1) to give the title compound (40 mg, 30% overall yield). C$_{33}$H$_{57}$N$_{10}$O$_7$PS; yellow solid; $^1$H NMR (400 MHz, CDCl$_3$) δ 7.89 (1 H, s), 6.39 (1 H, d, J=19.6 Hz), 4.90 (1 H, t, J=5.2 Hz), 4.38 (1 H, t, J=7.2 Hz), 4.29-4.32 (1 H, m), 4.00 (2 H, m), 3.77-3.90 (2 H, m), 3.40-3.48 (2 H, m), 3.15-3.26 (2 H, m), 3.00 (1 H, t, J=5.2 Hz), 2.91-2.95 (2 H, m), 2.71 (1 H, d, J=12.8 Hz), 2.53-2.62 (2 H, m), 2.23 (2 H, t, J=7.2 Hz), 1.90-2.03 (5 H, m), 1.29-1.79 (16 H, m), 0.86-0.97 (6 H, m); $^{31}$P NMR (162 MHz, CDCl$_3$) δ 13.6; HRMS negative mode calcd for C$_{33}$H$_{56}$N$_{10}$O$_7$PS: 768.3723, found: m/z 768.3723 [M–H]$^-$.

Example 21

Compound 25

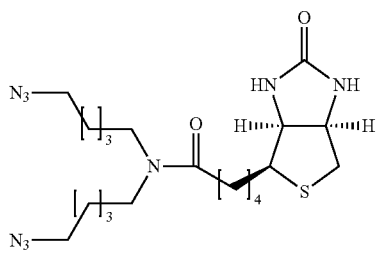

To a solution of di(5-azidopentyl)amine (0.12 g, 0.49 mmol) in anhydrous DMF (5 mL) of were added biotin (0.12 g, 0.41 mmol), PyBOP (0.25 g, 0.49 mmol) and Et$_3$N (0.23 mL, 1.64 mmol). The mixture was stirred for 22 h at room temperature under argon, and then concentrated under reduced pressure. The residue was purified by column chromatography (silica gel, CH$_2$Cl$_2$/MeOH=13:1) to give biotin-diazide compound 25 (0.15 g, 79%). C$_{20}$H$_{35}$N$_9$O$_2$S; pale yellow oil; $^1$H NMR (CDCl$_3$, 600 MHz) δ 4.48 (dd, J=7, 5 Hz, 1 H), 4.29 (dd, J=7, 5 Hz, 1 H), 3.28 (t, J=7 Hz, 4 H), 3.25 (t, J=7 Hz, 4 H), 3.20 (t, J=7 Hz, 2 H), 2.89 (dd, J=12, 5 Hz, 1 H), 2.71 (d, J=12 Hz, 1 H), 2.29 (t, J=7 Hz, 2H), 1.84 (br s, 3 H), 1.50-1.67 (m, 8 H), 1.43-1.44 (m, 2 H), 1.32-1.38 (m, 4 H); $^{13}$C NMR (CDCl$_3$, 150 MHz) δ 172.4, 163.2, 61.8, 60.1, 55.3, 51.2, 47.0, 46.2, 45.6, 40.5, 32.5, 28.7, 28.6, 28.3, 27.3, 26.4, 25.1, 24.1. ESI-HRMS calcd for C$_{20}$H$_{36}$N$_9$O$_2$S: 466.2707, found: m/z 466.2703 [M+H]$^+$.

Example 22

Dizanamivir-Biotin Conjugate 26

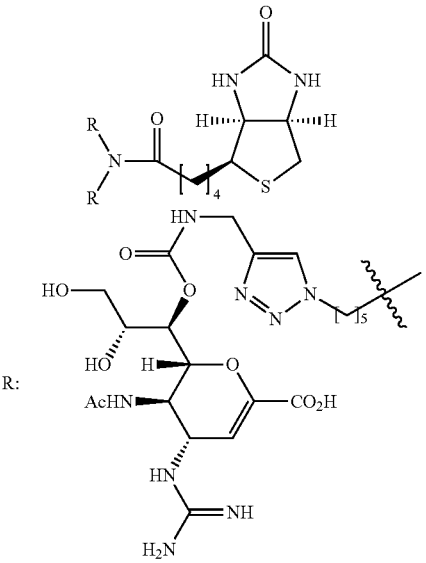

To a solution of biotin-diazide 25 (36 mg, 0.075 mmol) in t-BuOH (1 mL) and H$_2$O (1 mL) were added CuSO$_4$.5H$_2$O (4 mg, 0.015 mmol), sodium ascorbate (10 mg, 0.045 mmol), and TBTA (8 mg, 0.015 mmol). The mixture was stirred for 5 min, and the alkynyl-hinged zanamivir derivative 13 (0.1 g, 0.15 mmol) was added. The mixture was stirred for 12 h at room temperature, extracted with CH$_2$Cl$_2$ (20 mL) and H$_2$O (20 mL), dried over MgSO$_4$, and concentrated under reduced pressure. The residue was purified by column chromatography (silica gel, CH$_2$Cl$_2$/MeOH=9.5:1) to give the coupling product (64 mg, 47%). $^1$H NMR (CDCl$_3$, 600 MHz) δ 1.22 (s, 12 H), 1.30 (s, 36 H), 1.62 (s, 4 H), 1.79 (s, 2 H), 1.89 (s, 3 H), 1.94 (s, 3H), 2.23 (t, J=7 Hz, 2 H), 2.74 (d, J=12 Hz, 1 H), 2.88 (d, J=12 Hz, 1 H), 3.10-3.16 (m, 4 H), 3.23 (s, 2 H), 3.75 (s, 6 H), 3.98 (t, J=7 Hz, 2 H), 4.06 (t, J=8 Hz, 2 H), 4.15 (t, J=10 Hz, 2 H), 4.28-4.43 (m, 14 H), 5.16 (s, 2 H), 5.23 (t, J=6 Hz, 2 H), 5.35 (s, 1 H), 5.70 (s, 1 H), 5.86 (d, J=8 Hz, 2 H), 6.04 (s, 1 H), 6.28 (s, 1 H), 6.54 (d, J=9 Hz, 1 H), 6.63 (d, J=9 Hz, 1 H), 7.79 (s, 2 H), 8.42 (d, J=8 Hz, 2H), 11.38 (s, 2 H).

The above-prepared coupling product (60 mg, 0.033 mmol) in MeOH (1 mL) was stirred with NaOH (1 mL of 1 M aqueous solution) for 1 h at room temperature, neutralized with Dowex 50W×8 (H$^+$), and filtered. After concentration, the residue was dissolved in CH$_2$Cl$_2$ (1 mL) and TFA (1 mL). The mixture was stirred for 1 h at room temperature, concentrated under reduced pressure, and purified by chromatography on a Sephadex G-10 column (eluent: 0.1% TFA in H$_2$O) to give the dizanamivir-biotin conjugate 26 (50 mg, 43%). C$_{52}$H$_{81}$N$_{19}$O$_{18}$S; $^1$H NMR (CDCl$_3$, 600 MHz) δ 1.29-1.33 (m, 6 H), 1.45 (br s, 2 H), 1.56-1.61 (m, 8 H), 1.75 (br s, 1 H), 1.84-1.87 (m, 1 H), 1.97-2.04 (m, 12 H), 2.36 (br s, 2 H), 2.73 (d, J=12 Hz, 1 H), 2.94 (d, J=12 Hz, 1 H), 3.51 (br s, 2 H), 3.65 (d, J=10 Hz, 2H), 3.69 (s, 2 H), 3.78 (s, 4 H), 4.00 (br s, 2 H), 4.19 (br s, 2 H), 4.37-4.45 (m, 11 H), 4.55 (br s, 4 H), 4.68 (d, J=8 Hz, 4 H), 5.91 (s, 2 H), 7.57 (s, 1 H), 8.05 (s, 2 H); ESI-HRMS calcd for $C_{52}H_{82}N_{19}O_{18}S$: 1292.5800, found: m/z 1292.5916 $[M+H]^+$.

Example 23

Cells, Viruses, and Biological Reagents

Both the MDCK and the 293T cells and two influenza viruses: A/Aichi/2/68 (H3N2) and B/Lee/40 were obtained from ATCC (Manassas, Va., USA), respectively. Influenza viruses A/WSN/1933 (H1N1), A/Udorn/307/1972 (H3N2), A/PR/8/1934 (H1N1), A/Taiwan/3446/2002 (H3N2), influenza B/Taiwan/7064/2004 isolates were from Dr. Shin-Ru Shih's lab (Chang Gung University, Taiwan), and A/Vietnam/1194/2004 RG14 (H5N1), A/California/7/2009 (H1N1), A/Brisbane/10/2007 (H1N1) and A/Brisbane/10/2007 (H3N2) were from Dr. Jia-Tsrong Jan's lab (Genomics Research Center, Academia Sinica, Taiwan). The oseltamivir resistant WSN mutant was selected by 6 passages in MDCK cells with gradually increased OC (oseltamivir carboxylate) concentrations. This mutant influenza grows well in the presence of 1 µM OC and carries a single H274Y mutation at its NA gene confirmed by sequence analysis. Other Taiwan clinical H1N1 isolates were obtained from the influenza collection center of Center for Disease Control (Taipei, Taiwan) and are described in Table 1. Seven S-OIV isolates were also obtained from Center for Disease Control (Taipei, Taiwan) and were coded as #1 (A/Taiwan/T1941/2009), #2 (A/Taiwan/T1338/2009), #3 (A/Taiwan/T1339/2009), #4 (A/Taiwan/6662/2009), #5 (A/Taiwan/6663/2009), #6 (A/Taiwan/7717/2009), and #7 (A/Taiwan/7855/2009). The antibodies for influenza NP and the fluorescein-labeled secondary antibody were purchased from Chemicon Inc. (Billerica, Mass., USA) and Sigma (St. Louis, Mo., USA), respectively. Anti-WSN rabbit antibody was prepared in the lab using inactivated WSN influenza as the antigen. The anti-HA antibody (Abcam, Cambridge, Mass., USA) was purchased from Interlab Ltd. (Taipei, Taiwan).

Example 24

Development of the OC Susceptibility Assay Using Neuraminidase Expressing Cells

Figure 10:
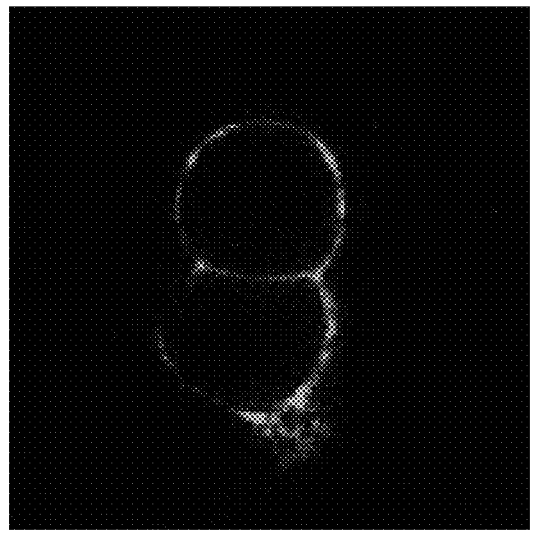
FIG. 10 shows ZB (zanamivir biotin) binding at the surface of 293T cells expressing neuraminidase cDNA of A/Hanoi/30408/2005 H5N1. The 293T cells were transfected with NA expression vector pcDNA3.1-NA by Lipofectamine™ 2000 (Invitrogen, Carlsbad, USA). After 48 hours, the transfected cells were stained with 100 nM Zanamivir-Biotin (ZB) and further incubated with DyLight 488-conjugated streptavidin. Immunofluorescence image was captured using a Leica TCS-SP5 laser scanning confocal microscope.
Figure 11:
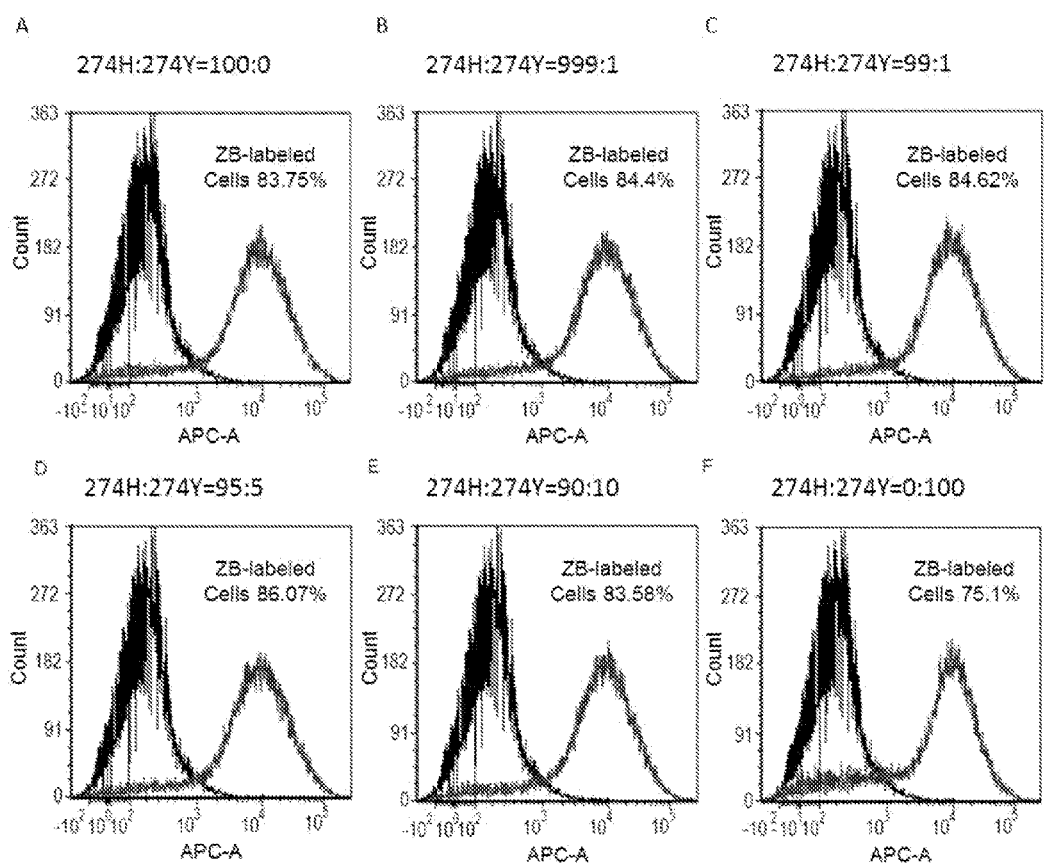
FIGS. 11A-11F show ZB binding of mixed 293 cells with varied contents of cells expressing OC resistant neuraminidase. Recombinant 293T cells expressing OC sensitive (274H) and OC resistant (274Y) cells were mixed to different ratios as indicated: (11A) 274H:274Y=100:0, (11B) 274H:274Y=999:1, (11C) 274H:274Y=99:1, (11D) 274H:274Y=95:5, (11E) 274H:274Y=90:10, (11F) 274H:274Y=0:100. The mixed cells were treated with 10 nM ZB at room temperature for 1 hr followed by further decoration with APC-conjugated streptavidin and analyzed by FACSCanto (Becton Dickinson) and FCS Express 3.0 software. The percentage of ZB labeled cells were 11A, 83.95%; 11B, 84.4%; 11C, 84.62%; 11D, 86.07%; 11E, 83.58%; and 11F, 75.1%.
Figure 12:
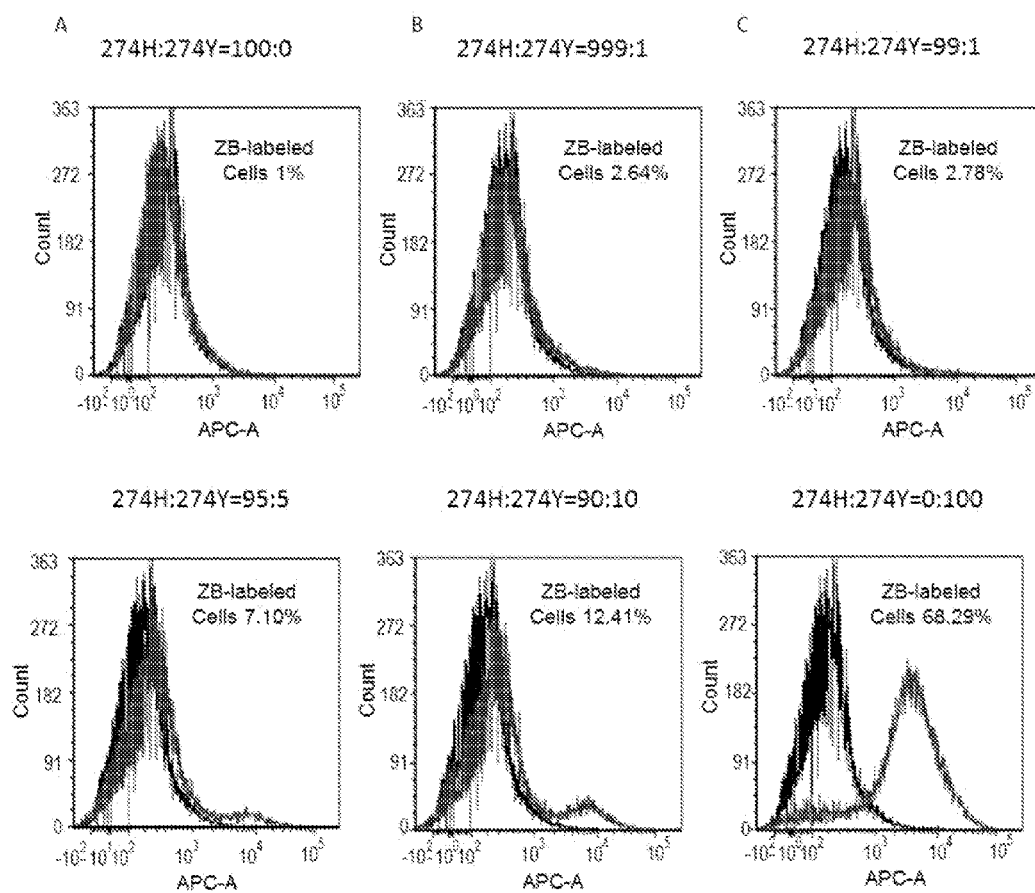
FIGS. 12A-12F show oseltamivir carboxylate resistant ZB binding on mixed 293T cells with varied contents of cells expressing OC resistant neuraminidase. The cells as in FIG. 11 were treated with 10 nM ZB and excess OC at 300 nM and processed similarly. The percentage of ZB labeled cells were 12A, 1.00%; 12B, 2.64%; 12C, 2.78%; 12D, 7.10%; 12E, 12.41%; and 12F, 68.29%.
Figure 13:
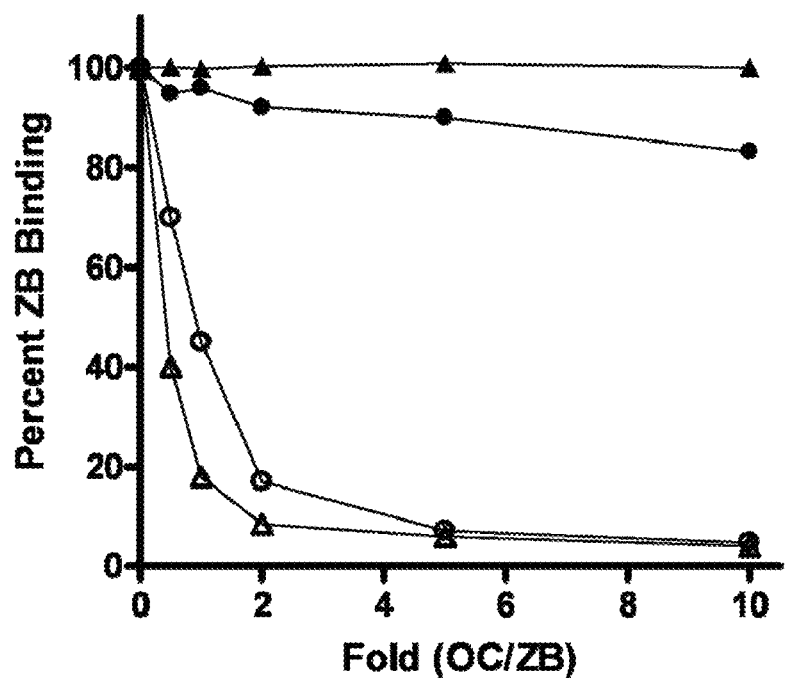
FIGS. 13A-13B show OC competition of ZB binding to influenza virus infected MDCK cells. (13A) MDCK cells were infected with OC susceptible 274H or OC resistant 274Y viruses. At 20 hr post-infection, the 274H virus infected cells were incubated with ZB at 10 nM (open triangle) or 50 nM (open circle) in the presence of varied concentrations of competing OC. Similarly, the 274Y infected cells were also incubated with 10 nM ZB (closed triangle) or 50 nM ZB (closed circle) with varied OC contents. Cells with bound ZB were further incubated with streptavidin conjugated alkaline phosphatase to determine the relative ZB binding at different competing OC concentrations. (13B) Image of MDCK cells infected with OC susceptible (274H) or OC resistant (274Y) WSN viruses and incubated either with 30 nM ZB or 30 nM ZB plus 150 nM OC followed by incubation with streptavidin conjugated PE. The fluorescence images were captured using a laser driven plate reader exited and emitted at 488 and 575 nm, respectively.
Figure 13:
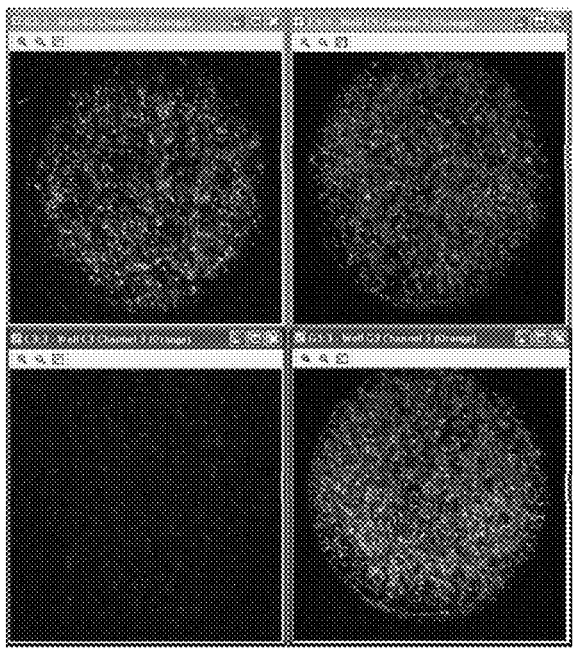

The neuraminidase inhibitory activities of zanamivir and ZB were compared and it was found that ZB is still a very potent inhibitor for neuraminidase with an $IC_{50}$ of 7 nM although it is slightly less active then zanamivir with an $IC_{50}$ of 2 nM. Functional neuraminidase expressed on the cell surface could be useful as a model system for ZB binding and OC competition for OC susceptibility assessments. The cDNA for the neuraminidase of A/Hanoi/30408/2005 (H5N1) was cloned in an expression plasmid and used to transfect 293T cells for the expression of the wild type (274H) neuraminidase. The expressed neuraminidase was found to be located mainly on the cell surface allowing the binding and labeling using ZB (FIG. 10). The neuraminidase cDNA was mutagenized for the expression of the OC resistant 274Y mutant enzyme. Both the wild type and the mutagenized cDNA were used to generate stable 293T cell lines for the expression of the 274H and 274Y neuraminidases, respectively. Mixtures of these two cells at different ratios were incubated with ZB or ZB plus excess OC and then decorated with APC conjugated streptavidin to determine the population of cells that bind ZB by flow cytometry analyses. FIG. 11 shows that ZB bound 274H and 274Y expressing cells to similar extents. In the presence of excess OC, ZB binding was completely blocked in cells expressing 274H neuraminidase, whereas ZB binding to the 274Y expressing cells was virtually unaltered (FIG. 12). These results prove the principle that ZB binding can be used to differentiate OC-sensitive and OC-resistant neuraminidases by OC competition.

Example 25

Determination of OC Susceptibility Using Influenza Virus Infected Cells

The results of the competitive OC inhibition on ZB binding using NA expressing cells had prompted us to define the concentrations of ZB and OC to assess the OC susceptibility of influenza viruses. MDCK cells infected with either OC susceptible or OC resistant WSN viruses were used to test feasibility of the OC susceptibility assessment using varied ZB and OC concentrations. FIG. 13A shows OC competition of ZB binding to influenza virus infected MDCK cells. By labeling influenza infected cells with either 10 or 50 nM ZB, OC susceptibility of infecting viruses could be inferred from the competition binding with OC at 0.5-10 fold concentrations of the labeling ZB. For example, clear distinction of OC susceptible and OC resistant WSN variants was observed by treating infected cells using labeling ZB at 30 nM and competing OC at 150 nM (FIG. 13B).

MDCK cells were infected with either wild type (274H) or OC resistant (274Y) WSN viruses. At 16-20 hr post-infection, the infected cells were treated either with 30 nM ZB or with 30 nM ZB plus 150 nM OC. The resulting cells were decorated with streptavidin-FITC, washed and observed using a fluorescence microscope. For flow cytometry studies, the ZB labeled cells were further labeled using anti-NP antibody, trypsinized, and then treated with PE-conjugated streptavidin plus DyLight-649 labeled anti-rabbit second antibody, both were purchased from Jackson ImmunoResearch Laboratories (West Grove, Pa., USA). After additional washings, the cells were analyzed by FACSCanto of BD Biosciences (San Jose, Calif., USA). For analysis of more samples, a high throughput method was developed using black 96-well clear bottom microplates to culture infected cells. At 16-20 hr post-infection, cells were labeled with 30 nM ZB or 30 nM ZB plus 150 nM OC, washed, and treated with PE-streptavidin. The plates were then scanned with the Isocyte™ laser scanning platform of Molecular Device (Mountain View, Calif., USA) at 488 nm.

Example 26

Estimation of OC Resistant Contents Using Immobilized Influenza Samples

Figure 7:
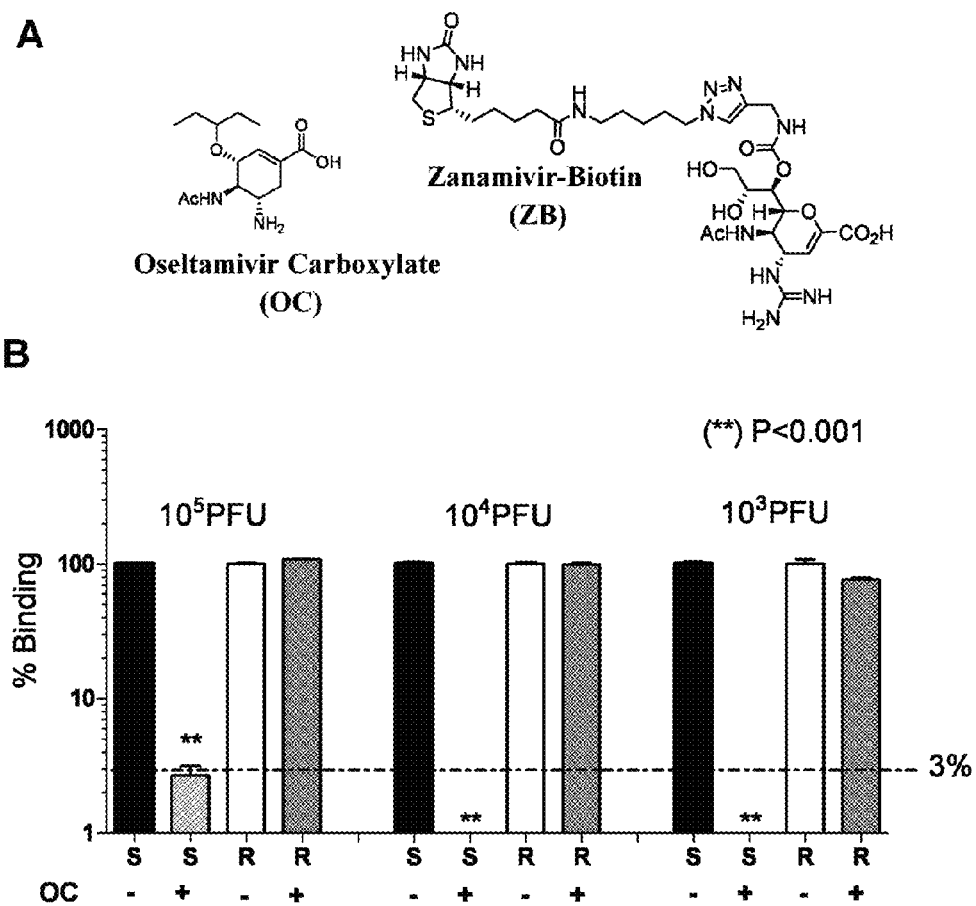
FIGS. 7A-7B show determination of oseltamivir carboxylate (OC) susceptibility using immobilized influenza samples. (7A) Structures of compounds used in this study. (7B) OC susceptible (S) or OC resistant (R) WSN virus samples were immobilized in anti-HA coated microplate wells at $10^5$, $10^4$, or $10^3$ PFU per well. The immobilized viral samples in triplicate wells were incubated with 30 nM ZB for total binding or with 30 nM ZB plus competing OC at 150 nM to measure OC resistant ZB binding. The bound viruses were further incubated with streptavidin conjugated alkaline phosphatase followed by the chemiluminescent substrate to measure the relative luminescence units (RLU) increases due to the catalysis by the bound alkaline phosphatase. The values of OC resistant ZB binding were calculated as the ratios of RLU measured in the presence of OC competition and those measured in the absence of OC. Conditions resulting in significant binding reductions by competing OC are labeled with "**" for $p<0.001$. The dashed line marked the 3% residual ZB binding that could not be inhibited completely with OC when high titer ($10^5$ PFU per well) 274H viral samples were employed.

As described with reference to FIG. 7B, the RABC assay is applicable for OC susceptibility determinations using immobilized viruses in micro-wells. The RABC assay using immobilized viruses could also be used to estimate the contents of OC resistant mutants in a mixed population consisting of both OC susceptible and resistant viruses. Viral samples at different ratios of 274H and 274Y WSN viruses in total viral contents at $10^3$, $10^4$, and $10^5$ PFU per well were immobilized to measure OC resistant ZB binding as an estimation of OC resistant contents. FIG. 14 shows that the estimated OC resistant contents matched well with the experimental 274Y viral contents that are greater than 10%. For mixed populations containing less than 10% resistant viruses, over-estimation of the resistant contents was observed probably due to the background binding that are higher in assays using high titer viral samples.

High binding 96-well microplates 655061 from Greiner Bio-One (Frickenhausen, Germany) were coated overnight with anti-HA antibody (Abcam) at 150 ng per well and then blotted using PBS with 3% BSA. Influenza samples were treated with 30 nM ZB or 30 nM ZB plus 150 nM OC for 30 min and added to antibody coated wells. After incubation for 30 min, the microwells were washed with 3% BSA in PBS, added with alkaline phosphatase conjugated streptavidin for 30 min, washed again with BSA in PBS and then added with the luminescence substrate Emerald-II™ according to the instruction of the manufacturer (Invitrogen, Carlsbad, Calif., USA). The RLU (Relative Luminescence Unit) was read using Envision from Perkin Elmer (Waltham, Mass., USA). Percent relative resistance was calculated as the percent RLU determined for ZB binding measured in the presence of OC divided by total RLU for ZB binding measured in the absence of OC competition.

Example 27

Determination of Influenza Neuraminidase Sequences

Total RNA was extracted from influenza viruses using High Pure Viral RNA kit from Roche Diagnostics purchased at Taipei Pharma (Taipei, Taiwan). The RNA samples were reverse transcribed using random hexamers and the MMLV RTase of Toyobo Life Science Department (Tokyo, Japan) for the synthesis of cDNA that was amplified by PCR using two primers 5'-tggtcagcaagtgcwtgccatg (SEQ ID NO: 1), and 5'-gacactggaccacaactgcct (SEQ ID NO: 2) at 200 nM. The DNA products were purified and used to determine the NA sequences.

Example 28

Rapid Detection of OC Susceptibility of Influenza Viruses on Membrane

PVDF membrane mounted on Bio-Dot SF of Bio-Rad Inc. (Bio-Rad, CA, USA) was wetted with methanol and added with 1 µg anti-HA antibody (Abcam) per slot by suction. Influenza viral samples that were previously treated for 1 hr with either 30 nM ZB or 30 nM ZB plus 150 nM OC were introduced to neighboring slots by suction. The membranes were blotted using PBS with 3% BSA and then incubated with alkaline phosphatase conjugated streptavidin from KPL (Gaithersburg, Md., USA) according to the manufacturer's instruction. After additional washing using PBS with 3% BSA, alkaline phosphatase substrate, Amresco E116 solution of Amresco Inc. (Solon, Ohio, USA) was added for color development. Visible color usually was developed in 2 minutes and recorded by photography.

Example 29

Preparation of 293T Cells Stably Expressing Recombinant Wild Type (274H) and OC Resistant (274Y) Neuraminidases The cDNA sequence of the neuraminidase gene deduced from influenza A/Hanoi/30408/2005 (H5N1) (GeneBank: AB239126.1) was used to prepare a synthetic version of this gene by Geneart (Regensburg, Germany) and cloned into the BamH1 and XhoI restriction sites of pcDNA3.1 of Invitrogen (Carlsbad, Calif., USA) as pCDNA3.1-NA. The NA gene was modified using QuickChange® XL Site-Directed Mutagenesis Kit from Agilent Technology (La Jolla, Calif., USA) to produce OC resistant NA mutant of H274Y using a pair of primers: 5'-gCTggACgCTCCCAACTACCACTACgAg-gAgTg-3' (SEQ ID NO: 3) and 5'-gTAgTTgggAgCgTC-CAgCTCCACggAC-3(SEQ ID NO: 4). Both the wild type (274H) and the OC resistant mutant (274Y) NA genes were validated by sequence analyses. These NA genes were used for transient NA expressions for wild type and OC resistant neuraminidases. They were also cloned into the pRetro-IRES-GFP vector of Clontech (Mountain View, Calif., USA) as pRetro-NA(274H)-IRES-GFP and pRetro-NA(274Y)-IRES-GFP, respectively. Recombinant retroviruses made using these two plasmids and pGagPol, and pVSVG were used to transduce 293T cells. Stable cell lines were selected by fluorescence-activated cell sorter for populations expressing GFP over 95% and validated for the synthesis of OC susceptible or resistant neuraminidases.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claim.

What is claimed is:

1. A composition for inhibiting influenza virus neuraminidase, the composition comprising:

a therapeutically effective amount of at least one of the compounds:

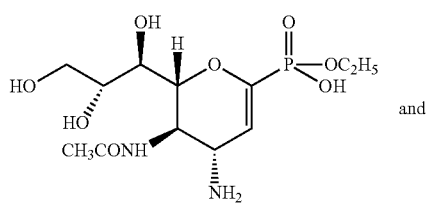

(1c)

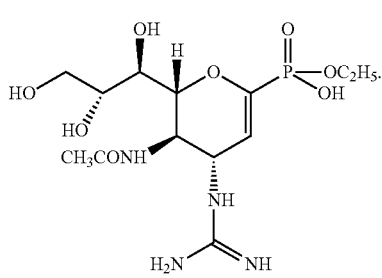

(1d)

or a pharmaceutically effective salt thereof; and a pharmaceutically acceptable excipient.

2. A composition for inhibiting influenza virus neuraminidase, the composition comprising:

a therapeutically effective amount of at least one of the compounds:

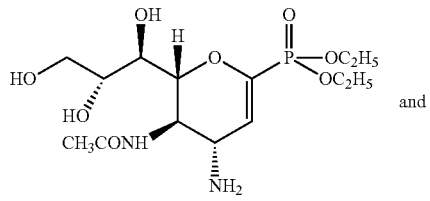

(1e)

and

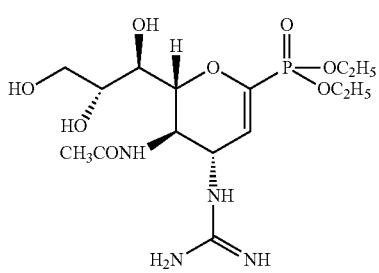

(1f)

or a pharmaceutically effective salt thereof; and a pharmaceutically acceptable excipient.

3. The composition of any of claims 1 or 2, wherein the composition binds to influenza virus strains H1N1, H5N1, and H3N2.

4. The composition as according to claim 3, wherein the composition binds to a wild type or a H274Y m 5. A process for manufacturing the compound of any of claims 1 or 2, the process comprising the steps of:

(a) acetylating a chiral precursor sialic acid (2)

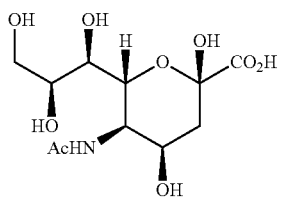 [SMILES: CC(=O)N[C@H]1[C@H]([C@H](O)[C@@H](O)CO)O[C@](O)(C(=O)O)C[C@H]1O]

to prepare an intermediate compound (3):

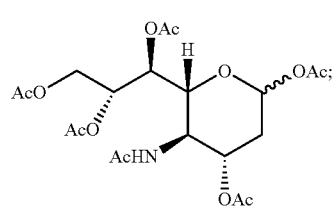

(3)

(b) treating intermediate compound (3) with diethyl trimethylsilyl phosphite to form intermediate compound (4):

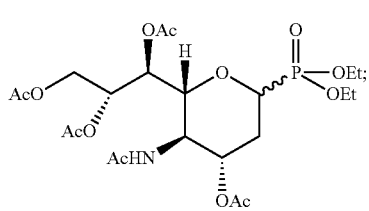

(4)

(c) treating intermediate (4) with N-bromosuccinimide under light irradiation to give a bromo-substituted compound, which forms intermediate (5) in pyridine:

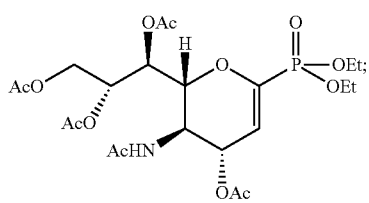

(5)

(d) treating intermediate compound (5) with trimethylsilyl trifluorosulfonate to form intermediate compound (6):

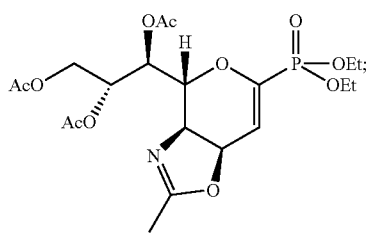

(6)

and (e) treating intermediate compound (6) with trimethylsilyl azide to form intermediate compound (7):

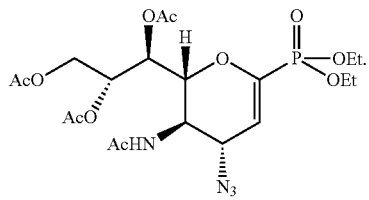

(7)

6. The process of claim 5, further comprising the step of:
(f) hydrogenating intermediate compound (7), and then reacting with 1,3-bis(tert-butoxycarbonyl)-2-methylthiopseudourea and Et3N to form intermediate compound (8):

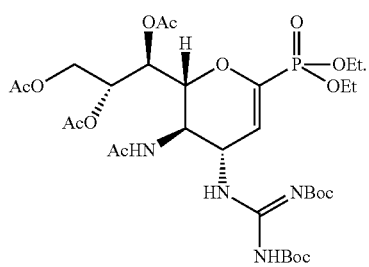

(8)

7. The process of claim 5, further comprising the step of:
(g) treating intermediate compound (7) with bromotrimethylsilane, with sodium methoxide and then hydrogenating in sequence, to form compound (1a):

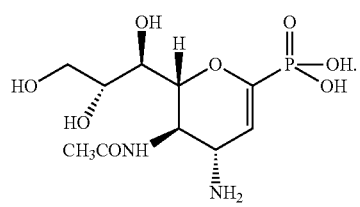

(1a)

8. The process of claim 5, further comprising the step of:
(i) treating intermediate compound (7) with sodium ethoxide and then hydrogenating to form compound (1c):

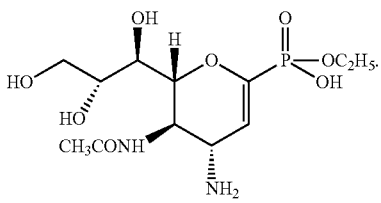

(1c)

9. The process of claim 6, further comprising the step of:
(h) treating intermediate compound (8) with bromotrimethylsilane, and then with sodium methoxide to form compound (1b):

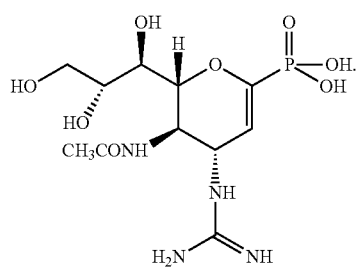

(1b)

10. The process of claim 6, further comprising the step of:
(j) treating intermediate compound (8) with sodium ethoxide and then trifluoroacetic acid to form compound (1d):

$$\text{(1d)}$$

11. A method for treating influenza infection, the method comprising:
    providing a therapeutically effective amount of a composition according to any of claims 1 or 2 to a subject in need thereof.

12. The method of claim 11, wherein the subject is a human or non-human mammal.

13. The method of claim 11, wherein the subject is suspected of being infected to an influenza virus comprising a wild type or a H274Y neuraminidase mutant.

14. The method of claim 13, wherein the influenza virus strain is selected from H1N1, H5N1, and H3N2.

* * * * *